(12) United States Patent
Haynes et al.

(10) Patent No.: US 10,076,567 B2
(45) Date of Patent: Sep. 18, 2018

(54) MPER-LIPOSOME CONJUGATES AND USES THEREOF

(71) Applicants: Duke University, Durham, NC (US); Los Alamos National Security, LLC, Los Alamos, NM (US)

(72) Inventors: Barton F. Haynes, Durham, NC (US); Bette T. Korber, Los Alamos, NM (US); S. Munir Alam, Durham, NC (US)

(73) Assignees: DUKE UNIVERSITY, Durham, NC (US); LOS ALAMOS NATIONAL SECURITY, LLC, Los Alamos, NM (US)

( * ) Notice: Subject to any disclaimer, the term of this patent is extended or adjusted under 35 U.S.C. 154(b) by 0 days.

(21) Appl. No.: 15/024,600

(22) PCT Filed: Sep. 29, 2014

(86) PCT No.: PCT/US2014/058032
§ 371 (c)(1),
(2) Date: Mar. 24, 2016

(87) PCT Pub. No.: WO2015/048635
PCT Pub. Date: Apr. 2, 2015

(65) Prior Publication Data
US 2017/0014503 A1 Jan. 19, 2017

Related U.S. Application Data

(60) Provisional application No. 61/883,306, filed on Sep. 27, 2013.

(51) Int. Cl.
| | |
|---|---|
| *A61K 39/21* | (2006.01) |
| *A61K 38/16* | (2006.01) |
| *A61K 38/21* | (2006.01) |
| *A61K 9/127* | (2006.01) |
| *A61K 9/00* | (2006.01) |
| *A61K 39/12* | (2006.01) |
| *A61K 47/48* | (2006.01) |
| *C07K 14/005* | (2006.01) |
| *A61K 39/39* | (2006.01) |
| *C12N 7/00* | (2006.01) |
| *A61K 39/00* | (2006.01) |

(52) U.S. Cl.
CPC ............ *A61K 39/21* (2013.01); *A61K 9/0019* (2013.01); *A61K 9/127* (2013.01); *A61K 38/162* (2013.01); *A61K 38/212* (2013.01); *A61K 39/12* (2013.01); *A61K 39/39* (2013.01); *A61K 47/48815* (2013.01); *C07K 14/005* (2013.01); *C12N 7/00* (2013.01); *A61K 2039/545* (2013.01); *A61K 2039/55555* (2013.01); *A61K 2039/55572* (2013.01); *A61K 2039/575* (2013.01); *C12N 2740/16022* (2013.01); *C12N 2740/16034* (2013.01); *C12N 2740/16122* (2013.01); *C12N 2740/16134* (2013.01)

(58) Field of Classification Search
CPC ..................... A61K 39/21; A61K 2039/55555
See application file for complete search history.

(56) References Cited

U.S. PATENT DOCUMENTS

| | | |
|---|---|---|
| 4,994,440 A | 2/1991 | Creaven |
| 5,565,332 A | 10/1996 | Hoogenboom et al. |
| 5,693,752 A | 12/1997 | Katinger et al. |
| 5,707,626 A | 1/1998 | Douvas et al. |
| 5,733,743 A | 3/1998 | Johnson et al. |
| 5,756,674 A | 5/1998 | Katinger et al. |
| 5,831,034 A | 11/1998 | Katinger et al. |
| 5,837,242 A | 11/1998 | Holliger et al. |
| 5,858,657 A | 1/1999 | Winter et al. |
| 5,866,694 A | 2/1999 | Katinger et al. |
| 5,871,907 A | 2/1999 | Winter et al. |
| 5,877,218 A | 3/1999 | Herzig et al. |
| 5,910,306 A | 6/1999 | Alving et al. |
| 5,916,588 A | 6/1999 | Popescu et al. |
| 5,919,459 A | 7/1999 | Nacy et al. |
| 6,156,337 A | 12/2000 | Barenholz et al. |
| 6,300,308 B1 | 10/2001 | Schroit |

(Continued)

FOREIGN PATENT DOCUMENTS

| | | |
|---|---|---|
| CN | 102485273 A | 6/2012 |
| EP | 1250933 A1 | 10/2002 |

(Continued)

OTHER PUBLICATIONS

Verkoczy et al., 'Induction of fflV 1 broad neutralizing antibodies in 2F5 knock in mice: selection against membrane proximal external region associated autoreactivity limits T dependent responses' The Journal of Irmlunology, Vo1.191, No. 5, pp. 2538 2550 (e pub. Aug. 5, 2018).*

(Continued)

*Primary Examiner* — Jeffrey Parkin
(74) *Attorney, Agent, or Firm* — Wilmer Cutler Pickering Hale and Dorr LLP

(57) ABSTRACT

The present invention relates to peptides and compositions suitable for use in inducing anti-HIV-1 antibodies. The compositions comprise HIV-1 gp41 membrane proximal external region (MPER) peptide-liposome conjugates for induction of broadly reactive anti-HIV-1 antibodies. The invention also relates to methods of inducing neutralizing anti-HIV-1 antibodies using such compositions.

31 Claims, 56 Drawing Sheets
Specification includes a Sequence Listing.

(56) References Cited

U.S. PATENT DOCUMENTS

| | | | |
|---|---|---|---|
| 6,761,888 B1 | 7/2004 | Schenk | |
| 6,806,354 B2 | 10/2004 | Schroit | |
| 7,195,768 B2 | 3/2007 | Haynes et al. | |
| 7,459,165 B2 | 12/2008 | Charland et al. | |
| 8,956,627 B2 * | 2/2015 | Haynes | A61K 39/21 424/196.11 |
| 9,402,893 B2 * | 8/2016 | Haynes | A61K 39/0005 |
| 9,402,917 B2 * | 8/2016 | Alam | A61K 38/212 |
| 2001/0036461 A1 | 11/2001 | Haynes et al. | |
| 2003/0181406 A1 | 9/2003 | Schetter et al. | |
| 2004/0006032 A1 | 1/2004 | Lopez | |
| 2004/0006242 A1 | 1/2004 | Hawkins et al. | |
| 2004/0053880 A1 | 3/2004 | Krieg | |
| 2004/0067905 A1 | 4/2004 | Krieg | |
| 2004/0092472 A1 | 5/2004 | Krieg | |
| 2004/0131610 A1 | 7/2004 | Thorpe et al. | |
| 2004/0131621 A1 | 7/2004 | Thorpe et al. | |
| 2004/0131622 A1 | 7/2004 | Thorpe et al. | |
| 2004/0152649 A1 | 8/2004 | Krieg | |
| 2004/0161429 A1 | 8/2004 | Thorpe et al. | |
| 2004/0171086 A1 | 9/2004 | Fink et al. | |
| 2004/0198680 A1 | 10/2004 | Krieg | |
| 2004/0213779 A1 | 10/2004 | Thorpe et al. | |
| 2004/0241641 A1 | 12/2004 | Stiegler et al. | |
| 2004/0265367 A1 | 12/2004 | Thorpe et al. | |
| 2005/0025761 A1 | 2/2005 | Thorpe et al. | |
| 2005/0059619 A1 | 3/2005 | Krieg et al. | |
| 2005/0080240 A1 | 4/2005 | Kunert et al. | |
| 2005/0095282 A1 | 5/2005 | Schroit | |
| 2006/0089326 A1 | 4/2006 | Krieg et al. | |
| 2008/0031890 A1 | 2/2008 | Haynes et al. | |
| 2008/0057075 A1 | 3/2008 | Haynes | |
| 2009/0035360 A1 | 2/2009 | Lemoine | |
| 2009/0220536 A1 | 9/2009 | Ofek et al. | |
| 2010/0028415 A1 | 2/2010 | Haynes et al. | |
| 2010/0047331 A1 | 2/2010 | Haynes et al. | |
| 2011/0142869 A1 * | 6/2011 | Berkower | A61K 39/21 424/188.1 |
| 2012/0070488 A1 | 3/2012 | Haynes et al. | |
| 2012/0128758 A1 | 5/2012 | Alam et al. | |
| 2012/0183597 A1 | 7/2012 | Haynes et al. | |
| 2013/0323299 A1 | 12/2013 | Haynes et al. | |
| 2014/0322262 A1 | 10/2014 | Spicer et al. | |
| 2015/0147387 A1 | 5/2015 | Haynes et al. | |

FOREIGN PATENT DOCUMENTS

| | | |
|---|---|---|
| JP | 2006-512391 A | 4/2006 |
| WO | WO-82/01047 A1 | 4/1982 |
| WO | WO-91/17271 A1 | 11/1991 |
| WO | WO-1995/0004524 A1 | 2/1995 |
| WO | WO-1995/0007354 A1 | 3/1995 |
| WO | WO-1995/0025124 A1 | 9/1995 |
| WO | WO-1996/0033219 A1 | 10/1996 |
| WO | WO-1996/0040243 A1 | 12/1996 |
| WO | WO-1999/0033522 A2 | 7/1999 |
| WO | WO-2000/0016746 A2 | 3/2000 |
| WO | WO-2003/0022879 A2 | 3/2003 |
| WO | WO-2003/0059953 A2 | 7/2003 |
| WO | WO-2004/0006847 A2 | 1/2004 |
| WO | WO-2004/0087738 A2 | 10/2004 |
| WO | WO-2005/021574 A2 | 3/2005 |
| WO | WO-2006/0110831 A2 | 10/2006 |
| WO | WO-2008/0033500 A2 | 3/2008 |
| WO | WO-2008/0127651 A1 | 10/2008 |
| WO | WO-2009/0111304 A2 | 9/2009 |
| WO | WO-2010/0042942 A2 | 4/2010 |
| WO | WO-2010/045613 A1 | 4/2010 |
| WO | WO-2010/114628 A2 | 10/2010 |
| WO | WO-2010/0114629 A2 | 10/2010 |
| WO | WO-2012/0139097 A2 | 10/2012 |

OTHER PUBLICATIONS

Verkoczy, L., et al., 2013, Induction of HIV-1 broad neutralizing antibodies in 2F5 knock-in mice: selection against membrane proximal external region-associated autoreactivity limits T-dependent responses, J. Immunol. 191:2538-2550.*

Zwick, M. B., 2005, The membrane-proximal external region of HIV-1 gp41: a vaccine target worth exploring, AIDS 19:1725-1737.*

Kuiken, C., et al., eds., 2012, HIV Sequence Compendium, published by Theoretical Biology and Biophysics Group, Los Alamos National Laboratory, NM, LA-UR 12-24653, pp. 358-371.*

Aguilar, L., et al., "Phospholipid Membranes Form Specific Nonbilayer Molecular Arrangements That Are Antigenic", The Journal of Biological Chemistry, vol. 274, No. 36, pp. 25193-25196 (Sep. 3, 1999).

Alam, S. M. et al., "An Inducible HIV Type 1 gp41 HR-2 Peptide-Binding Site on HIV Type 1 Envelope gp120," AIDS Research and Human Retroviruses, vol. 20, No. 8, pp. 836-845 (Aug. 2004).

Alam, S. M. et al., "Human Immunodeficiency Virus Type 1 gp41 Antibodies That Mask Membrane Proximal Region Epitopes: Antibody Binding Kinetics, Induction, and Potential for Regulation in Acute Infection," Journal of Virology, vol. 82, No. 1, pp. 115-125 (Jan. 2008).

Alam, S. M., et al., "Role of HIV membrane in neutralization by two broadly neutralizing antibodies", PNAS, vol. 106, No. 48, pp. 20234-20239 (Dec. 1, 2009).

Alam, S. M., et al., "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes", The Journal of Immunology, vol. 178, No. 7, pp. 4424-4435, Author Manuscript—25 pages (Apr. 1, 2007).

Alam, S. M., et al., "Differential reactivity of germ line allelic variants of a broadly neutralizing HIV-1 antibody to a gp41 fusion intermediate conformation," J. Virol., vol. 85, No. 22, pp. 11725-11731 (Nov. 2011).

Alving, C. R. et al., "HIV-1, Lipid Rafts, and Antibodies to Liposomes: Implications for Anti-Viral-Neutralizing Antibodies (Review)," Molecular Membrane Biology, vol. 23, No. 6, pp. 453-466 (Nov.-Dec. 2006).

Alving, Carl R., "Immunologic aspects of liposomes: presentation and processing of liposomal protein and phospholipid antigens," Biochimica et Biophysica Acta, vol. 1113, No. 3-4, pp. 307-322 (Dec. 11, 1992).

Alving, C. R., et al., "Chapter 21: Preparation and Use of Liposomes in Immunological Studies," Liposome Technology, 2nd Edition, vol. III, Interactions of Liposomes with the Biological Milieu, pp. 317-343, 29 pages (1993).

Armbruster, C., et al., "Passive immunization with the anti-HIV-1 human monoclonal antibody (hMab) 4E10 and the hMab combination 4E10/2F5/2G12", Journal of Antimicrobial Chemotherapy, vol. 54, pp. 915-920 (Sep. 29, 2004).

Barbato, G., et al., "Structural analysis of the epitope of the anti-HIV antibody 2F5 sheds light into its mechanism of neutralization and HIV fusion," J. Mol. Biol., vol. 330, pp. 1101-1115 (2003).

Barthel, H. R. and Wallace, D. J., "False-Positive Human Immunodeficiency Virus Testing in Patients With Lupus Erythematosus", Seminars in Arthritis and Rheumatism, vol. 23, No. 1, pp. 1-7 (Aug. 1993).

Bate, et al., "Phospholipids coupled to a carrier induce IgG antibody that blocks tumour necrosis factor induction by toxic malaria antigens", Immunology, vol. 79, pp. 138-145 (1993).

Binley, J. M., et al., "Comprehensive Cross-Clade Neutralization Analysis of a Panel of Anti-Human Immunodeficiency Virus Type 1 Monoclonal Antibodies," J. Virol., vol. 78, No. 23, pp. 13232-13252 (Dec. 2004).

Blattner, W. A., et al., "Rapid Clearance of Virus after Acute HIV-1 Infection: Correlates of Risk of AIDS," J. Infect. Dis., vol. 189, pp. 1793-1801 (May 15, 2004).

(56) References Cited

OTHER PUBLICATIONS

Brown, B. K., et al., "Monoclonal Antibodies to Phosphatidylinositol Phosphate Neutralize Human Immunodeficiency Virus Type 1: Role of Phosphate-Binding Subsites", Journal of Virology, vol. 81, No. 4, pp. 2087-2091 (Feb. 2007).
Burton, D. R., et al., "A large array of human monoclonal antibodies to type 1 human immunodeficiency virus from combinatorial libraries of asymptomatic seropositive individuals," Proc. Natl. Acad. Sci. USA, vol. 88, pp. 10134-10137 (Nov. 1991).
Callahan, M. K., et al., "Phosphatidylserine on HIV Envelope Is a Cofactor for Infection of Monocytic Cells", The Journal of Immunology, vol. 170, pp. 4840-4845 (2003).
Cardoso, R. M., et al., "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).
Chang, J.-S., et al., "Immunogenicity of synthetic HIV-1 V3 loop peptides by MPL adjuvanted pH-sensitive liposomes", Vaccine, vol. 17, pp. 1540-1548 (1999).
Chen, X. et al., "Novel recombinant engineered gp41 N-terminal heptad repeat trimers and their potential as anti-HIV-1 therapeutics or microbicides," The Journal of Biological Chemistry, vol. 285, No. 33, pp. 25506-25515 (Aug. 13, 2010) (23 pages).
Chukwuocha, R. U., et al., "Molecular and genetic characterizations of five pathogenic and two non-pathogenic monoclonal antiphospholipid antibodies", Molecular Immunology, vol. 39, pp. 299-311 (2002).
Coeffier, E. et al., "Antigenicity and immunogenicity of the HIV-1 gp41 epitope ELDKWA inserted into permissive sites of the MalE protein," Vaccine, vol. 19, No. 7-8, pp. 684-693 (Nov. 22, 2000).
Cornet, B., et al., "Virosomes reconstituted from human immunodeficiency virus proteins and lipids", Biochem. Biophys. Res. Comm., vol. 167, No. 1, pp. 222-231 (Feb. 28, 1990).
Creaven, P. J., et al, "Initial Clinical Trial of Muramyl Tripeptide Derivative (MTP-PE) Encapsulated in Liposomes: An Interim Report", Abstract, Accession No. 90657770 CancerLit (Jan. 1990) (1 page).
Darland-Ransom et al, "Role of C. elegans TAT-1 Protein in Maintaining Plasma Membrane Phosphatidylserine Asymmetry", Science, vol. 320, pp. 528-531 (Apr. 25, 2008).
Del Papa et al., "Human beta2-Glycoprotein I Binds to Endothelial Cells Through a Cluster of Lysine Residues That Are Critical for anionic Phospholipid Binding and Offers Epitopes for anti-beta2-Glycoprotein I Antibodies", The Journal of Immunology, vol. 160, pp. 5572-5578 (1998).
Dennison et al., "Stable docking of neutralizing human immunodeficiency virus type 1 gp41 membrane-proximal external region monoclonal antibodies 2F5 and 4E10 is dependent on the membrane immersion depth of their epitope regions," Journal of Virology, vol. 83, No. 19, pp. 10211-10223 (Oct. 2009).
Dennison, S. M., et al., "Induction of Antibodies in Rhesus Macaques That Recognize a Fusion-Intermediate Conformation of HIV-1 gp41," Plos One, vol. 6, Issue 11, e27824, pp. 1-14 (Nov. 2011).
Dhillon, A. K., et al., "Dissecting the Neutralizing Antibody Specificities of Broadly Neutralizing Sera from Huma Immunodeficiency Virus Type 1-Infected Donors," J. Virol., vol. 81, No. 12, pp. 6548-6562 (Jun. 2007).
Doyle, C. M., et al., "Consequences of receptor editing at the λ locus: Multireactivity and light chain secretion," PNAS, vol. 103, No. 30, pp. 11264-11269 (Jul. 25, 2006).
Extended European Search Report issued by the European Patent Office for European Application No. 10759166.1 dated Apr. 20, 2015 (6 pages).
Fairn, G. D. and Grinstein, S., "A One-Sided Signal", Science, vol. 320, pp. 458-460 (Apr. 25, 2008).
Ferrantelli, F., et al., "Complete Protection of Neonatal Rhesus Macaques against Oral Exposure to Pathogenic Simian-Human Immunodeficiency Virus by Human Anti-HIV Monoclonal Antibodies," J. Infect. Dis., vol. 189, pp. 2167-2173 (Jun. 15, 2004).
Frey, G. et al., "A fusion-intermediate state of HIV-1 gp41 targeted by broadly neutralizing antibodies," PNAS, vol. 105, No. 10, pp. 3739-3744 (Mar. 11, 2008).

Frisch et al., "Synthetic Peptide-Based Highly Immunogenic Liposomal Constructs", Methods in Enzymology, vol. 373, pp. 51-73 (2003).
Geffin, R., et al., "A longitudinal assessment of autologous neutralizing antibodies in children perinatally infected with human immunodeficiency virus type 1," Virology, vol. 310, pp. 207-215 (2003).
Gómara, M. J., et al., "Hexapeptides that interfere with HIV-1 fusion peptide activity in liposomes block GP41-mediated membrane fusion", FEBS Letters, vol. 580, No. 11, pp. 2561-2566 (May 15, 2006).
Gray, E. S., et al., "Neutralizing Antibody Responses in Acute Human Immunodeficiency Virus Type 1 Subtype C Infection," J. Virol., vol. 81, No. 12, pp. 6187-6196 (Jun. 2007).
Guenaga, J., et al., "Heterologous epitope-scaffold prime:boosting immuno-focuses B cell responses to the HIV-1 gp41 2F5 neutralization determinant," PLoS One, vol. 6, Issue 1, e16074, pp. 1-12 (Jan. 2011).
Hammel, M., et al., "Mechanism of the Interaction of beta2-Glycoprotein I with Negatively Charged Phospholipid Membranes", Biochemistry, vol. 40, pp. 14173-14181 (2001).
Haynes, B. F. et al., "Cardiolipin polyspecific autoreactivity in two broadly neutralizing HIV-1 antibodies," Science, vol. 308, No. 5730, pp. 1906-1908 (Jun. 24, 2005).
Herlands, R. A., et al., "T Cell-Independent and Toll-like Receptor-Dependent Antigen-Driven Activation of Autoreactive B Cells," Immunity, vol. 29, No. 2, pp. 249-260, Author Manuscript—26 pages (Aug. 15, 2008).
Hinz, A. et al., "Characterization of a trimeric MPER containing HIV-1 gp41 antigen," Virology, vol. 390, No. 2, pp. 221-227 (Aug. 1, 2009).
Ho, J. et al., "Conformational constraints imposed on a panneutralizing HIV-1 antibody epitope result in increased antigenicity but not neutralizing response," Vaccine, vol. 23, pp. 1559-1573 (2005).
Huang, X., et al., "A Monoclonal Antibody that Binds Anionic Phospholipids on Tumor Blood Vessels Enhances the Antitumor Effect of Docetaxel on Human Breast Tumors in Mice", Cancer Res., vol. 65, No. 10, pp. 4408-4416 (May 15, 2005).
Huang, X., et al., "Anti-Tumor Effects and Lack of Side Effects in Mice of Immunotoxin Directed Against Human and Mouse Prostate-Specific Membrane Antigen", The Prostate, vol. 61, pp. 1-11 (2004).
Huarte, N., et al., "Recognition of membrane-bound fusion-peptide/MPER complexes by the HIV-1 neutralizing 2F5 antibody: implications for anti-2F5 immunogenicity," PLoS One, vol. 7, Issue 12, e52740, pp. 1-13 (Dec. 2012).
Huarte, N., et al., "The broadly neutralizing anti-human immunodeficiency virus type 1 4E10 monoclonal antibody is better adapted to membrane-bound epitope recognition and blocking than 2F5", Journal of Virology, vol. 82, No. 18, p. 8986-8996, Sep. 2008, 4 pages of supplemental material (15 pages total).
Hunt, J. and Krilis, S., "The Fifth Domain of beta2-Glycoprotein I Contains a Phospholipid Binding Site (Cys281-Cys288) and a Region Recognized by Anticardiolipin antibodies", Journal of Immunology, vol. 152, pp. 653-659 (1994).
Ichikawa, H. T., et al., "Activation of APCs Through CD40 or Troll-like Receptor 9 Overcomes Tolerance and Precipitates Autoimmune Disease", The Journal of Immunology, vol. 169, pp. 2781-2787 (2002).
International Preliminary Report on Patentability issued by the International Bureau of WIPO for International Application No. PCT/US2006/013684 dated Apr. 28, 2009 (4 pages).
International Preliminary Report on Patentability issued by the International Bureau of WIPO for International Application No. PCT/US2008/004709 dated Oct. 13, 2009 (5 pages).
International Preliminary Report on Patentability issued by the International Bureau of WIPO for International Application No. PCT/US2012/032717 dated Oct. 8, 2013 (5 pages).
International Search Report and Written Opinion issued by the Korean Intellectual Property Office as International Searching Authority for International Application No. PCT/US2012/032717 dated Oct. 29, 2012 (8 pages).

(56) References Cited

OTHER PUBLICATIONS

International Search Report and Written Opinion issued by the Korean Intellectual Property Office as International Searching Authority for International Application No. PCT/US2014/058032 dated Jan. 12, 2015 (11 pages).
International Search Report and Written Opinion issued by the U.S. Patent and Trademark Office as International Searching Authority for International Application No. PCT/US06/13684 dated Jul. 31, 2008 (4 pages).
International Search Report and Written Opinion issued by the U.S. Patent and Trademark Office for International Application No. PCT/US2008/04709 dated Sep. 17, 2008 (7 pages).
International Search Report and Written Opinion issued by the Korean Intellectual Property and Trademark Office as International Searching Authority for International Application No. PCT/US2010/001017 dated Jan. 18, 2011 (11 pages).
Japanese Office Action issued by the Japan Patent Office for Japanese Application No. 2012-503432 dated Jun. 16, 2014 (4 pages—English translation only).
Jiang, Z.-H. And Rao, K. R., "Synthetic vaccines: the role of adjuvants in immune targeting", Current Medicinal Chemistry, vol. 10, No. 15, pp. 1423-1439 (Aug. 2003)—Medline, Abstract, PMID: 12871139 (1 page).
Li, J., et al., "The interaction between the membrane-proximal external region and the N-trimer region of HIV-1 gp41: Involvement in viral fusion," Chinese Science Bulletin, vol. 54, No. 10, pp. 1707-1712 (May 2009).
Joyce, J. G. et al., "Enhancement of alpha -helicity in the HIV-1 inhibitory peptide DP178 leads to an increased affinity for human monoclonal antibody 2F5 but does not elicit neutralizing responses in vitro. Implications for vaccine design," J. Biol. Chem., vol. 277, No. 48, pp. 45811-45820, 12 pages (Nov. 29, 2002).
Kim, M., et al., "Antibody mechanics on a membrane-bound HIV segment essential for GP41-targeted viral neutralization," Nat. Struct. Mol. Biol., vol. 18, No. 11, pp. 1235-1243, Author Manuscript—22 pages (Nov. 1, 2012).
Kim, M., et al., "Immunogenicity of membrane-bound HIV-1 gp41 membrane-proximal external region (MPER) segments is dominated by residue accessibility and modulated by stereochemistry," J. Biol. Chem., vol. 288, No. 44, pp. 31888-31901 (Nov. 1, 2013).
Kim, M., et al., "Immunogenicity of recombinant human immunodeficiency virus type 1-like particles expressing gp41 derivatives in a pre-fusion state," Vaccine, vol. 25, No. 27, pp. 5102-5114, Author's Manuscript—24 pages (Jun. 28, 2007).
Lenz, O., et al, "Trimeric membrane-anchored gp41 inhibits HIV membrane fusion", J. Biol. Chem., vol. 280, No. 6, pp. 4095-4101 (Feb. 11, 2005).
Letvin, N. L. and Walker, B. D., "Immunopathogenesis and immunotherapy in AIDS virus infections", Nature Medicine, vol. 9, No. 7, pp. 861-866 (Jul. 2003).
Li, M., et al., "Human Immunodeficiency Virus Type 1 env Clones from Acute and Early Subtype B Infections for Standardized Assessments of Vaccine-Elicited Neutralizing Antibodies," J. Virol., vol. 79, No. 16, pp. 10108-10125 (Aug. 2005).
Li, Y., et al., "Autoreactive B Cells in the Marginal Zone that Express Dual Receptors," J. Exp. Med., vol. 195, No. 2, pp. 181-188 (Jan. 21, 2002).
Liao, H.-X., et al., "A Group M Consensus Envelope Glyoprotein Induces Antibodies That Neutralize Subsets of Subtype B and C HIV-1 Primary Viruses", Virology, vol. 353, No. 2, pp. 268-282 (2006).
Lin, W.-S., et al., "Some antiphospholipid antibodies recognize conformational epitopes shared by β2GPI and the homologous catalytic domains of several serine proteases," Arth. Rheum., vol. 56, No. 5, pp. 1638-1647, Author Manuscript—18 pages (May 2007).
Lopez, P. H. H. and Schnaar, R. L., "Determination of Glycolipid-Protein Interaction Specificity", Methods in Enzymology, vol. 417, pp. 205-220, Author Manuscript—14 pages (2006).
Lorizate, M., et al., "Recognition and Blocking of HIV-1 gp41 Pre-transmembrane Sequence by Monoclonal 4E10 Antibody in a Raft-like Membrane Environment", The Journal of Biological Chemistry, vol. 281, No. 51, pp. 39598-39606 (Dec. 22, 2006).
Lu et al., "Identification of Polyclonal and Monoclonal Antibodies Against Tissue Plasminogen Activator in the Antiphospholipid Syndrome", Arthritis & Rheumatism, vol. 52, No. 12, pp. 4018-4027 (Dec. 2005).
Lu, J., et al., "Relative Replicative Fitness of Human Immunodeficiency Virus Type 1 Mutants Resistant to Enfuvirtide (T-20)," J. Virol., vol. 78, No. 9, pp. 4628-4637 (May 2004).
Luo et al., "Induction of neutralizing antibody against human immunodeficiency virus type 1 (HIV-1) by immunization with gp41 membrane-proximal external region (MPER) fused with porcine endogenous retrovirus (PERV) p15e fragment", Vaccine (Netherlands), vol. 24, No. 4, pp. 435-442 (Jan. 23, 2006)—Medline, Abstract, PMID: 16143433 (1 page).
Luster, T. A., et al., "Plasma Protein beta-2-Glycoprotein 1 Mediates Interaction between the Anti-tumoro Monoclonal Antibody 3G4 and Anionic Phospholipids on Endothelial Cells", The Journal of Biological Chemistry, vol. 281, No. 40, pp. 29863-29871 (Oct. 6, 2006).
Ma, B.-J., et al., "Envelope Deglycosylation Enhances Antigenicity of HIV-1 gp41 Epitopes for Both Broad Neutralizing Antibodies and Their Unmutated Ancestor Antibodies," PLoS Pathogens, vol. 7, No. 9, e1002200, pp. 1-16 (Sep. 2011).
Maksyutov, A. Z., et al., "Exclusion of HIV epitopes shared with human proteins in prerequisite for designing safer AIDS vaccines", Journal of Clinical Virology, vol. 749, pp. 1-13 (2004).
Marshak-Rothstein, A. and Rifkin, I. R., "Immunologically Active Autoantigens: The Role of Toll-Like Receptors in the Development of Chronic Inflammatory Disease," Annu. Rev. Immunol., vol. 25, pp. 419-441, 26 pages (2007).
Mascola, J. R., et al., "Protection of macaques against vaginal transmission of a pathogenic HIV-1/SIV chimeric virus by passive infusion of neutralizing antibodies," Nat. Med., vol. 6, No. 2, pp. 207-210 (Feb. 2000).
McGaughey, G. B., et al., "HIV-1 Vaccine Development: Constrained Peptide Immunogens Show Improved Binding to the Anti-HIV-1 gp41 MAb," Biochemistry, vol. 42, pp. 3214-3223 (2003).
Mehandru, S. et al., "Neutralization Profiles of Newly Transmitted Human Immunodeficiency Virus Type 1 by Monoclonal Antibodies 2G12, 2F5, and 4E10," Journal of Virology, vol. 78, No. 24, pp. 14039-14042 (Dec. 2004).
Mercer, J. and Helenius, A., "Vaccinia Virus Uses Macropinocytosis and Apoptotic Mimicry to Enter Host Cells", Science, vol. 320, pp. 531-535 (Apr. 25, 2008).
Montefiori, David C., "Neutralizing antibodies take a swipe at HIV in vivo", Nature Medicine, vol. 11, No. 6, pp. 593-594 (Jun. 2005).
Moog, C., et al., "Autologous and Heterologous Neutralizing Antibody Responses following Initial Seroconversion in Human Immunodeficiency Virus Type 1-Infected Individuals," J. Virol., vol. 71 No. 5, pp. 3734-3741 (May 1997).
Muster et al., "Cross-Neutralizing Activity against Divergent Human Immunodeficiency Virus Type 1 Isolates Induced by the gp41 Sequence ELDKWAS", Journal of Virology, vol. 68, No. 6, pp. 4031-4034 (Jun. 1994).
Nabel, Gary J., "Close to the Edge: Neutralizing the HIV-1 Envelope", Science, vol. 308, pp. 1878-1879 (Jun. 24, 2005).
Nelson, J. D. et al., "An affinity-enhanced neutralizing antibody against the membrane-proximal external region of human immunodeficiency virus type 1 gp41 recognizes an epitope between those of 2F5 and 4E10," J. Virol., vol. 81, No. 8, pp. 4033-4043 (Apr. 2007).
Ofek et al., "Structure and Mechanistic Analysis of the Anti-Human Immunodeficiency Virus Type 1 Antibody 2F5 in Complex with Its gp41 Epitope", Journal of Virology, vol. 78, No. 19, pp. 10724-10737 (Oct. 2004).
Ofek, G., et al., "Elicitation of structure-specific antibodies by epitope scaffolds," PNAS, vol. 107, No. 42, pp. 17880-17887 (Oct. 19, 2010).

(56) References Cited

OTHER PUBLICATIONS

Ou, W. et al., "Effect of epitope position on neutralization by anti-human immunodeficiency virus monoclonal antibody 2F5," J. Virol., vol. 80, No. 5, pp. 2539-2547 (Mar. 2006).
Perelson, A. S., et al, "HIV-1 Dynamics in Vivo: Virion Clearance Rate, Infected Cell Life-Span, and Viral Generation Time", Science, vol. 271, pp. 1582-1586 (Mar. 15, 1996).
Petrovas et al., "Anti-phospholipid Antibodies in HIV Infection and SLE With or Without Anti-phospholipid Syndrome: Comparisons of Phospholipid Specificity, Avidity and Reactivity with beta2-GPI", Journal of Autoimmunity, vol. 13, pp. 347-355 (Nov. 1999).
Pinto, L. A., et al., "Panel of Anti-gp120 Monoclonal Antibodies Reacts with Same Nuclear Proteins in Uninfected Cells as Those Recognized by Autoantibodies from Patients with Systemic Lupus Erythematsous", AIDS Research and Human Retroviruses, vol. 10, No. 7, pp. 823-828 (1994).
Putscher, M., et al., "Restricted antigenic variability of the epitope recognized by the neutralizing gp41 antibody 2F5," AIDS, vol. 10, No. 6, pp. 587-593 (Jun. 1996).
Ran, S., et al., "Antitumor Effects of a Monoclonal Antibody that Binds Anionic Phospholipids on the Surface of Tumor Blood Vessels in Mice", Clinical Cancer Research, vol. 11, pp. 1551-1562 (Feb. 15, 2005).
Ran et al., "Increased Exposure of Anionic Phospholipids on the Surface of Tumor Blood Vessels", Cancer Research, vol. 62, pp. 6132-6140 (Nov. 1, 2002).
Rao, M., et al., "Immunostimulatory CpG motifs induce CTL responses to HIV type I oligomeric gp140 envelope protein," Immunology and Cell Biology, vol. 82, pp. 523-530 (2004).
Rauch, J. and Janoff, A. S., "Phospholipid in the hexagonal II phase is immunogenic: Evidence for immunoregonition of nonbilayer lipid phases in vivo", Proc. Natl. Acad. Sci. USA, vol. 87, pp. 4112-4114 (Jun. 1990).
Reardon, P. N. et al., "Structure of an HIV-1-neutralizing antibody target, the lipid-bound gp41 envelope membrane proximal region trimer," PNAS, vol. 111, No. 4, pp. 1391-1396, 10 pages (Jan. 28, 2014).
Reeves, J. D., et al., "Enfuvirtide Resistance Mutations: Impact on Human Immunodeficiency Virus Envelope Function, Entry Inhibitor Sensitivity, and Virus Neutralization," J. Virol., vol. 79, No. 8, pp. 4991-4999 (Apr. 2005).
Richards, R. L., et al., "Liposomes Containing Lipid a Serve as an Adjuvant for Induction of Antibody and Cytotoxic T-Cell Responses against RTS,S Malaria Antigen," Infection and Immunity, vol. 66, No. 6, pp. 2859-2865 (Jun. 1998).
Richman, D. D., et al., "Rapid evolution of the neutralizing antibody response to HIV type 1 infection," Proc. Natl. Acad. Sci. USA, vol. 100, No. 7, pp. 4144-4149 (Apr. 1, 2003).
Sakaue et al., "HIV Mucosal Vaccine: Nasal Immunization with gp 160-Encapsualted Hemagglutinating Virus of Japan-Lipsome Induces Antigen-Specific CTLs and Neutralizing Antibody Responses", The Journal of Immunology, vol. 170, pp. 495-502 (Jan. 1, 2003).
Sanchez, P. J. et al., "Combined TLR/CD40 Stimulation Mediates Potent Cellular Immunity by Regulating Dendritic Cell Expression of CD70 In Vivo," the Journal of Immunology, vol. 178, No. 3, pp. 1564-1572 (Feb. 1, 2007).
Scherer, E. M., et al, "Difficulties in eliciting broadly neutralizing anti-Hiv antibodies are not explained by cardiopin autoreactivity", AIDS, vol. 21, No. 16, pp. 2131-2139 (Oct. 18, 2007)—Medline, Abstract, PMID: 18090039 (1 page).
Schnaar, Ronald L., "Isolation of Glycosphingolipids", Chapter 22, Methods in Enzymology, vol. 230, pp. 348-370 (1994).
Serrano et al., "Structure and Immunogenicity of a Peptide Vaccine Including the Complete HIV-1 gp41 2F5 Epitope. Implications for Antibody Recognition Mechanism and Immunogen Design," J. Biol. Chem., vol. 289, No. 10, pp. 6565-6580 (Mar. 7, 2014).
Shen, X. et al., "In vivo gp41 antibodies targeting the 2F5 monoclonal antibody epitope mediate human immunodeficiency virus type 1 neutralization breadth," J. Virol., vol. 83, No. 8, pp. 3617-3625 (Apr. 2009).
Shen, X. et al., "Prolonged exposure of the HIV-1 gp41 membrane proximal region with L669S substitution," PNAS, vol. 107, No. 13, pp. 5972-5977 (Mar. 30, 2010).
Shlomchik, Mark J., "Sites and Stages of Autoreactive B Cell Activation and Regulation," Immunity, vol. 28, pp. 18-28 (Jan. 2008).
Sims, G. P., et al., "Identification and characterization of circulating human transitional B cells," Blood, vol. 105, No. 11, pp. 4390-4398, 23 pages in total, (Jun. 1, 2005).
Singh, H., et al, "Reactivity profiles of broadly neutralizing anti-HIV-1 antibodies are distinct from those of pathogenic autoantibodies", AIDS, vol. 25, No. 10, pp. 1247-1257, Author Manuscript—19 pages (Jun. 19, 2011).
Stiegler, G. and Katinger, H., "Therapeutic potential of neutralizing antibodies in the treatment of HIV-1 infection", Journal of Antimicrobial Chemotherapy, vol. 51, pp. 757-759 (2003).
Stults, C. L. M., et al., "Glycosphingolipids: Structure, biological Source, and Properties", Chapter 14, Methods in Enzymology, vol. 179, pp. 167-214 (1989).
Sullards, M. C., et al., "Structure-Specific Quantitative Methods for Analysis of Sphingolipids by Liquid Chromatography-Tandem Mass Spectrometry: "Inside-Out" Sphingolipidomics", Chapter Four, Methods in Enzymology, vol. 432, pp. 83-115 (2007).
Supplementary European Search Report issued by the European Patent Office for Application No. EP 06740904.5 dated Sep. 2, 2010 (14 pages).
Supplementary European Search Report issued by the European Patent Office for Application No. 08742782.9 dated May 19, 2011 (11 pages).
Supplementary European Search Report issued by the European Patent Office for Application No. EP 12768170.8 dated Aug. 20, 2014 (5 pages).
Thorpe, Philip E., "Vascular Targeting Agents as Cancer Therapeutics", Clinical Cancer Research, vol. 10, pp. 415-427 (Jan. 15, 2004).
Uccellini, M. B., et al., "Autoreactive B Cells Discriminate CpG-rich and CpG-poor DNA and This Response is Modulated by IFN-α1," J. Immunol., vol. 181, No. 9, pp. 5875-5884, Author Manuscript—21 pages (Nov. 1, 2008).
Vcelar, B., et al. "Reassessment of autoreactivity of the broadly neutralizing HIV antibodies 4E10 and 2F5 and retrospective analysis of clinical safety data", AIDS, vol. 21, No. 16, pp. 2161-2170 (Oct. 18, 2007)—Abstract only—2 pages.
Vega-Ostertag, M., et al., "A human monoclonal antiprothrombin antibody is thrombogenic in vivo and upregulates expression of tissue factor and E-selectin on endothelial cells", British Journal of Haematology, vol. 135, pp. 214-219 (2006).
Verkoczy, et al., "Induction of HIV-1 broad neutralizing antibodies in 2F5 knock-in mice: selection against membrane proximal external region-associated autoreactivity limits T-dependent responses," The Journal of Immunology, vol. 191, No. 5, pp. 2538-2550 (Aug. 5, 2013).
Vogel, F. R., "The role of adjuvants in retroviral vaccines", International Journal of Immunopharmacology, vol. 17, No. 2, pp. 85-90 (Feb. 1995)—Medline, Abstract, PMID: 7657411 (1 page).
Wang, Y. and Krieg, A. M., "Induction of autoantibody production but not autoimmune disease in HEL transgenic mice vaccinated with HEL in combination with CpG or control oligodeoxynucleotides", Vaccine, vol. 22, pp. 2641-2650 (2004).
Wassef, N. M., et al., "Liposomes as Carriers for Vaccines," Immunomethods, vol. 4, pp. 217-222 (1994).
Wei, X., et al., "Antibody neutralization and escape by HIV-1," Nature, vol. 422, pp. 307-312 (Mar. 20, 2003).
Wei et al, "Viral dynamics in human immunodeficiency virus type 1 infection", Nature, vol. 373, pp. 117-122 (Jan. 12, 1995).
White et al., "Antibody and cytotoxic T-lymphocyte responses to a single liposome-associated peptide antigen", Vaccine, vol. 13, No. 12, pp. 1111-1122 (Aug. 1995)—Medline, Abstract, PMID: 7491819 (1 page).
Witsch, E. J., et al., "Light chain editing generates polyreactive antibodies in chronic graft-versus-host reaction," J. Exp. Med., vol. 203, No. 7, pp. 1761-1772 (Jul. 10, 2006).

(56) References Cited

OTHER PUBLICATIONS

Wu, H., et al., "Modeling and Estimation of Replication Fitness of Human Immunodeficiency Virus Type 1 In Vitro Experiments by Using a Growth Competition Assay," J. Virol., vol. 80, No. 5, pp. 2380-2389 (Mar. 2006).

Zhang, G. et al., "Neutralization of HIV-1 primary isolate by ELDKWA-specific murine monoclonal antibodies," Immunobiology, vol. 210, No. 9, pp. 639-645 (2005).

Zhang, M. Y. et al., "Cross-Reactive Human Immunodeficiency Virus Type 1-Neutralizing Human Monoclonal Antibody That Recognizes a Novel Conformational Epitope on gp41 and Lacks Reactivity against Self-Antigens," Journal of Virology, vol. 82, No. 14, pp. 6869-6879 (Jul. 2008).

Zhu, M., et al., "Characterization of IgG monoclonal anti-cardiolipin/anti-beta2GP1 antibodies from two patients with antiphospholipid syndrome reveals three species of antibodies", British Journal of Haematology, vol. 105, pp. 102-109 (1999).

Ziegler, J. L. and Stites, D. P., "Hypothesis: AIDS Is an Autoimmune Disease Directed at the Immune System and Triggered by a Limphotropic Retrovrius", Clinical Immunology and Immunopathology, vol. 41, pp. 305-313 (1986).

Zwick et al., "Anti-Human Immunodeficiency Virus Type 1 (HIV-1) Antibodies 2F5 and 4E10 Require Surprisingly Few Crucial Residues in the Membrane-Proximal External Region of Glycoprotein gp41 to Neutralize HIV-1", Journal of Virology, vol. 79, No. 2, pp. 1252-1261 (Jan. 2005).

Zwick et al., "The Long Third Complementarity-Determining Region of the Heavy Chain is Important in the Activity of the Broadly Neutralizing Anti-Human Immunodeficiency Virus Type 1 Antibody 2F5", Journal of Virology, vol. 78, No. 6, pp. 3155-3161 (Mar. 2004).

Zwick, M. B. et al., "Broadly neutralizing antibodies targeted to the membrane-proximal external region of human immunodeficiency virus type 1 glycoprotein gp41," J. Virol., vol. 75, No. 22, pp. 10892-10905 (Nov. 2001).

Zwick, Michael B., "The membrane-proximal external region of HIV-1 gp41: a vaccine target worth exploring," AIDS, vol. 19, pp. 1725-1737 (2005).

Williams, L.D., et al., Potent and broad HIV-neutralizing antibodies in memory B cells and plasma, Science Immunology, vol. 2, eaal2200, pp. 1-15 (Jan. 27, 2017).

"HIV Sequence Compendium 2011," Published by Theoretical Biology and Biophysics, Group T-6, Mail Stop K710, Los Alamos National Laboratory, Los Alamos, New Mexico 87545 U.S.A., 442 total pages including Table of Contents, Preface, Chapters I-VII (2011).

Huber, M. and Trkola, A., "Humoral immunity to HIV-1: neutralization and beyond," Journal of Internal Medicine, vol. 262, pp. 5-25 (2007).

Scherer, E. M., et al, "Difficulties in eliciting broadly neutralizing anti-HIV antibodies are not explained by cardiolipin autoreactivity", AIDS, vol. 21, No. 16, pp. 2131-2139 (Oct. 18, 2007).

Burton, D. R., et al., "Efficient Neutralization of Primary Isolates of HIV-1 by a Recombinant Human Monoclonal Antibody", Science, vol. 266, pp. 1024-1027 (1994).

Burton, D. R., et al., "HIV vaccine design and the neutralizing antibody problem", Nature Immunol. vol. 5, No. 3, pp. 233-236 (2004).

Choe, H. et al., "Tyrosine Sulfation of Human Antibodies Contributes to Recognition of the CCR5 Binding Region of HIV-1 gp120", Cell, vol. 114, No. 2, pp. 161-170 (2003).

Derdeyn, C. A., et al., "Sensitivity of Human Immunodeficiency Virus Type 1 to the Fusion Inhibitor T-20 Is Modulated by Coreceptor Specificity Defined by the V3 Loop of gp120", Journal of Virology, vol. 74, pp. 8358-8367 (2000).

DeRue, G.J., et al., "Fetal loss in systemic lupus: association with anticardiolipin antibodies", J. Obest. Gynecol. Neonatal Nurs., vol. 5, pp. 207-209 (1985).

Fox, R. A. and Isenberg, D. A., "Human Immunodeficiency Virus Infection in Systemic Lupus Erythematosus," Arth. Rheum., vol. 40, pp. 1168-1172 (1997).

Gregoriadis, Gregory, "Liposome Technology: vol. III, Interactions of Liposomes with the Biological Milieu," Chapter 21, pp. 317-343 (1993).

Grunewald, T., et al., "Anti-phospholipid antibodies and CD5+ B cells in HIV infection", Clin. Exp. Immunol., vol. 115, pp. 464-471 (1999).

Harris, E. N., et al., "Evaluation of the anti-cardiolipin antibody test: report of an international workshop held Apr. 4, 1986", Clin. Exp. Immunol., vol. 68, p. 215-222 (1987).

Hemmi, H. et al., "A Toll-like receptor recognizes bacterial DNA," Nature, vol. 408, No. 6813, pp. 740-745 (Dec. 7, 2000) (includes erratum which was published in Nature, vol. 409, p. 646 and dated Feb. 1, 2001).

Hohman, V. S., et al., "Genomic clone for sandbar shark $\lambda$ light chain: Generation of diversity in the absence of gene rearrangement", Proc. Natl. Acad. Sci. USA, vol. 90, pp. 9882-9886 (1993).

Huse, W. D., et al., "Generation of a large combinatorial library of the immunoglobulin repertoire in phage lambda," Science, vol. 246, pp. 1275-1281, 8 total pages (1989).

Kunert, R. E., et al., "Anti-idiotypic antibody Ab2/3H6 mimics the epitope of the neutralizing anti-HIV-1 monoclonal antibody 2F5," AIDS, vol. 16, Issue 4, pp. 667-668, 4 pages (Mar. 8, 2002).

Kunert, R., et al., "Characterization of Molecular Features, Antigen-Binding, and in Vitro Properties of IgG and IgM Variants of 4E10, an Anti-HIV Type 1 Neutralizing Monoclonal Antibody," AIDS Res. Hum. Retroviruses, vol. 20, No. 7, pp. 755-762 (2004).

Liao, H.-X., et al., "Immunogenicity of Constrained Monoclonal Antibody A32-Human Immunodeficiency Virus (HIV) Env gp120 Complexes Compared to That of Recombinant HIV Type 1 gp120 Envelope Glycoproteins," Journal of Virology, vol. 78, No. 10, pp. 5270-5278 (May 2004).

Litman, G. W., et al., "Evolution of Antigen Binding Receptors," Ann. Rev. Immunol., vol. 17, pp. 109-147 (1999).

Mascola, J. R., et al., "Recommendations for the Design and Use of Standard Virus Panels to Assess Neutralizing Antibody Responses Elicited by Candidate Human Immunodeficiency Virus Type 1 Vaccines," Journal of Virology, vol. 79, No. 16, pp. 10103-10107 (Aug. 2005).

Meffre, E., et al., "Immunoglobulin heavy chain expression shapes the B cell receptor repertoire in human B cell development," J. Clin. Invest., vol. 108, pp. 879-886 (2001).

Moll, S. and Ortel, T. L., "Monitoring Warfarin Therapy in Patients with Lupus Anticoagulants," Annals of Internal Medicine, vol. 127, No. 3, pp. 177-185 (Aug. 1, 1997).

Moore, J. P., et al., "Development of the Anti-gp120 Antibody Response during Seroconversion to Human Immunodeficiency Virus Type 1," Journal of Virology, vol. 68, No. 8, pp. 5142-5155 (Aug. 1994).

Moore, J. P., et al., "Studies with Monoclonal Antibodies to the V3 Region of HIV-1 gp120 Reveal Limitations to the Utility of Solid-Phase Peptide Binding Assays", J. Acquir. Immun. Def. Syn., vol. 7, No. 4, pp. 332-339 (1994).

Nyambi, P. N., et al., "Conserved and Exposed Epitopes on Intact, Native, Primary Human Immunodeiciency Virus Type 1 Virions of Group M," Journal of Virology, vol. 74, No. 15, pp. 7096-7107 (Aug. 2000).

Pancio, H. A., et al., "Interaction of Human Immunodeficiency Virus Type 2 Vpx and Invariant Chain", Journal of Virology, vol. 74, pp. 6168-6172 (Jul. 2000).

Platt, E. J., et al., "Effects of CCR5 and CD4 Cell Surface Concentrations on Infections by Macrophagetropic Isolates of Human Immunodeficiency Virus Type 1," Journal of Virology, vol. 72, No. 4, pp. 2855-2864 (Apr. 1998).

Ramsland, P. A., et al., "Incorporation of Long CDR3s into V Domains: Implications for the Structural Evolution of the Antibody-Combining Site," Exp. Clin. Immunogenet, vol. 18, pp. 176-198 (2001).

Robinson, J. E., et al., "Identification of Conserved and Variant Epitopes of Human Immunodeficiency Virus Type 1 (HIV-1) gp120

(56) References Cited

OTHER PUBLICATIONS by Human Monoclonal Antibodies Produced by EBV-Transformed Cell Lines," AIDS Res. Hum. Retrovirol., vol. 6, p. 567-579 (1990).
Ruprecht, R. M. et al., "Antibody protection: passive immunization of neonates against oral AIDS virus challenge," Vaccine, vol. 21, No. 24, pp. 3370-3373 (Jul. 28, 2003).
Scanlan, C. N., et al., "The Carboydrate Epitope of the Neutralizing Anti-HIV-1 Antibody 2G12," Glycobiology and Medicine,Kluwer Academic/Plenum Publishers, New York, pp. 205-218 (2003).
Stiegler, G., et al., "A Potent Cross-Glade Neutralizing Human Monoclonal Antibody against a Novel Epitope on gp41 of Human Immunodeficiency Virus Type 1,"AIDS Res. Hum. Retroviruses, vol. 17, No. 18, pp. 1757-1765 (2001).
Trkola, A., et al., "Human Monoclonal Antibody 2G12 Defines a Distinctive Neutralization Epitope on the gp120 Glycoprotein of Human Immunodeficiency Virus Type 1," Journal of Virology, vol. 70, No. 2, pp. 1100-1108 (Feb. 1996).
Wei, X., et al., "Emergence of Resistant Human Immunodeficiency Virus Type 1 in Patients Receiving Fusion Inhibitor (T-20) Monotherapy," Antimicrobial Agents and Chemotherapy, vol. 46, No. 6, pp. 1896-1905 (Jun. 2002).
Weiss, L., et al., "Anti-Cardiolipin Antibodies Are Associated with Anti-Endothelial Cell Antibodies but Not with Anti-beta2 Glycoprotein I Antibodies in HIV Infection," Clin. Immunol. Immunopathol., vol. 77, No. 1, pp. 69-74 (1995).
Yuste, E. et al., "Simian Immunodeficiency Virus Engrafted with Human Immunodeficiency Virus Type 1 (HIV-1)-Specific Epitopes: Replication, Neutralization, and Survey of HIV-1-Positive Plasma," Journal of Virology, vol. 80, No. 6, pp. 3030-3041 (Mar. 2006).
Zhang, H., et al., "Induction of Mucosal and Systemic Neutralizing Antibodies against Human Immunodeficiency Virus Type 1 (HIV-1) by Oral Immunization with Bovine Papillomavirus-HIV-1 gp41 Chimeric Virus-Like Particles," Journal of Virology, vol. 78, No. 15, pp. 8342-8348 (Aug. 2004).
Zolla-Pazner, S., et al., "The Cross-Clade Neutralizing Activity of a Human Monoclonal Antibody Is Determined by the GPGR V3 Motif of HIV Type 1," Zolla-Pazner et al., AIDS Res. Hum. Retrovirol., vol. 20, No. 11, pp. 1254-1258 (2004).
Zwick, M. B., et al., "Molecular Features of the Broadly Neutralizing Immunoglobulin G1 b12 Required for Recognition of Human ImmunodeficiencyVirus Type 1 gp120," Journal of Virology, vol. 77, No. 10, pp. 5863-5876 (May 2003).
Albert, J., et al., "Rapid development of isolate-specific neutralizing antibodies after primary HIV-1 infection and consequent emergence of virus variants which resist neutralization by autologous sera," AIDS, vol. 4, No. 2, pp. 107-112, 8 pages in total (Feb. 1990).
Alving, C. R. and Rao, M., "Lipid A and liposomes containing lipid A as antigens and adjuvants," Vaccine, vol. 26, pp. 3036-3045 (2008).
Baba, T. W., et al, "Human neutralizing monoclonal antibodies of the IgG1 subtype protect against mucosal simian-human immunodeficiency virus infection," Nat. Med., vol. 6, No. 2, pp. 200-206 (Feb. 2000).
Beck, Z., et al, "Membrane-specific antibodies induced by liposomes can simultaneously bind to HIV-1 protein, peptide, and membrane lipid epitopes," J. Drug Target, vol. 16, Nos. 7-8, pp. 535-542 (Aug.-Sep. 2008).

Buchacher, A., et al, "Generation of human monoclonal antibodies against HIV-1 proteins; electrofusion and Epstein-Barr virus transformation for peripheral blood lymphocyte immortalization," AIDS Res. Hum. Retroviruses, vol. 10, No. 4, pp. 359-369, 13 pages in total (Apr. 1994).
Decker, J.M., et al, "Failure of the HIV-1 Membrane Proximal External Region (MPER) of HIV-1 gp41 to Elicit 4E10 or 2F5-like Neutralizing Antibodies in Natural Human Infection," presented at the Keystone Symposium on HIV Vaccines, Keystone Resort, Keystone, Colo., 1 page in total (2006).
Douvas, A. and Takehana, Y., "Cross-Reactivity between Autoimmune Anti-U1 snRNP Antibodies and Neutralizing Epitopes of HIV-1 gp120/41", AIDS Research and Human Retroviruses, vol. 10, No. 3, pp. 253-262, 12 pages in total (Mar. 1994).
Douvas, A., et al, "Neutralization of HIV Type 1 Infectivity by Serum Antibodies from a Subset of Autoimmune Patients with Mixed Connective Tissue Disease", AIDS Research and Human Retroviruses, vol. 12, No. 16, pp. 1509-1517, 11 pages in total (Nov. 1, 1996).
Hemmi, H., et al, "Small anti-viral compounds activate immune cells via the TLR7 MyD88 dependent signaling pathway," Nat. Immunol., vol. 3, No. 2, pp. 196-200 (Feb. 2002).
Hemmi, H., et al, "A Toll-like receptor recognizes bacterial DNA", Letters to Nature, vol. 408, pp. 740-745 (Dec. 2000).
Leadbetter, E.A., et al, "Chromatin—IgG complexes activate B cells by dual engagement of IgM and Toll-like receptors," Nature, vol. 416, pp. 603-607 (Apr. 11, 2002).
Matyas, G.R., et al, "Neutralizing antibodies induced liposomal HIV-1 glycoprotein 41 peptide simultaneously bind to both the 2F5 or 4E10 epitope and lipid epitopes," AIDS, vol. 23, No. 16, pp. 2069-2077 (2009).
Ruprecht, R.M., et al, "Antibody protection: passive immunization of neonates against oral AIDS virus challenge," Vaccine, vol. 21, pp. 3370-3373 (2003).
Sanchez-Martinez, S., et al, "Membrane Association and Epitope Recognition by HIV-1 Neutralizing Anti-gp41 2F5 and 4E10 Antibodies," AIDS Res. And Human Retrovir., vol. 22, No. 10, pp. 998-1006 (2006).
Schuster, B.G., et al, "Production of Antibodies against Phosphocholine, Phosphatidylcholine, Sphingomyelin, and Lipid A by Injection of Liposomes Containing Lipid A," J. Immunol., vol. 122, No. 3, pp. 900-905 (Mar. 1979).
Takeda, K., et al, "Toll-like Receptors," Annu. Rev. Immunol., vol. 21, pp. 335-376, 44 pages in total (2003).
Tran, T.T., et al, "Specificity and Immunochemical Properties of anti-DNA Antibodies Induced in Normal Mice by Immunization with Mammalian DNA with a CpG Oligonucleotide as Adjuvant," Clin. Immunol., vol. 109, pp. 278-287 (2003).
Trkola, A., et al, "Delay of HIV-1 rebound after cessation of antiretroviral therapy through passive transfer of human neutralizing antibodies", Nature Medicine, vol. 11, No. 6, pp. 615-622 (Jun. 2005).
Weill, J.-C., et al, "Human Marginal Zone B Cells," Annu. Rev. Immunol., vol. 27, pp. 267-285 (2009).

* cited by examiner

| Target/nature of agent | | TND_669S | TND_669L | |
|---|---|---|---|---|
| MPER | 2F5 | 0.014 | 3.915 | 279x ✓ |
| MPER | 4E10 | 0.031 | 8.054 | 275x ✓ |
| IgG1b12, 2G12, 2F5 | TriMab | 0.030 | 2.866 | 102x |
| CD4 binding site | 1b12 | 0.53 | 2.06 | 3.9x |
| Glycan dependent | 2G12 | 12.5 | 16.68 | 1.3x |
| Fusion Inhibitor | T20 | 0.020 | 0.0545 | 2.8x |
| CD4i | 17b | 9.73 | 19 | 2.0x |
| CD4i, CCR5 binding Site | 1.7B | 27.5 | >50 | >1.8 |
| CD4i | 23E | 24.5 | >50 | >2.0 |
| CD4i, CCR5 binding Site | E51 | 7.6 | >50 | >6.6 |
| V3 loop | 447-52D | 0.31 | >50 | >161 ✓ |

|  | 2F5 IC50 (µg/ml) | |
|---|---|---|
| Peptide Conc. | conensus peptide* | mutant peptide |
| 30 µM | >2.5 | >2.5 |
| 3 µM | >2.5 | 0.951 |
| 0.3 µM | 0.911 | 0.153 |
| 0 µM | 0.054 | 0.056 |

* Previously reported (reference

| | $k_a1$<br>$10^5$ M$^{-1}$ s$^{-1}$ | $k_d1$<br>$10^{-3}$ s$^{-1}$ | $k_a2$<br>$10^{-2}$ s$^{-1}$ | $k_d2$<br>$10^{-4}$ s$^{-1}$ |
|---|---|---|---|---|
| 2F5 peptide liposome | 9.31 | 6.92 | 1.81 | 3.70 |
| L669S 2F5 peptide liposome | 4.98 | 1.19 | 0.54 | 0.20 |

Scheme 1. HIV-1 gp41 MPER peptides that include the epitopes of the two broadly neutralizing antibodies 2F5 and 4E10. Amino acid sequences of the gp41 MPER peptides that can be conjugated to synthetic liposomes are shown.

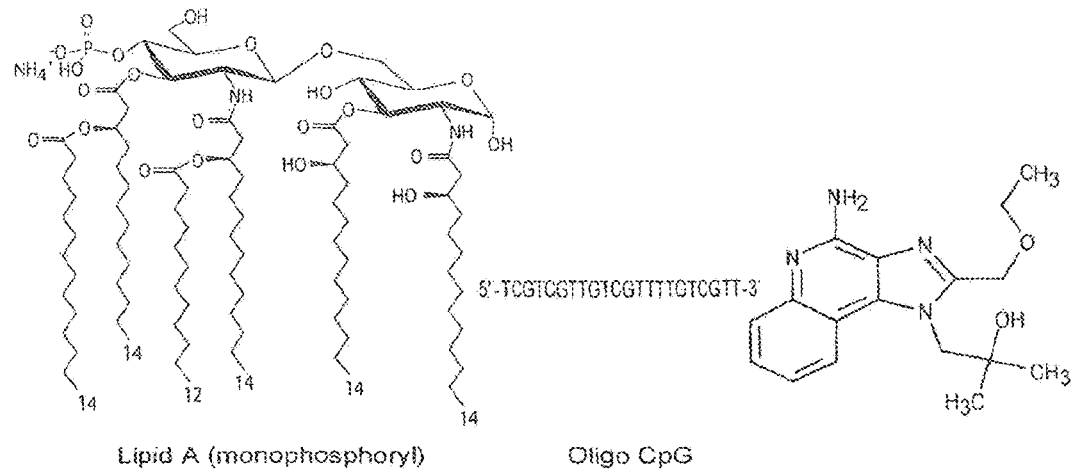
Lipid A (monophosphoryl)    Oligo CpG
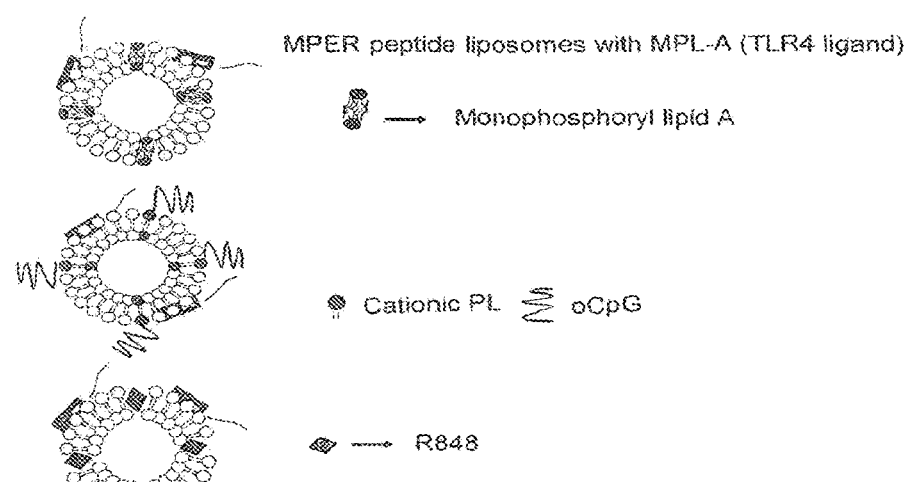
Structures of TLR agonists formulated with liposomes.
Fig. 9

Interaction of 2F5 mAb with MPER peptide-liposomes conjugated to TLR adjuvants.

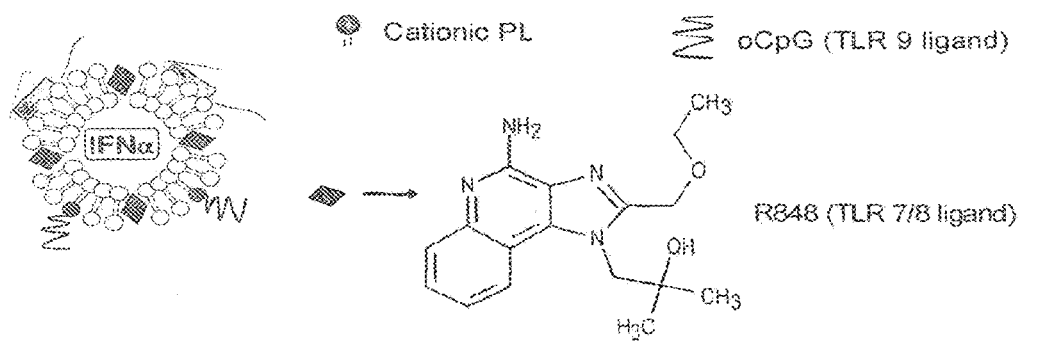
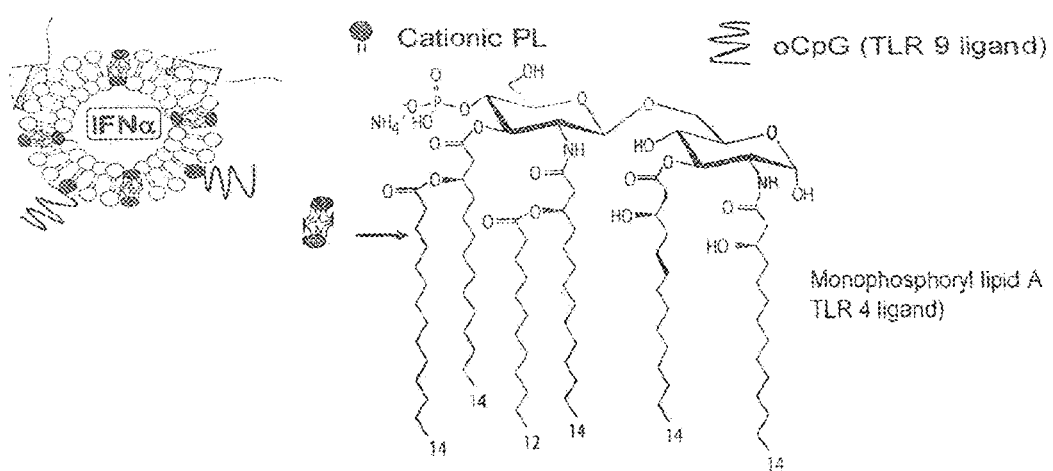
B cell responses via dual TLR triggering.
IFNα encapsulated liposome with multiple TLR ligands. These constructs have the potential to provide synergy in
Fig. 12

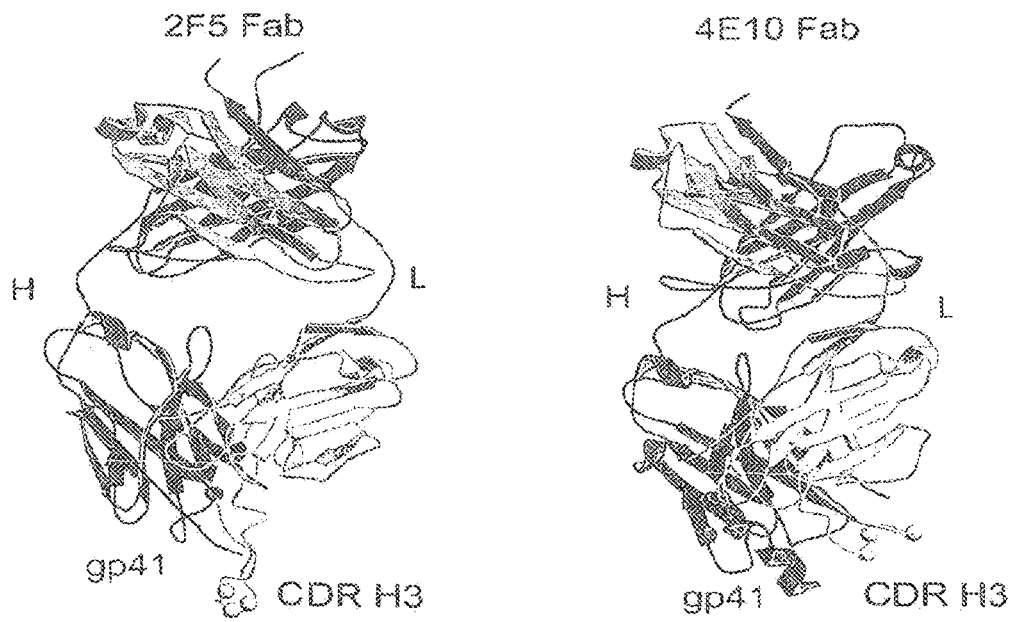
Mutants: 2F5-mut1 rIgG L100aA
2F5-mut2 rIgG F100bA
2F5-mut3 rIgG L100aA/100bB
2F5-mut4 rIgG R95A
Mutants: 4E10-mut1 scFv W100A
4E10-mut2 scFv F100bA
4E10-mut3 scFv W100A/W100bA/L100cA
4E10-mut4 scFv I56A/S94R
Crystal structures of 2F5 (Ofek et al, 2004, , J. Virol., 78:10724) and 4E10 (Cardoso et al., 2005, Immunity, 22:163-173) and design of mutations in the CDR H3 loop to eliminate binding to lipids and HIV-1 viral membrane

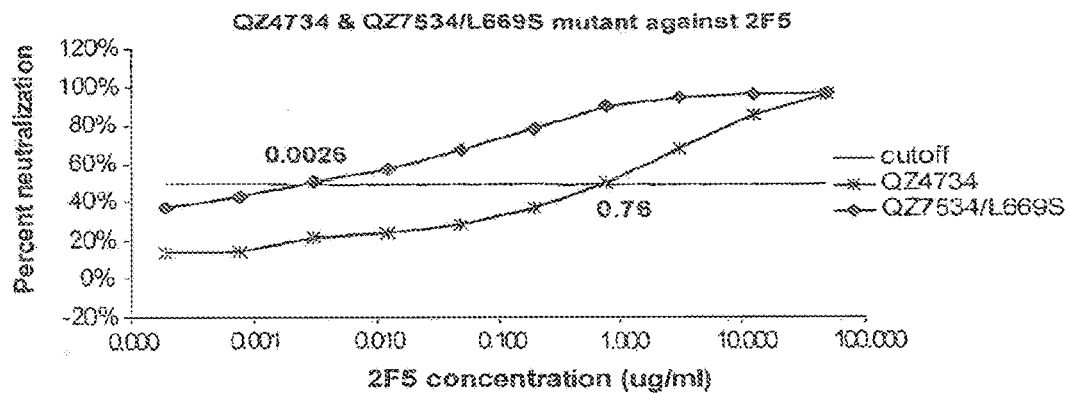

Neutralization of QZ4734 and QZ4734/L669S pseudotyped viruses by 2F5 mAb (tested on TZM-bl cells). QZ4734/L669S was generated by introducing L669S single mutation into the QZ4734 envelope. Numbers by the curves indicate the IC50 values.

Fig. 15

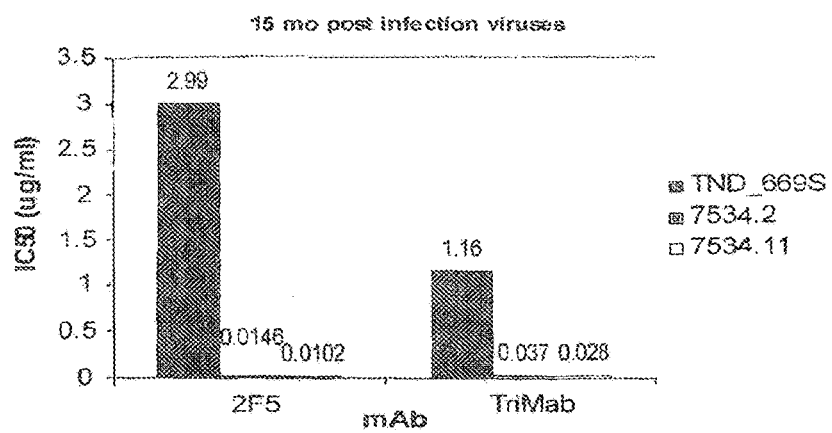

Neutralization of TND_669S and two other stains (7534.2 and 7534.11) isolated from the same plasma sample (15 mo post infection) by 2F5 and TriMab (1:1:1 combination of 2F5, 4E10 and 2G12). Numbers above each bar represents IC50 values. The test was performed on TZM-bl cells.

Fig. 16

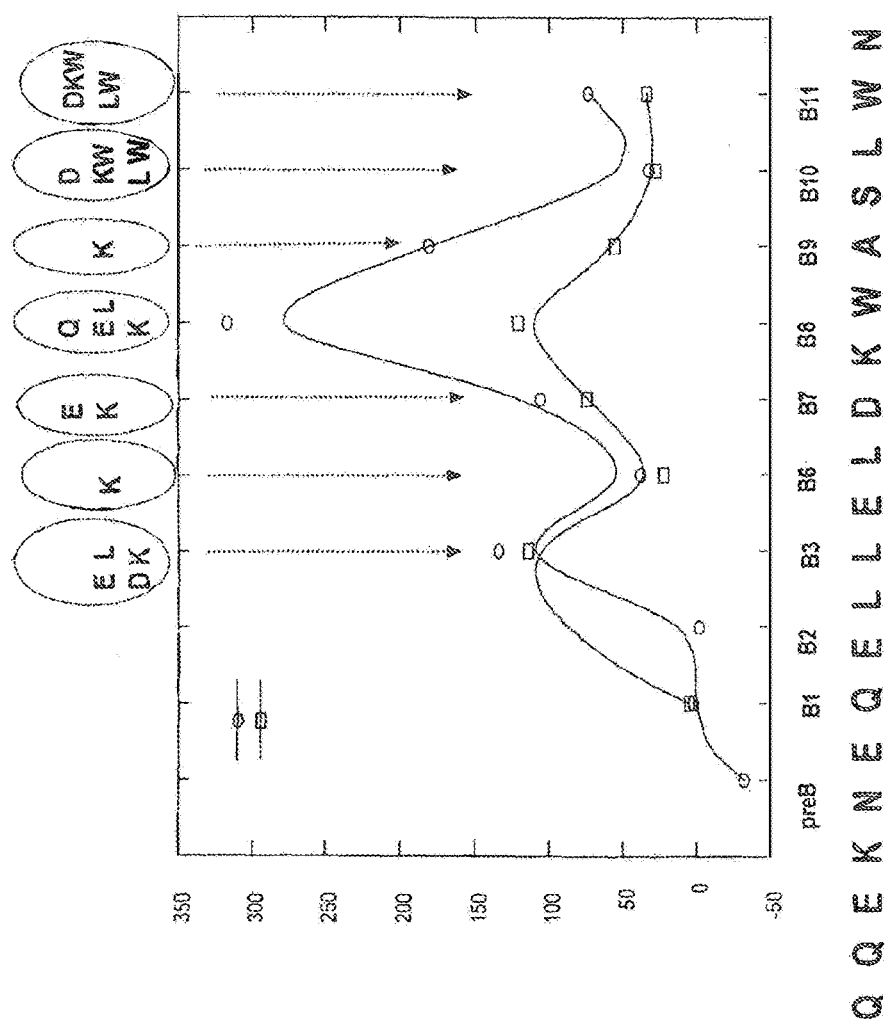
Fig. 17 Induction of gp41 MPER (membrane proximal external region) specific antibody responses in guinea pigs immunized with M Induction of gp41 MPER (membrane proximal external region) specific antibody responses in Non human primates (NHP) immunized with MPER liposomal immunogens.

MPER antibody signatures in the peptide regions – red is associated with resistance, blue is associated with sensitivity, black no impact. The logo is drawn to represent The database 'global' frequency of each amino acid in each position. Resistance can be partial (a shift in the distribution of NAb scores) or complete (detected/undetected neutralization).

```
            2F5                    4E10
                                 10E8
```

The MPER656 peptide matches HXB2; it is very close to subtyp B con, K677Q would make it so. 4E10 tolerates this variation but other antibodies that interact with this epitope might not. I selected common variants that match clade cons, (clades listed on the right), in sites that are likely to matter for the epitope. The blue sites are outside the epitope, and variation may not matter, but I chose them to be clade appropriate just in case.

```
                                              2F5    4E10/10E8
MPER656    NEQELLELDKWASLWNWFNITNWLWYIK       BDE    BE+other
MPER656.1  NEQDLLALDKWASLWNWFDISNWLWYIK       AFG    AFG
MPER656.2  NEKDLLALDSWKNLWNWFSITKWLWYIK       C      CD
MPER656.3  NEQELLALDKWNNLWSWFDITNWLWYIR       other  BE+other
```

Fig. 22A 368 variants of the 2F5 epitope were found in 4036 sequences from different individuals in the database. Below I list the common variants -- the unlisted variants are often only found once or a few times, and often built up from these basic forms. The most common form in each major clade is in red. If a form isn't found at least 1% of the time in a clade it gets a "-". "All" is complete database, all clades and recombinants.

| Pept | Num All | Percent All | Percent by clade | | | | | | |
|---|---|---|---|---|---|---|---|---|---|
| | | | A1 | B | C | D | F | G | E(CRF01) |
| ELDKWAS | | | | | | | | | |
| ------- | 1027 | 25 | 3 | 47 | - | 33 | 9 | - | 67 |
| A------ | 526 | 13 | 39 | 9 | - | 5 | 46 | 57 | 4 |
| A--S-KN | 318 | 8 | - | - | 27 | 1 | - | - | - |
| A----N | 181 | 4 | 28 | 2 | - | 1 | - | - | - |
| A--S-NN | 170 | 4 | - | - | 16 | - | - | - | - |
| -----N | 164 | 4 | 5 | 10 | - | 2 | - | - | 1 |
| A----QN | 112 | 3 | - | - | 10 | 0 | - | - | - |
| other | | 39 | 25 | 30 | 47 | 58 | 45 | 43 | 28 |

Fig. 22B

Numbers corresponding to the yellow boxed regions, the ELDKWA and NWFNIT 6 mers:

ELDKWA in the original vaccine matches ~25% of natural sequence, 55% are ≤1 off, 74% are ≤2 off
The 4 valent matches ~60%, 91% are ≤1 off, 99% are ≤2 off NWFNIT in the original vaccine matches ~5% of of natural sequences, 53% are ≤1 off, 90% are ≤2 off
The 4 valent matches 42%, 96% are ≤1 off, 99.9% are ≤2 off Fig. 24 (continued)

|  | | Earlier lineage members will map like the 2F5 UCA |
|---|---|---|
| 2F5 UCA | E L D K W A S L W N | |
| 2F5 BnAb | E L D K W A S L W N | |
| | | Later lineage members will map more restricted like the 2F5 BnAb |

Fig. 31A

| Epitope map | 2F5 Core (DKW) | Broad 2F5 epitope (ELDKW) | Broad 2F5 epitope with $^{669}$L (ELDKW___L$_{669}$) | Non-2F5 core epitope & low binders |
|---|---|---|---|---|
| # of antibodies | 4 | 11 | 43 | 158 |
| % of Total | 1.9 | 5.1 | 20.0 | 73.0 |

QQEKNEQELLEL$^{664}$DKWAS$^{669}$LWN
— 2F5 BnAb Core
— Broad 2F5 Epitope
— Epitope with $^{669}$L

Fig. 31B

NHP #87

- Group 1- MPER Liposome (656.1) w/ MPLA + R848
- Group 2- MPER Liposome (656.2) w/ MPLA + R848
- Group 3- MPER Liposome (656.3) w/ MPLA + R848
- Group 4- MPER Liposome (656) w/ MPLA + R848
- Group 5- MPER Liposome (Swarm) w/ MPLA + R848

NHP #91

- Group 1- MPER Liposome (656) w/ MPLA (TLR4) Alone
- Group 2- MPER Liposome (656) w/ R848 (TLR7) Alone

Fig. 48

| Plasma Sample | | | | Virus | | | | | | | |
|---|---|---|---|---|---|---|---|---|---|---|---|
| | | | | SVA | | HXB2 | | MN.3 | | W61D.71 | |
| Study | Animal | Group | Week | TZMBL | FCRg | TZMBL | FCRg | TZMBL | FCRg | TZMBL | FCRg |
| 87 | 5710 | 1 | 0 | <20 | <20 | <20 | <20 | <20 | <20 | <20 | <20 |
| 87 | 5710 | 1 | 20 | <20 | <20 | <20 | <20 | <20 | <20 | <20 | <20 |
| 87 | 5712 | 1 | 0 | <20 | <20 | <20 | <20 | <20 | <20 | <20 | <20 |
| 87 | 5712 | 1 | 20 | <20 | <20 | <20 | <20 | <20 | <20 | <20 | <20 |
| 87 | 5716 | 1 | 0 | <20 | <20 | <20 | <20 | <20 | <20 | <20 | <20 |
| 87 | 5716 | 1 | 20 | <20 | <20 | <20 | <20 | <20 | <20 | <20 | <20 |
| 87 | 5717 | 1 | 0 | <20 | <20 | <20 | <20 | <20 | <20 | <20 | <20 |
| 87 | 5717 | 1 | 20 | <20 | <20 | <20 | <20 | <20 | <20 | <20 | <20 |
| 87 | 5718 | 2 | 0 | <20 | <20 | <20 | <20 | <20 | <20 | <20 | <20 |
| 87 | 5718 | 2 | 20 | <20 | <20 | <20 | <20 | <20 | <20 | <20 | <20 |
| 87 | 5724 | 2 | 0 | <20 | <20 | <20 | <20 | <20 | <20 | <20 | <20 |
| 87 | 5724 | 2 | 20 | <20 | <20 | <20 | <20 | <20 | <20 | <20 | <20 |
| 87 | 5725 | 2 | 0 | <20 | <20 | <20 | <20 | <20 | <20 | <20 | <20 |
| 87 | 5725 | 2 | 20 | <20 | <20 | <20 | <20 | <20 | <20 | <20 | <20 |
| 87 | 5733 | 2 | 0 | <20 | <20 | <20 | <20 | <20 | <20 | <20 | <20 |
| 87 | 5733 | 2 | 20 | <20 | <20 | <20 | <20 | <20 | <20 | <20 | <20 |
| 87 | 5593 | 3 | 0 | <20 | <20 | <20 | <20 | <20 | <20 | <20 | <20 |
| 87 | 5593 | 3 | 20 | <20 | <20 | <20 | <20 | <20 | <20 | <20 | <20 |
| 87 | 5594 | 3 | 0 | <20 | <20 | <20 | <20 | <20 | <20 | <20 | <20 |
| 87 | 5594 | 3 | 20 | <20 | <20 | <20 | <20 | <20 | <20 | <20 | <20 |
| 87 | 5595 | 3 | 0 | <20 | <20 | <20 | <20 | <20 | <20 | <20 | <20 |
| 87 | 5595 | 3 | 20 | <20 | <20 | <20 | <20 | <20 | <20 | <20 | <20 |
| 87 | 5713 | 3 | 0 | <20 | <20 | <20 | <20 | <20 | <20 | <20 | <20 |
| 87 | 5713 | 3 | 20 | <20 | <20 | <20 | <20 | <20 | <20 | <20 | <20 |
| 87 | 5602 | 4 | 0 | <20 | <20 | <20 | <20 | <20 | <20 | <20 | <20 |
| 87 | 5602 | 4 | 20 | <20 | <20 | <20 | <20 | <20 | <20 | <20 | <20 |
| 87 | 5606 | 4 | 0 | <20 | <20 | <20 | <20 | <20 | <20 | <20 | <20 |
| 87 | 5606 | 4 | 20 | <20 | <20 | <20 | <20 | <20 | <20 | <20 | <20 |
| 87 | 5608 | 4 | 0 | <20 | <20 | <20 | <20 | <20 | <20 | <20 | <20 |
| 87 | 5608 | 4 | 20 | <20 | <20 | <20 | <20 | <20 | <20 | <20 | <20 |
| 87 | 5609 | 4 | 0 | <20 | <20 | <20 | <20 | <20 | <20 | <20 | <20 |
| 87 | 5609 | 4 | 20 | <20 | <20 | <20 | <20 | <20 | <20 | <20 | <20 |
| 87 | 5610 | 5 | 0 | <20 | <20 | <20 | <20 | <20 | <20 | <20 | <20 |
| 87 | 5610 | 5 | 20 | <20 | <20 | <20 | <20 | <20 | <20 | <20 | <20 |
| 87 | 5615 | 5 | 0 | <20 | <20 | <20 | <20 | <20 | <20 | <20 | <20 |
| 87 | 5615 | 5 | 20 | <20 | <20 | <20 | <20 | <20 | <20 | <20 | <20 |
| 87 | 5619 | 5 | 0 | <20 | <20 | <20 | <20 | <20 | <20 | <20 | <20 |
| 87 | 5619 | 5 | 20 | <20 | <20 | 30 | <20 | <20 | <20 | <20 | <20 |
| 87 | 5621 | 5 | 0 | <20 | <20 | <20 | <20 | <20 | <20 | <20 | <20 |
| 87 | 5621 | 5 | 20 | <20 | <20 | <20 | <20 | <20 | <20 | <20 | <20 |
| 91 | 5350 | 1 | 0 | <20 | <20 | <20 | <20 | <20 | <20 | <20 | <20 |
| 91 | 5350 | 1 | 20 | <20 | <20 | <20 | <20 | <20 | <20 | <20 | <20 |
| 91 | 5565 | 1 | 0 | <20 | <20 | <20 | <20 | <20 | <20 | <20 | <20 |
| 91 | 5565 | 1 | 20 | <20 | <20 | <20 | <20 | <20 | <20 | <20 | <20 |
| 91 | 5566 | 1 | 0 | <20 | <20 | <20 | <20 | <20 | <20 | <20 | <20 |
| 91 | 5566 | 1 | 20 | <20 | <20 | <20 | <20 | <20 | <20 | <20 | <20 |
| 91 | 5547 | 2 | 0 | <20 | <20 | <20 | <20 | <20 | <20 | <20 | <20 |
| 91 | 5547 | 2 | 20 | <20 | <20 | <20 | <20 | <20 | <20 | <20 | <20 |
| 91 | 5548 | 2 | 0 | <20 | <20 | <20 | <20 | <20 | <20 | <20 | <20 |
| 91 | 5548 | 2 | 20 | <20 | <20 | <20 | <20 | <20 | <20 | <20 | <20 |
| 91 | 5562 | 2 | 0 | <20 | <20 | <20 | <20 | <20 | <20 | <20 | <20 |
| 91 | 5562 | 2 | 20 | <20 | <20 | <20 | <20 | <20 | <20 | <20 | <20 |

SEQUENCE LISTING

```
<160> NUMBER OF SEQ ID NOS: 85

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Leu Asp Lys Trp Ala Ser
1               5

<210> SEQ ID NO 2
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 2

Asn Trp Phe Asn Ile Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Asp Lys Trp Ala Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Trp Phe Asn Ile Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Leu Asp Ser Trp Lys Asn
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Trp Phe Ser Ile Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Leu Asp Lys Trp Asn Asn
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Trp Phe Asp Ile Thr
1               5

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Glu Gln Glu Leu Leu Glu Leu Asp Lys Trp Ala Ser Leu Trp Asn
1               5                   10                  15

Trp Phe Asn Ile Thr Asn Trp Leu Trp Tyr Ile Lys
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Glu Gln Asp Leu Leu Ala Leu Asp Lys Trp Ala Ser Leu Trp Asn
1               5                   10                  15

Trp Phe Asp Ile Ser Asn Trp Leu Trp Tyr Ile Lys
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Glu Lys Asp Leu Leu Ala Leu Asp Ser Trp Lys Asn Leu Trp Asn
1               5                   10                  15

Trp Phe Ser Ile Thr Lys Trp Leu Trp Tyr Ile Lys
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Glu Gln Glu Leu Leu Ala Leu Asp Lys Trp Asn Asn Leu Trp Ser
1               5                   10                  15
```

Trp Phe Asp Ile Thr Asn Trp Leu Trp Tyr Ile Arg
            20                  25

<210> SEQ ID NO 13
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asn Glu Gln Glu Leu Leu Glu Leu Asp Lys Trp Ala Ser Leu Trp Asn
1               5                   10                  15

Trp Phe Asn Ile Thr Asn Trp Leu Trp Tyr Ile Lys Tyr Lys Arg Trp
            20                  25                  30

Ile Ile Leu Gly Leu Asn Lys Ile Val Arg Met Tyr Ser
        35                  40                  45

<210> SEQ ID NO 14
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asn Glu Gln Asp Leu Leu Ala Leu Asp Lys Trp Ala Ser Leu Trp Asn
1               5                   10                  15

Trp Phe Asp Ile Ser Asn Trp Leu Trp Tyr Ile Lys Tyr Lys Arg Trp
            20                  25                  30

Ile Ile Leu Gly Leu Asn Lys Ile Val Arg Met Tyr Ser
        35                  40                  45

<210> SEQ ID NO 15
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asn Glu Lys Asp Leu Leu Ala Leu Asp Ser Trp Lys Asn Leu Trp Asn
1               5                   10                  15

Trp Phe Ser Ile Thr Lys Trp Leu Trp Tyr Ile Lys Tyr Lys Arg Trp
            20                  25                  30

Ile Ile Leu Gly Leu Asn Lys Ile Val Arg Met Tyr Ser
        35                  40                  45

<210> SEQ ID NO 16
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asn Glu Gln Glu Leu Leu Ala Leu Asp Lys Trp Asn Asn Leu Trp Ser
1               5                   10                  15

Trp Phe Asp Ile Thr Asn Trp Leu Trp Tyr Ile Arg Tyr Lys Arg Trp
            20                  25                  30

```
Ile Ile Leu Gly Leu Asn Lys Ile Val Arg Met Tyr Ser
        35                  40                  45

<210> SEQ ID NO 17
<211> LENGTH: 17
<212> TYPE: PRT
<213> ORGANISM: Human immunodeficiency virus 1

<400> SEQUENCE: 17

Tyr Lys Arg Trp Ile Ile Leu Gly Leu Asn Lys Ile Val Arg Met Tyr
1               5                   10                  15

Ser

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Glu Gln Glu Leu Leu Glu Leu Asp Lys Trp Ala Ser
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Glu Gln Asp Leu Leu Ala Leu Asp Lys Trp Ala Ser
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Glu Lys Asp Leu Leu Ala Leu Asp Ser Trp Lys Asn
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Glu Gln Glu Leu Leu Ala Leu Asp Lys Trp Asn Asn
1               5                   10

<210> SEQ ID NO 22
<211> LENGTH: 13
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 22

Asn Trp Phe Asn Ile Thr Asn Trp Leu Trp Tyr Ile Lys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Trp Phe Asp Ile Ser Asn Trp Leu Trp Tyr Ile Lys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Trp Phe Ser Ile Thr Lys Trp Leu Trp Tyr Ile Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Trp Phe Asp Ile Thr Asn Trp Leu Trp Tyr Ile Arg
1               5                   10

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Glu Lys Asp Leu Leu Ala Leu Asp Ser Trp Lys Asn Leu Trp Asn
1               5                   10                  15

Trp Phe Asp Ile Thr Lys Trp Leu Trp Tyr Ile Lys
            20                  25

<210> SEQ ID NO 27
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asn Glu Lys Asp Leu Leu Ala Leu Asp Ser Trp Lys Asn Leu Trp Asn

```
1               5                   10                  15
Trp Phe Asp Ile Thr Lys Trp Leu Trp Tyr Ile Lys Tyr Lys Arg Trp
                20                  25                  30

Ile Ile Leu Gly Leu Asn Lys Ile Val Arg Met Tyr Ser
                35                  40                  45

<210> SEQ ID NO 28
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term biotin

<400> SEQUENCE: 28

Lys Lys Lys Asn Glu Gln Glu Leu Leu Glu Leu Asp Lys Trp Ala Ser
1               5                   10                  15

Leu Trp Asn Trp Phe Asn Ile Thr Asn Trp Leu Trp Tyr Ile Lys Lys
                20                  25                  30

Lys Lys

<210> SEQ ID NO 29
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term biotin

<400> SEQUENCE: 29

Lys Lys Lys Asn Glu Gln Asp Leu Leu Ala Leu Asp Lys Trp Ala Ser
1               5                   10                  15

Leu Trp Asn Trp Phe Asp Ile Ser Asn Trp Leu Trp Tyr Ile Lys Lys
                20                  25                  30

Lys Lys

<210> SEQ ID NO 30
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term biotin

<400> SEQUENCE: 30

Lys Lys Lys Asn Glu Lys Asp Leu Leu Ala Leu Asp Ser Trp Lys Asn
1               5                   10                  15

Leu Trp Asn Trp Phe Ser Ile Thr Lys Trp Leu Trp Tyr Ile Lys Lys
                20                  25                  30

Lys Lys

<210> SEQ ID NO 31
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: C-term biotin

<400> SEQUENCE: 31

Lys Lys Lys Asn Glu Gln Glu Leu Leu Ala Leu Asp Lys Trp Asn Asn
1               5                   10                  15

Leu Trp Ser Trp Phe Asp Ile Thr Asn Trp Leu Trp Tyr Ile Arg Lys
            20                  25                  30

Lys Lys

<210> SEQ ID NO 32
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term biotin

<400> SEQUENCE: 32

Lys Lys Lys Asn Glu Lys Asp Leu Leu Ala Leu Asp Ser Trp Lys Asn
1               5                   10                  15

Leu Trp Asn Trp Phe Asp Ile Thr Lys Trp Leu Trp Tyr Ile Lys Lys
            20                  25                  30

Lys Lys

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tagagccctg aagcatcca ggaag                                          25

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttgctacttg tgattgctcc atgt                                          24

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cacctaggca tctcctatgg caggaagaag                                    30

<210> SEQ ID NO 36
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 36
gtctcgagat actgctccca ccc                                              23

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggataagtgg gcaagtttgt ggaattggtt tgac                                  34

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtcaaaccaa ttccacaaac ttgcccactt atcc                                  34

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaattattag aattggataa ctgggcaagt tcgtgg                                36

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccacgaactt gcccagttat ccaattctaa taattc                                36

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Gln Glu Lys Asn Glu Gln Glu Leu Leu Glu Leu Asp Lys Trp Ala
1               5                   10                  15

Ser Leu Trp Asn
            20

<210> SEQ ID NO 42
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term biotin

<400> SEQUENCE: 42

Gln Gln Glu Lys Asn Glu Gln Glu Leu Leu Glu Leu Asp Lys Trp Ala
1               5                   10                  15

Ser Leu Trp Asn Tyr Lys Arg Trp Ile Ile Leu Gly Leu Asn Lys Ile
            20                  25                  30

Val Arg Met Tyr Ser
        35

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term biotin

<400> SEQUENCE: 43

Gln Gln Glu Lys Asn Glu Gln Glu Leu Leu Glu Leu Asp Lys Trp Ala
1               5                   10                  15

Ser Ser Trp Asn Tyr Lys Arg Trp Ile Ile Leu Gly Leu Asn Lys Ile
            20                  25                  30

Val Arg Met Tyr Ser
        35

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Gln Glu Leu Leu Glu Leu Asp Lys Trp Ala Ser Leu Trp Asn
1               5                   10                  15

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Leu Asp Lys Trp Ala
1               5

<210> SEQ ID NO 46
<211> LENGTH: 52
<212> TYPE: PRT
<213> ORGANISM: Human immunodeficiency virus 1

<400> SEQUENCE: 46

Asp Tyr Ile Tyr Ser Leu Leu Glu Asn Ala Gln Asn Gln Gln Glu Arg
1               5                   10                  15
```

Asn Glu Gln Glu Leu Leu Glu Leu Asp Lys Trp Ala Ser Leu Trp Asn
            20                  25                  30

Trp Phe Asp Ile Thr Lys Trp Leu Trp Tyr Ile Lys Ile Phe Ile Met
        35                  40                  45

Ile Val Gly Gly
    50

<210> SEQ ID NO 47
<211> LENGTH: 52
<212> TYPE: PRT
<213> ORGANISM: Human immunodeficiency virus 1

<400> SEQUENCE: 47

Asp Tyr Ile Tyr Ser Leu Leu Glu Asn Ala Gln Asn Gln Gln Glu Lys
1               5                   10                  15

Asn Glu Gln Glu Leu Leu Glu Leu Asp Lys Trp Ala Ser Leu Trp Asn
            20                  25                  30

Trp Phe Asp Ile Ser Lys Trp Leu Trp Tyr Ile Lys Ile Phe Ile Met
        35                  40                  45

Ile Val Gly Gly
    50

<210> SEQ ID NO 48
<211> LENGTH: 52
<212> TYPE: PRT
<213> ORGANISM: Human immunodeficiency virus 1

<400> SEQUENCE: 48

Gly Phe Ile Tyr Ser Leu Leu Glu Asn Ala Gln Asn Gln Gln Glu Lys
1               5                   10                  15

Asn Glu Gln Glu Leu Leu Glu Leu Asp Lys Trp Ala Ser Leu Trp Asn
            20                  25                  30

Trp Phe Asp Ile Ser Lys Trp Leu Trp Tyr Ile Lys Ile Phe Ile Met
        35                  40                  45

Ile Val Gly Gly
    50

<210> SEQ ID NO 49
<211> LENGTH: 52
<212> TYPE: PRT
<213> ORGANISM: Human immunodeficiency virus 1

<400> SEQUENCE: 49

Asp Phe Ile Tyr Ser Leu Leu Glu Asn Ala Gln Asn Gln Gln Glu Lys
1               5                   10                  15

Asn Glu Gln Glu Leu Leu Glu Leu Asp Lys Trp Ala Ser Leu Trp Asn
            20                  25                  30

Trp Phe Asp Ile Asn Lys Trp Leu Trp Tyr Ile Lys Ile Phe Ile Met
        35                  40                  45

Ile Val Gly Gly
    50

<210> SEQ ID NO 50
<211> LENGTH: 52
<212> TYPE: PRT
<213> ORGANISM: Human immunodeficiency virus 1

<400> SEQUENCE: 50

Asp Phe Ile Tyr Ser Leu Leu Glu Asn Ala Gln Asn Gln Gln Glu Lys

```
                    1               5                   10                  15
                Asn Glu Gln Glu Leu Leu Glu Leu Asp Lys Trp Ala Ser Ser Trp Asn
                                20                  25                  30

Trp Phe Asp Ile Asn Lys Trp Leu Trp Tyr Ile Lys Ile Phe Ile Met
                            35                  40                  45

Ile Val Gly Gly
                    50

<210> SEQ ID NO 51
<211> LENGTH: 52
<212> TYPE: PRT
<213> ORGANISM: Human immunodeficiency virus 1

<400> SEQUENCE: 51

Asp Phe Ile Tyr Ser Leu Leu Glu Asn Ala Gln Asn Gln Gln Glu Lys
1               5                   10                  15

Asn Glu Gln Glu Leu Leu Glu Leu Asp Lys Arg Ala Ser Leu Trp Asn
                20                  25                  30

Trp Phe Asp Ile Asn Lys Trp Leu Trp Tyr Ile Lys Ile Phe Ile Met
            35                  40                  45

Ile Val Gly Gly
    50

<210> SEQ ID NO 52
<211> LENGTH: 52
<212> TYPE: PRT
<213> ORGANISM: Human immunodeficiency virus 1

<400> SEQUENCE: 52

Asp Tyr Ile Tyr Ser Leu Leu Glu Asn Ala Gln Asn Gln Gln Glu Lys
1               5                   10                  15

Asn Glu Gln Glu Leu Leu Glu Leu Asp Lys Trp Ala Ser Leu Trp Asn
                20                  25                  30

Trp Phe Asp Ile Asn Lys Trp Leu Trp Tyr Ile Lys Ile Phe Ile Met
            35                  40                  45

Ile Val Gly Gly
    50

<210> SEQ ID NO 53
<211> LENGTH: 52
<212> TYPE: PRT
<213> ORGANISM: Human immunodeficiency virus 1

<400> SEQUENCE: 53

Asp Tyr Ile Tyr Ser Leu Leu Glu Asn Ala Gln Asn Gln Gln Glu Lys
1               5                   10                  15

Asn Glu Gln Glu Leu Leu Gly Leu Asp Lys Trp Ala Ser Leu Trp Asn
                20                  25                  30

Trp Ser Asp Ile Asn Lys Trp Leu Trp Tyr Arg Lys Ile Phe Ile Met
            35                  40                  45

Ile Val Gly Gly
    50

<210> SEQ ID NO 54
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 54

Gln Gln Glu Lys Asn Glu Gln Glu Leu Leu Glu Leu Asp Lys Trp Ala
1               5                   10                  15

Ser Leu Trp Asn Trp Phe Asn Ile Thr Asn Trp Leu Tyr Ile Lys
            20                  25                  30

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Gln Glu Lys Asn Glu Gln Glu Leu Leu Glu Leu Asp Lys Trp Ala
1               5                   10                  15

Ser Ser Trp Asn
            20

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Glu Gln Glu Leu Leu Glu Leu Asp Lys Trp Ala Ser Ser Trp Asn
1               5                   10                  15

Trp Phe Asn Ile Thr Asn Trp Leu Trp Tyr Ile Lys
            20                  25

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tcgtcgttgt cgttttgtcg tt                                            22

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Leu Asp Lys Trp Ala Asn
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 59

Ala Leu Asp Ser Trp Asn Asn
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Leu Asp Lys Trp Ala Asn
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Leu Asp Lys Trp Gln Asn
1               5

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Trp Phe Asp Ile Thr Asn Trp Leu Trp Tyr Ile Lys
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Trp Phe Asp Ile Thr Lys Trp Leu Trp Tyr Ile Lys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Trp Phe Ser Ile Thr Asn Trp Leu Trp Tyr Ile Lys
1               5                   10

<210> SEQ ID NO 65
<211> LENGTH: 13
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 65

Asn Trp Phe Asp Ile Thr Asn Trp Leu Trp Tyr Ile Arg
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Leu Asp Lys Trp Ala Ser Leu Trp Asn
1               5                   10

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Leu Asp Lys Trp
1               5

<210> SEQ ID NO 68
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
caggtgacct tgaaggagtc tggtcctgcg ctggtgaaac ccacacagac cctcacgctg      60
acctgcacct ctctctgggtt ctcactcaac actagtggta tgggtgtggg ctggatccgt    120
cagcccccag ggaaggccct ggaatggctt gcaagcattt attgggatga tgataaatac    180
tacagcacat cgctgaagag caggctcacc atctccaagg acacctccaa aaaccaggtg    240
gttctaacaa tgaccaacat ggaccctgtg gacacagcca catattactg tgcacggaga    300
catatcacgc agtgggtact atttgcccgg ggtagagact acggtttgga ttcctggggc    360 caagggtcg tcgtcaccgt ctcctca                                          387

<210> SEQ ID NO 69
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
caggtgacct tgaaggagtc tggtcctacg ttggtgaaac ccacacagac cctcacgctg      60
acctgcatct ctctggcttt tcactcaac actgttggat tgggtgtggg ctggatccgt     120
cagtccccag ggaagggcct ggaatggctt gcaaccatct attgggatga agataaatac    180

```
tatagcacat ctctgaagag caggctcacc atctccaagg acacctccga aaaccaggtc    240
gttctaacaa tgaccagcat ggaccctgtg dacacagcca catactactg tgcacggaga    300
caaatcacgc agtgggggct atttgcccgg gggagagact acggtttgga tgcctggggc    360 caggggggtct tcgtcaccgt ctcctca                                       387
```

```
<210> SEQ ID NO 70
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
caggtgacct tgaaggagtc tggtcctgcg ctggtgaaac ccacacagac cctcacgctg    60
acctgcatct tctctggctt ttcactcaat agtgttggta tgggtgtggg ctggatccgt    120
cagcccccag ggaaggccct ggaatggctt gcaaccattt attgggatga tgataaatac    180
tacagcacat ctctgaagag caggctcacc atctccaagg acacctccaa aaaccaggtg    240
cttctgacag tgaccaacat ggaccctgtg dacacaggca catattactg tgcacggaga    300
catatcacgc agtggacact atttgcccgg ggtagagact acggtttgga ttcctggggc    360 caggggggccc tcgtcaccgt ctcctca                                       387
```

```
<210> SEQ ID NO 71
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
caggtgacct tgaaggaggc tggtcctgcg ctggtgaaac ccacacagac cctcacgctg    60
acctgcatgt tctctggctt ttcactcaac actgttggtc tgggtgtggg ctgggtccgt    120
cagcccccag ggatggccct ggaatggctt gcgaccattt attgggatga tgataagaat    180
tacagtccat ctctgaagaa caggctcacc atctccaagg acacctccaa aaaccaggtg    240
attctgacaa tgaccaatat ggaccctatg gagacaggca catattactg tgcacggaga    300
cacatcaccc agtggctcct atttgcccgg ggtagagact cggtttgga tgcctggggc    360 caggggggtcc tcgtcaacgt ctcctca                                       387
```

```
<210> SEQ ID NO 72
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Asn Thr Ser
                20                  25                  30

Gly Met Gly Val Gly Trp Ile Arg Gln Pro Pro Gly Lys Ala Leu Glu
            35                  40                  45
```

Trp Leu Ala Ser Ile Tyr Trp Asp Asp Asp Lys Tyr Tyr Ser Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg His Ile Thr Gln Trp Val Leu Phe Ala Arg Gly Arg
            100                 105                 110

Asp Tyr Gly Leu Asp Ser Trp Gly Gln Gly Val Val Thr Val Ser
            115                 120                 125

Ser

<210> SEQ ID NO 73
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Thr Leu Lys Glu Ser Gly Pro Thr Leu Val Lys Pro Thr Gln
1               5                   10                  15

Thr Leu Thr Leu Thr Cys Ile Phe Ser Gly Phe Ser Leu Asn Thr Val
                20                  25                  30

Gly Leu Gly Val Gly Trp Ile Arg Gln Ser Pro Gly Lys Gly Leu Glu
            35                  40                  45

Trp Leu Ala Thr Ile Tyr Trp Asp Glu Asp Lys Tyr Tyr Ser Thr Ser
    50                  55                  60

Leu Lys Ser Arg Leu Thr Ile Ser Lys Asp Thr Ser Glu Asn Gln Val
65                  70                  75                  80

Val Leu Thr Met Thr Ser Met Asp Pro Val Asp Thr Ala Thr Tyr Tyr
                85                  90                  95

Cys Ala Arg Arg Gln Ile Thr Gln Trp Gly Leu Phe Ala Arg Gly Arg
            100                 105                 110

Asp Tyr Gly Leu Asp Ala Trp Gly Gln Gly Val Phe Val Thr Val Ser
            115                 120                 125

Ser

<210> SEQ ID NO 74
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Thr Leu Lys Glu Ser Gly Pro Ala Leu Val Lys Pro Thr Gln
1               5                   10                  15

Thr Leu Thr Leu Thr Cys Ile Phe Ser Gly Phe Ser Leu Asn Ser Val
                20                  25                  30

Gly Met Gly Val Gly Trp Ile Arg Gln Pro Pro Gly Lys Ala Leu Glu
            35                  40                  45

Trp Leu Ala Thr Ile Tyr Trp Asp Asp Asp Lys Tyr Tyr Ser Thr Ser
    50                  55                  60

Leu Lys Ser Arg Leu Thr Ile Ser Lys Asp Thr Ser Lys Asn Gln Val
65                  70                  75                  80

Leu Leu Thr Val Thr Asn Met Asp Pro Val Asp Thr Gly Thr Tyr Tyr
            85                  90                  95

Cys Ala Arg Arg His Ile Thr Gln Trp Thr Leu Phe Ala Arg Gly Arg
            100                 105                 110

Asp Tyr Gly Leu Asp Ser Trp Gly Gln Gly Ala Leu Val Thr Val Ser
        115                 120                 125

Ser

<210> SEQ ID NO 75
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Thr Leu Lys Glu Ala Gly Pro Ala Leu Val Lys Pro Thr Gln
1               5                   10                  15

Thr Leu Thr Leu Thr Cys Met Phe Ser Gly Phe Ser Leu Asn Thr Val
            20                  25                  30

Gly Leu Gly Val Gly Trp Val Arg Gln Pro Pro Gly Met Ala Leu Glu
        35                  40                  45

Trp Leu Ala Thr Ile Tyr Trp Asp Asp Asp Lys Asn Tyr Ser Pro Ser
    50                  55                  60

Leu Lys Asn Arg Leu Thr Ile Ser Lys Asp Thr Ser Lys Asn Gln Val
65                  70                  75                  80

Ile Leu Thr Met Thr Asn Met Asp Pro Met Glu Thr Gly Thr Tyr Tyr
            85                  90                  95

Cys Ala Arg Arg His Ile Thr Gln Trp Leu Leu Phe Ala Arg Gly Arg
            100                 105                 110

Asp Phe Gly Leu Asp Ala Trp Gly Gln Gly Val Leu Val Asn Val Ser
        115                 120                 125

Ser

<210> SEQ ID NO 76
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
cagatcacct tgaaggagtc tggtcctacg ctggtgaaac ccacacagac cctcacgctg    60
acctgcacct tctctgggtt ctcactctcc actagtggag tgggtgtggg ctggatccgt    120
cagcccccag gaaaggccct ggagtggctt gcactcattt attgggatga tgataagcgc    180
tacggcccat ctctgaagag caggctcacc atcaccaagg acacctccaa aaaccaggtg    240
gtccttacaa tgaccaacat ggaccctgtg acacagcca catattactg tgcacacaga    300
cgggggccaa ccacactttt tggagtggtt attgcccggg accagtgaa cggaatggac    360 gtctggggc aagggaccac ggtcaccgtc tcctca    396

<210> SEQ ID NO 77
<211> LENGTH: 132
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 77

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Gly Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Arg Gly Pro Thr Thr Leu Phe Gly Val Ile Ala
            100                 105                 110

Arg Gly Phe Val Asn Gly Met Asp Val Trp Gly Gln Gly Thr Thr Val
            115                 120                 125

Thr Val Ser Ser
    130

<210> SEQ ID NO 78
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attgggatga tgataagcgc     180
tacagcccat ctctgaagag caggctcacc atcaccaagg acacctccaa aaaccaggtg     240
gtccttacaa tgaccaacat ggaccctgtg gacacagcca catattactg tgcacgg       297

<210> SEQ ID NO 79
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
caggtgacct tgaaggagtc tggtcctgcg ctggtgaaac ccacacagac cctcacgctg      60
acctgcacct tctctgggtt ctcactcaac actagtggta tgggtgtggg ctggatccgt     120
cagcccccag ggaaggccct ggaatggctt gcaagcattt attgggatga tgataaatac     180
tacagcacat cgctgaagag caggctcacc atctccaagg acacctccaa aaaccaggtg     240
gttctaacaa tgaccaacat ggaccctgtg gacacagcca catattactg tgcacgggta    300

<210> SEQ ID NO 80
<211> LENGTH: 33
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 80

Cys Ala His Arg Arg Gly Pro Thr Thr Leu Phe Gly Val Val Ile Ala
1               5                   10                  15

Arg Gly Pro Val Asn Gly Met Asp Val Trp Ile Tyr Trp Asp Asp Asp
            20                  25                  30

Lys

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Cys Ala Arg Arg His Ile Thr Gln Trp Val Leu Phe Ala Arg Gly Arg
1               5                   10                  15

Asp Tyr Gly Leu Asp Ser Trp Ile Tyr Trp Asp Asp Asp Lys
            20                  25                  30

<210> SEQ ID NO 82
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Cys Ala His Arg Arg Gly Pro Thr Thr Leu Phe Gly Val Pro Ile Ala
1               5                   10                  15

Arg Gly Pro Val Asn Ala Met Asp Val Trp Ile Tyr Ser Asp Asp Asp
            20                  25                  30

Lys

<210> SEQ ID NO 83
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Cys Ala Arg Arg His Ile Thr Gln Trp Thr Leu Phe Ala Arg Gly Arg
1               5                   10                  15

Asp Tyr Gly Leu Asp Ser Trp Ile Tyr Trp Asp Asp Asp Lys
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

-continued

```
Cys Ala Arg Arg Gln Ile Thr Gln Trp Gly Leu Phe Ala Arg Gly Arg
1               5                   10                  15

Asp Tyr Gly Leu Asp Ala Trp Ile Tyr Trp Asp Glu Asp Lys
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Cys Ala Arg Arg His Ile Thr Gln Trp Leu Leu Phe Ala Arg Gly Arg
1               5                   10                  15

Asp Phe Gly Leu Asp Ala Trp Ile Tyr Trp Asp Asp Asp Lys
            20                  25                  30
```

MPER-LIPOSOME CONJUGATES AND USES THEREOF

This application is the National Stage of International Application No. PCT/US2014/058032, filed Sep. 29, 2014, which claims the benefit of and priority to U.S. Provisional Patent Application No. 61/883,306 filed Sep. 27, 2013, the entire contents of which application is herein incorporated by reference.

This invention was made with government support under Grant No. AI 067854 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 1, 2016, is named 1234300_00156US2_SL.txt and is 36,232 bytes in size.

TECHNICAL FIELD

The present invention relates in general, to a formulation suitable for use in inducing anti-HIV-1 antibodies, and, in particular, to a formulation comprising Toll Like Receptor (TLR) agonists with HIV-1 gp41 membrane proximal external region (MPER) peptide-liposome conjugates for induction of broadly reactive anti-HIV-1 antibodies. The invention also relates to methods of inducing neutralizing anti-HIV-1 antibodies using such formulations.

BACKGROUND

One of the major challenges to HIV-1 vaccine development has been the inability of immunogens to induce broadly neutralizing antibodies (nAb). nAbs are generated during HIV-1 infection. However, most of the nAbs generated neutralize only the autologous viruses or closely related strains (Moog et al, J. Virol. 71:3734-3741 (1997), Gray et al, J. Virol. 81:6187-6196 (2007)). HIV envelope (Env) constantly mutates to escape from existing nAb response (Albert et al, Aids 4:107-112 (1990), Wei et al, Nature 422:307-312) (2003)). nAb responses do evolve over the course of the HIV infection. However, with the mutation capacity of HIV-1 viruses, neutralizing antibody responses always seem to "lag behind" virus evolution (Wei et al, Nature 422:307-312 (2003)), Richman et al, Proc. Natl. Acad. Sci. USA 100:4144-4149 (2003), Geffin et al, Virology 310:207-215 (2003)).

After extensive research, a handful of broadly neutralizing monoclonal antibodies (mAbs) against HIV-1 have been identified (Buchacher et al, AIDS Res. Hum. Retroviruses 10:359-369 (1994), Zwick et al, J. Virol. 75:10892-10895 (2001), Burton et al, Proc. Natl. Acad. Sci. USA 888:10134-10137 (1991)). Two such antibodies, 2F5 and 4E10, target the conserved membrane-proximal external region (MPER) of HIV-1, have a broad spectrum of neutralization (Binley et al, J. Virol. 78:13232-13252 (2004)), and have been shown to neutralize 80% and 100% of newly transmitted viruses (Mehandru et al, J. Virol. 78:14039-14042 (2004)), respectively. When passively administered in combination with several other broadly neutralizing monoclonal antibodies, a cocktail of mAbs composed of 2G12, 2F5 and 4E10 successfully protected the host from virus infection in animal models (Baba et al, Nat. Med. 6:200-206 (2000), Ferrantelli et al, J. Infect. Dis. 189:2167-2173 (2004), Mascola et al, Nat. Med. 6:207-210 (2000), Ruprecht et al, Vaccine 21:3370-3373 (2003)), or delayed virus rebound after cessation of antiretroviral therapy (Trkola et al, Nat. Med. 11:615-622 (2005)).

The potential of using 2F5 and 4E10 to prevent HIV infection is greatly compromised by the fact that HIV infected patients rarely develop these antibodies spontaneously (Dhillon et al, J. Virol. 81:6548-6562 (2007)), and there has been no success in inducing 2F5- and 4E10-like antibodies by vaccination (Kim et al, Vaccine 25:5102-5114 (2006), Coeffier et al, Vaccine 19:684-693 (2000), Joyce et al, J. Biol. Chem. 277:45811-45820 (2002), Ho et al, Vaccine 23:1559-1573 (2005), Zhang et al, Immunobiology 210:639-645 (2005)). Identification of subjects that develop 2F5- or 4E10-like antibodies during natural HIV-1 infection, and developing an understanding of the mechanism of, or hindrance to, these broadly neutralizing antibodies is important for AIDS vaccine design.

The present invention results, at least in part, from the identification and characterization of a rare Env mutation in the HIV-1 MPER region which is associated with an increase in neutralization sensitivity to 2F5 and 4E10 mAbs. The invention also results from the development of constructs that can modulate B cell tolerance and enhance antibody responses against poorly immunogenic HIV-1gp41MPER epitopes.

SUMMARY OF THE INVENTION

In general, the present invention relates to a formulation suitable for use in inducing anti-HIV-1 antibodies. More specifically, the invention relates to a formulation comprising TLR agonists with HIV-1 gp41MPER peptide-liposome conjugates, and to methods of inducing broadly reactive neutralizing anti-HIV-1 antibodies using same.

In certain aspects the invention provides MPER peptides, including but not limited to MPER peptides with carboxy-terminal anchor, for example but not limited to a transmembrane protein, and MPER-liposome conjugates. In certain embodiments, the MPER peptides of the invention bind 2F5 and 4E10 mAbs. In certain embodiments, compositions comprising these MPER peptides are expected to be immunogenic and provide a global population coverage in HIV-1 vaccination. In non-limiting embodiments, the immunogenic composition and vaccination methods comprise a combination of MPER peptide-liposomes as described herein.

Additional objects and advantages of the present invention will be clear from the description that follows.

In certain aspects the invention provides a composition comprising a peptide-liposome conjugate, wherein the peptide comprises a membrane proximal external region (MPER) epitope and a transmembrane anchor/linker. In certain embodiments, the linker is amphiphatic. In certain embodiments, the peptide is embedded in the liposome via the GTH linker. In certain embodiments, the composition comprises an adjuvant. In some embodiments, the adjuvant is alum. In other embodiments, the adjuvant is a TLR ligand. In some embodiments, the TLR4 adjuvant is Monophosphoryl Lipid A (MPLA) or synthetic TLR4 agonist, Glucopyranosyl Lipid Adjuvant (GLA). In certain aspects the invention provides a peptide-liposome conjugate comprising a TLR ligand, wherein the peptide comprises a membrane proximal external region (MPER) epitope and a transmembrane anchor/linker. Without being bound by theory, the anchor/linker is required for the 4E10 epitope region to adopt the proper helical structure, leading to antigen presentation. See Dennison et al. Journal of Virol. 83(19): 10211-10-223 (2009). The anchor/linker provides liposome anchorage of the MPER peptide, which anchorage induces helical structure of MPER peptides, resulting in enhanced binding of mAb 4E10. In non-limiting embodiments, the anchor/linker is a transmembrane domain, or an amphiphatic alpha-helix peptide. In certain embodiments, the peptide is synthetic or recombinantly produced. In certain embodiments, the peptide comprises two MPER epitopes.

In certain embodiments, the MPEP epitope is any one of SEQ ID NO: 3, 4, 5, 6, 7, 8, 18, 19, 20, 21, 22, 23, 24, 25, or any combination thereof. In certain embodiments, the peptide comprises or has SEQ ID NO: 9 (NEQELLELDK-WASLWNWFNITNWLWYIK), SEQ ID NO: 10 (NEQDL-LALDKWASLWNWFDISNWLWYIK), SEQ ID NO: 11 (NEKDLLALDSWKNLWNWFSITKWLWYIK), SEQ ID NO: 12 (NEQELLALDKWNNLWSWFDITNWLWYIR), or SEQ ID NO: 26 (CAP206_0moB5_MPER656 of the sequence NEKDLLALDSWKNLWNWFDITKWLWYIK). In certain embodiments, the peptide and compositions of the invention does not comprise the MPER epitopes of SEQ ID NOs: 1, 18, 2 and/or 22.

In certain embodiments, the transmembrane anchor/linker is at the carboxy-terminal of the peptide. In certain embodiments, the transmembrane anchor/linker is alpha-helical HIV-1 p24 gag sequence GTH1 (SEQ ID NO: 17 YKRWI-ILGLNKIVRMYS). In certain embodiments the anchor/linker is TMD peptide.

In certain embodiments, the peptide comprises or has SEQ ID NO: 13, 14, 15, or 16.

In certain embodiments, the TLR is a TLR 9 ligand. In certain embodiments, the TLR 9 ligand is oligo CpG. In certain embodiments, the TLR ligand is a TLR 7/8 ligand. In certain embodiments, wherein the TLR 7/8 ligand is R-848. In certain embodiments, the TLR ligand is a TLR 4 ligand. In certain embodiments, the TLR 4 ligand is monophosphorylipid A.

In certain embodiments, the conjugate comprises a TLR 9 ligand and a TLR 7/8 ligand. In certain embodiments, the TLR 9 ligand is oligo CpG and the TLR 7/8 ligand is R-848. In certain embodiments, the conjugate comprises a TLR 9 ligand and a TLR 4 ligand. In certain embodiments, the TLR 9 ligand is oligo CpG and the TLR 4 ligand is R-848. In certain embodiments, the conjugate further comprises interferon-.alpha. encapsulated therewithin.

In certain aspects, the invention provides a pharmaceutical composition comprising a synthetic peptide-liposome conjugate as described herein, or any combination thereof. In certain embodiments, the compositions of the invention are immunogenic. In certain embodiments the compositions comprise an adjuvant.

In certain embodiments, the composition further comprises a synthetic peptide-liposome complex comprising a peptide of SEQ ID NO: 9 or 13. In certain embodiments, the composition comprises the peptides of SEQ ID NOs: 9, and 10. In certain embodiments, the composition comprises the peptides of SEQ ID NOs: 9, 10 and 11. In certain embodiments, the composition comprises the peptides of SEQ ID NOs: 9, 10, 11 and 12. In certain embodiments, the composition comprises the peptides of SEQ ID NOs: 13 and 14. In certain embodiments, the composition comprises the peptides of SEQ ID NOs; 13, 14, and 15. In certain embodiments, the composition comprises the peptides of SEQ ID NOs; 13, 14, 15 and 16. In certain embodiments, the compositions of the invention consist essentially of any one of or any combination of the MPER liposomes described herein. In certain embodiments, the compositions of the invention are immunogenic.

In certain aspects, the invention provides a method of inducing an immune response in a subject, the method comprising administering to the subject any one of the inventive compositions in an amount sufficient to induce the immune response, wherein in certain embodiments the response comprises induction of anti-HIV-1 antibody. In certain aspects, the invention provides a method of inducing an anti-HIV-1 antibody in a subject, the method comprising administering to the subject any one of the inventive compositions in an amount sufficient to induce the anti-HIV-1 antibody. In certain embodiments of the methods, the composition is administered as a prime or/and a boost. In certain aspects, the composition is administered as a prime followed by the same or a different composition as a boost. In certain embodiments, the composition is administered as a boost following a prime of another suitable antigen.

In certain embodiments of the methods, the antibody binds an epitope comprised in the peptides of SEQ ID NOs: 9, 10, 11, 12, 13, 14, 15, 16, 26, 27 or any combination thereof. In certain embodiments, the antibody does not bind SEQ ID NO: 9 or 13. In certain embodiments, if the antibody binds SEQ ID NO: 9 and/or 13, then the antibody also binds to SEQ ID NOs: 10, 11, 12, 14, 15, and/or 16.

In certain embodiments of the methods, the antibody binds a nominal epitope of SEQ ID NOs: 1, 3, 5, 7, 18, 19, 20, 21 or any combination thereof. In certain embodiments, the antibody does not bind SEQ ID NO: 1, 18 and/or 5. In certain embodiments, the antibody binds a nominal epitope of SEQ ID NO: 1, 3, 7, 18, 19, 20, and/or 21.

In certain embodiments of the methods, the antibody binds a nominal epitope of SEQ ID NOs: 2, 4, 6, 8, 22-25 or any combination thereof. In certain embodiments, the antibody does not bind SEQ ID NO: 2 or 22. In certain embodiments, the antibody binds a nominal epitope of SEQ ID NO: 2, 4, 6, 8, 22-25 or any combination thereof. In certain embodiments, if the antibody binds SEQ ID NO: 2 or 22, it also binds to SEQ ID NO: 4, 6, 8, 23-25, or any combination thereof.

In certain aspects, the invention provides a synthetic peptide comprising SEQ ID NO: 3, 5, 7, 4, 6, 8, 18-24, or any combination thereof. In certain aspects, the invention provides a synthetic peptide comprising SEQ ID NO: 9, 11, or 12. In certain aspects, the invention provides a synthetic peptide comprising SEQ ID NO: 14, 15, or 16. Peptide length can be from 28-45, 28-50, 28-55, 28-60, 26-65, 28-70, 28-75, 28-80, 28-85, 28-90, 28-100, 28-110, 28-120, 28-130, 28-140, 28-150, or 45-50, 45-55, 45-60, 26-65, 45-70, 45-75, 45-80, 45-85, 45-90, 45-100, 45-110, 45-120, 45-130, 45-140, 45-150 amino acids long.

In certain embodiments, the liposome comprises a viral membrane lipid or an anionic lipid. In certain embodiments, the anionic lipid is phosphatidylserine. In certain embodiments, the anionic lipid is phosphatidic acid. In certain embodiments, the anionic lipid is cardiolipin.

In certain embodiments, the viral membrane lipid is sphingolipid or cholesterol.

In certain embodiments, the liposome comprises POPC (1-Palmitoyl-2-Oleoyl-sn-Glycero-3-Phosphocholine), POPE (1-Palmitoyl-2-Oleoyl-sn-Glycero-3-Phosphoethanolamine DMPA (1,2-Dimyristoyl-sn-Glycero-3-Phosphate), Cholesterol, or any combination thereof.

In certain embodiments, the liposome includes POPC and 1-palmitoyl-2-oleoyl-sn-glycero-3-[phospho-L-serine] (POPS). In certain embodiments, the liposome includes POPC and POPS and lysophosphorylcholine (lysoPC). In certain embodiments, the liposome includes POPC and POPE and Sphingomyelin and Cholesterol. In certain embodiments, the liposome includes POPC, POPE, DMPA, Cholesterol, or any combination thereof. In certain embodiments, the liposome includes DOPC and cholesterol. In certain embodiments, the liposome includes DPPC, DPPG and cholesterol.

In certain embodiments, the peptide embedded in the liposome binds an MPER neutralizing antibody or a Fab fragment thereof in a two-step binding model. In certain embodiments, the MPER neutralizing antibody is 2F5 or 410E. In certain embodiments, the liposome presents the peptide comprising the MPER epitope in a native HIV-1 membrane environment.

In certain embodiments, the liposome comprises POPC. In certain embodiments, the liposome comprises POPE. In certain embodiments, the liposome comprises DMPE. In certain embodiments, the liposome comprises DMPE. In certain embodiments, the liposome comprises cholesterol. In certain embodiments, the liposome comprises POPC (1-Palmitoyl-2-Oleoyl-sn-Glycero-3-Phosphocholine), POPE (1-Palmitoyl-2-Oleoyl-sn-Glycero-3-Phosphoethanolamine), DMPA (1,2-Dimyristoyl-sn-Glycero-3-Phosphate), and Cholesterol.

BRIEF DESCRIPTION OF THE DRAWINGS

FIG. 6A. Comparison of normalized specific binding responses of 2F5 mAb to 2F5 peptide-liposomes (broken line) and L669S mutant peptide-liposomes (solid line). The inset shows the magnified image of the dissociation phase of the 2F5 mAb interaction (120-400 s). FIG. 6B. The encounter-docking model of 2F5 mAb-peptide-liposome interactions and the estimated rate constants of association and dissociation steps.

FIG. 9. Structures of TLR agonists formulated with liposomes. A schematic picture of the immunogen designs shows the peptide-liposomes containing different TLR agonists as adjuvants; TLR4 (Lipid A); TLR9 (oCpG (SEQ ID NO: 57)) and TLR7 (R848).

FIG. 10A shows strong binding of 2F5 mab to gp41 MPER liposome constructs with Lipid A (200 µg dose equivalent). FIG. 10B shows binding of 2F5 mAb to oCpG (50 µg dose equivalent) conjugated gp41 MPER liposomes. FIG. 10C shows binding of 2F5 mAb to R848-conjugated gp41 MPER containing liposomes. In comparison to control liposomes with only TLR adjuvants, strong binding of 2F5 mAb was observed to each of the gp41MPER-adjuvant liposomal constructs.

FIG. 12 IFNα encapsulated liposome with multiple TLR ligands. These constructs have the potential to provide synergy in B cell responses via dual TLR triggering.

FIG. 13. Crystal structures of 2F5 (Ofek et al, J. Virol. 78:10724 (2004)) and 4E10 (Cardoso et al, Immunity 22:163-173 (2005)) and design of mutations in the CDR H3 loop to eliminate binding to lipids and HIV-1 viral membrane.

FIG. 15. Neutralization of QZ4734 and QZ4734/L669S pseudotyped viruses by 2F5 mAb (tested on TZM-b1 cells).

QZ4734/L669S was generated by introducing L669S single mutation into the QZ4734 envelope. Numbers by the curves indicate the IC50 values.

FIG. 16. Neutralization of TND-669S and two other stains (7534.2 and 7534.11) isolated from the same plasma sample (15 mo post infection) by 2F5 and TriMab (1:1:1 combination of 2F5, 4E10 and 2G12). Numbers above each bar represents IC50 values. The test was performed on TZM-b1 cells.

FIG. 17. Induction of gp41MPER specific antibody responses in guinea pigs immunized with MPER liposomal immunogens (SEQ ID NO: 41).

FIG. 18. Induction of gp41 MPER specific antibody responses in Non-human primates (NHP) immunized with MPER liposomal immunogens.

FIG. 19. Non-limiting embodiment of a design of MPER peptide-liposomes (SEQ ID NOS 17 and 9, respectively, in order of appearance). In non-limiting embodiments, the pepide-liposome comprises a TLR1 antagonist.

FIG. 20 Non-limiting embodiment of a design of MPER peptide-liposomes. In a non-limiting embodiment, synthetic MPER peptide-liposomes were constructed as described in Alam et al, J. Immunol. 178:4424-4435 (2007). MPER peptides (SEQ ID NOS 13-16, respectively, in order of appearance) were synthesized, and in a non-limiting embodiment were conjugated at their carboxyterminal end to the a-helical HIV-1 p24 gag sequence GTH1 (YKRWI-ILGLNKIVRMYS (SEQ ID NO: 17)) and served as a membrane anchor tag. GTH1 sequence is shown as a rectangle and MPER peptide as colored strands. In non-limiting embodiments, the pepide-liposome comprises a TLR1 antagonist.

FIG. 21 Binding of BNAb 2F5 and 4E10 to MPER peptide-liposomes described in FIGS. 19-20. Synthetic MPER peptide-liposomes complexed to the indicated MPER peptide and TLR adjuvants (R848, Lipid A) were anchored on a BIAcore sencor ship (L1) and each mAb (2 μg/mL) injected over the surface. Binding shown is after subtraction of non-specific signal measured on a control liposome surface. The lack of binding of 2F5 mAb to MPER656.2 is likely due to D to S mutation in the core epitope (DKW) of the bNAb 2F5.

FIGS. 22A and 22B show MPER antibody signatures in the peptide regions. The figure illustrates one embodiment of a polyvalent vaccine. The signature amino acids that are associated with susceptible and resistant Envs mapped onto a global diversity LOGO. Illustrated is other design input information regarding global variation. The most common forms of the key epitope regions in different clades are noted, contact residues are also indicated. There are a few other signatures outside of the MPER region that may have to do with accessibility when trying to open up the MPER on a membrane bound trimer. FIG. 22A discloses SEQ ID NOS 9-12, respectively, in order of appearance. FIG. 22B discloses SEQ ID NOS 1, 1, 3, 5, 58-62, 62-63, 23-24, 64, 22 and 65, respectively, in order of appearance.

FIG. 23 shows logos for the population, and logos spanning the epitopes by clade. The difference in variation levels in certain positions in one clade versus another suggests there may be different immune pressures and subtle differences in targets in the different clades. Figure discloses MPER656 peptide as SEQ ID NO: 9.

FIG. 24 Difference in 6-mer coverage by position of the original MPER656 peptide ("NEQELLELDKWASLWN-WFNITNWLWYIK" disclosed as SEQ ID NO: 9) and—four valent vaccine comprising peptides of FIG. 22. FIG. 24 shows 6-mer coverage of the region for the single peptide vaccine and the four-valent vaccine shown in FIG. 22. Left panels: The increase in population coverage is seen as the amount of red under the "ridge line" with the four-valent design. Illustrated for both the whole peptide, including nearby overlapping epitopes, and for the 2F5 and 4E10 core 6 mers ("ELDKWA" disclosed as SEQ ID NO: 45 and "NWFNIT" disclosed as SEQ ID NO: 2), which are highlighted along the ridge in a little yellow box, and summarized that the bottom in text. There is very good identity coverage all 6 mers, in this region, even globally. The four-peptide vaccine design, essentially covers the whole population at a 5/6 match-level of conservation. In the right panel, each row is one of the 121 sequences. They display the level of matches across each single amino acid in the alignment—black and dark red is low level of matches, yellow is lots of perfect matches, light orange is good. The 4E10 region has a lot of variation, but it is tolerated by 4E10 and 10E8, the 2F5 region has extensive variation in many sequences, and the variation is poorly tolerated by 2F5. In the right panels: 6-mer coverage of the NSDP global alignment of the region spanning MPER656 peptide vaccine, colored according to potential epitope (6-mer) coverage by the original vaccine, or the polyvalent set of four. Each colored square represents an amino acid. Each "row" is a sequence, each column is an alignment position. Each amino acid is colored according to the set of 6-amino-acid strings that contain it: if all 6-mers that overlap with an amino acid are perfectly matched in a test vaccine or peptide set, then the amino acid is colored yellow, and epitopes encompassing that are likely to be highly cross reactive; increasingly red values indicate fewer and fewer matches in the overlapping set of 6-mers that span the amino acid; amino-acid residues that are not included in any antigen/peptide matched set 6-mer are colored black.

FIG. 25 shows immunization protocol for NHP#22 (Example 7).

Figure 26:
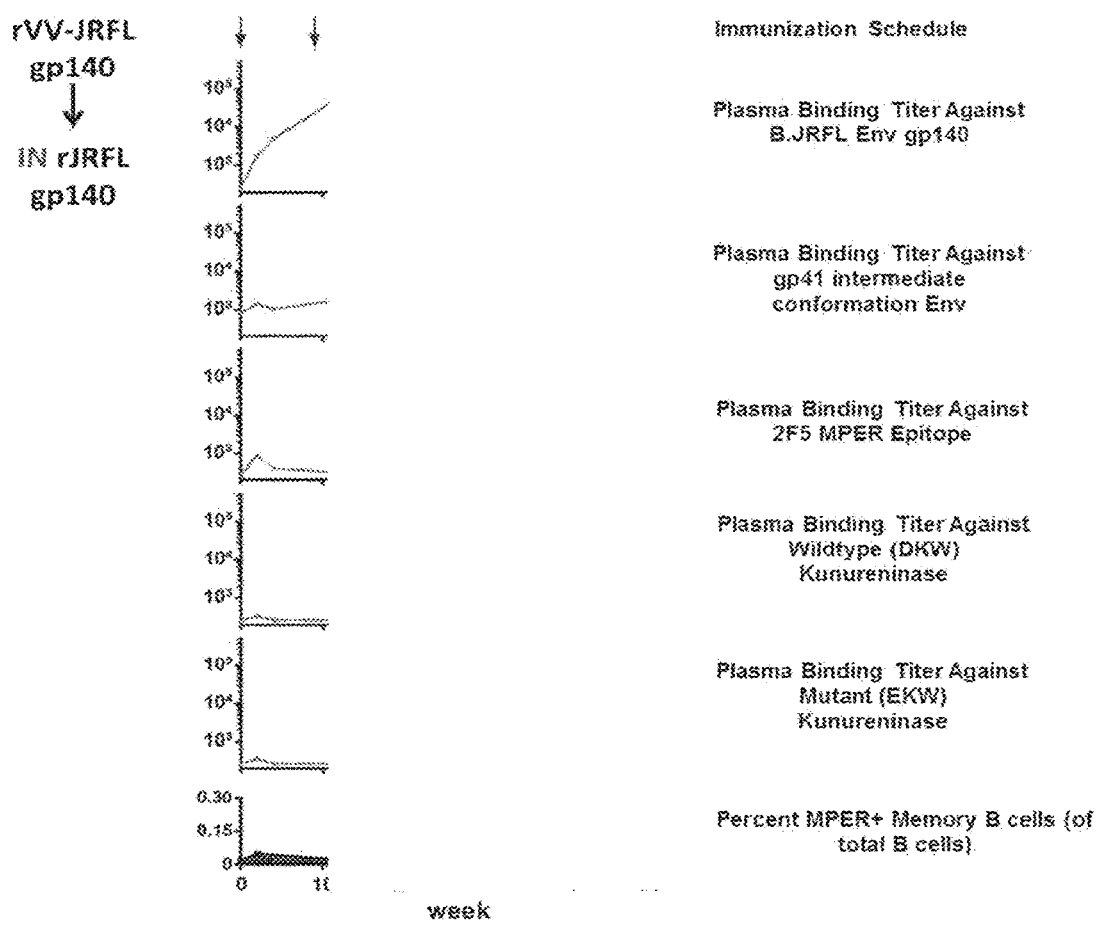

FIG. 26 shows immunization protocol for NHP#22 (Example 7).

FIG. 27 shows immunization protocol for NHP#22 (Example 7).

Figure 28:
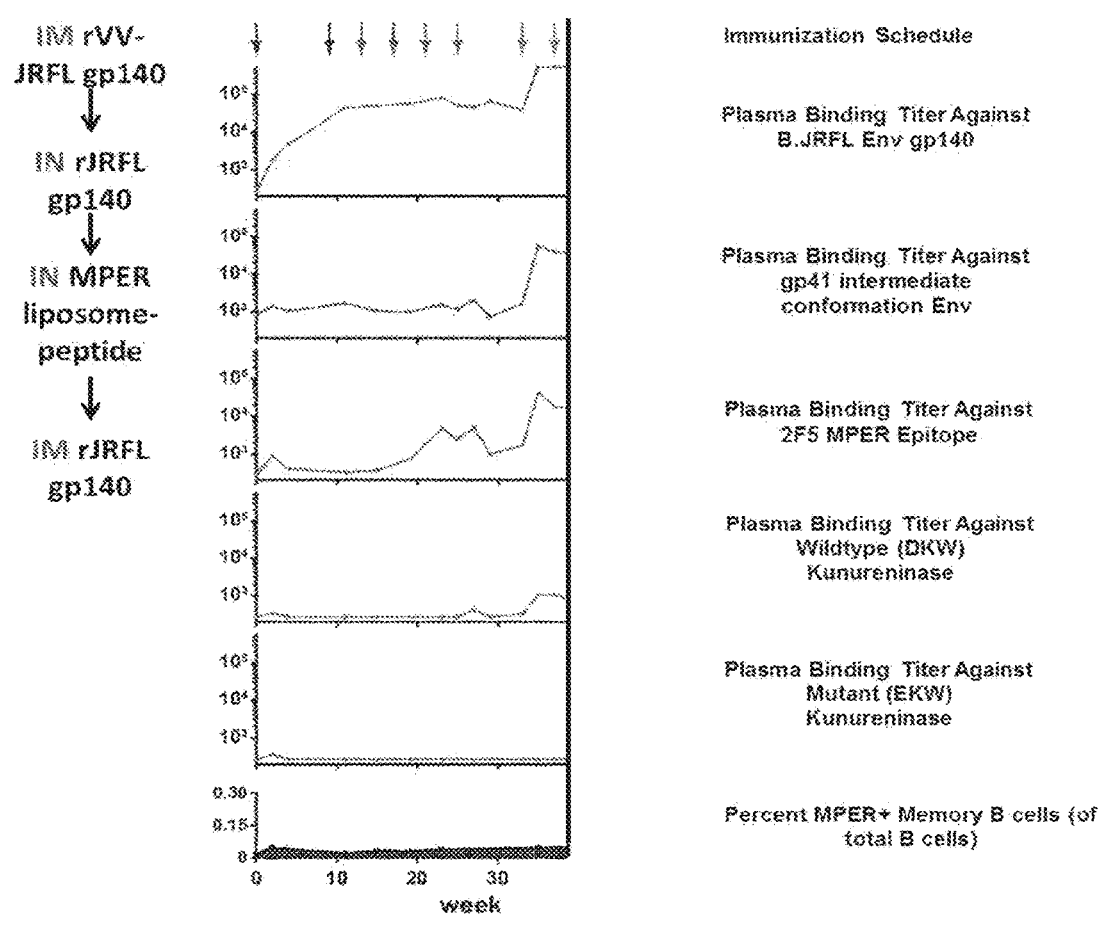

FIG. 28 shows immunization protocol for NHP#22 (Example 7).

FIG. 29 shows that vaccination of 2F5 complete KI mice with TLR-MPER peptide-lipids (MPER peptide disclosed as SEQ ID NO: 9) awakens anergic peripheral B cells and induces clinically-relevant titers of serum broadly neutralizing antibodies targeted at the 2F5 gp41 DKW epitope.

FIG. 30 shows immunization protocol for NHP#22 (Example 7).

FIG. 31A shows Footprints of 2F5 UCA and mature 2F5 antibodies by Alanine scanning (SEQ ID NOS 66 and 66, respectively, in order of appearance). FIG. 31B shows Epitope mapping of NHP #22-animal 585-derived antibodies (SEQ ID NOS 67, 67 and 41, respectively, in order of appearance).

FIG. 32 shows Tree and Reactivity of Clonal Lineage CL900364 Antibodies.

FIG. 33 shows Tree and Reactivity of Clonal Lineage CL900364 Antibodies.

FIG. 34 shows Kyte-Doolittle Hydrophobicity Plot of Rhesus Monkey #22 MPER-reactive Mabs.

FIG. 35 shows Rhesus DH249 Clonal Lineage.

FIG. 36 shows VH Alignment of Rhesus DH249 Clonal Lineage Antibodies (SEQ ID NOS 68-71, respectively, in order of appearance). DH 249 VH % mutation=5%; DH 250 VH % mutation=7%; DH 251 VH % mutation=9%

Figure 37:
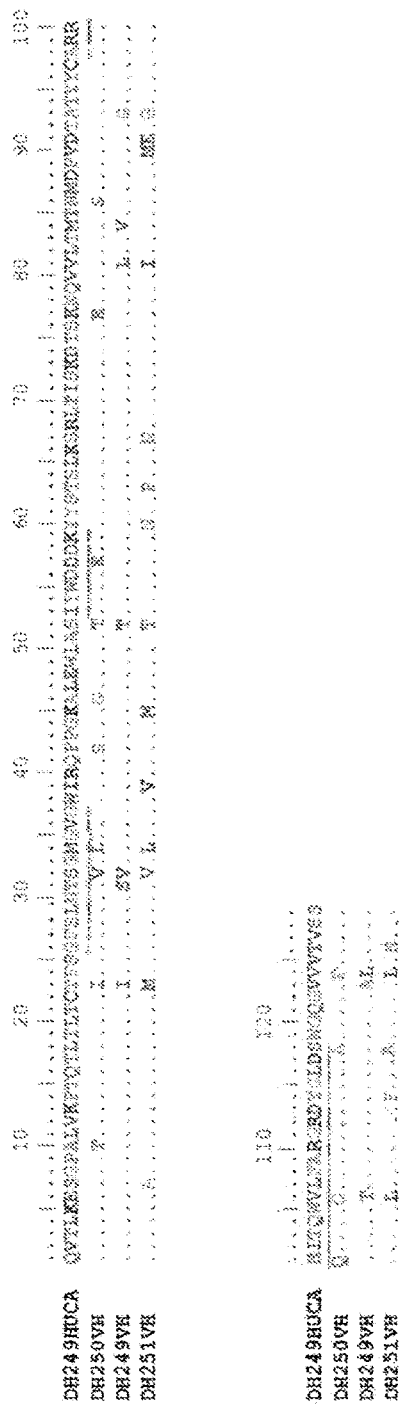

FIG. 37 shows Amino Acid Alignment of Rhesus DH249 2F5-Like Clonal Lineage (SEQ ID NOS 72-75, respectively, in order of appearance). DH 249 VH % mutation=5%; DH 250 VH % mutation=7%; DH 251 VH % mutation=9%.

Figure 38:
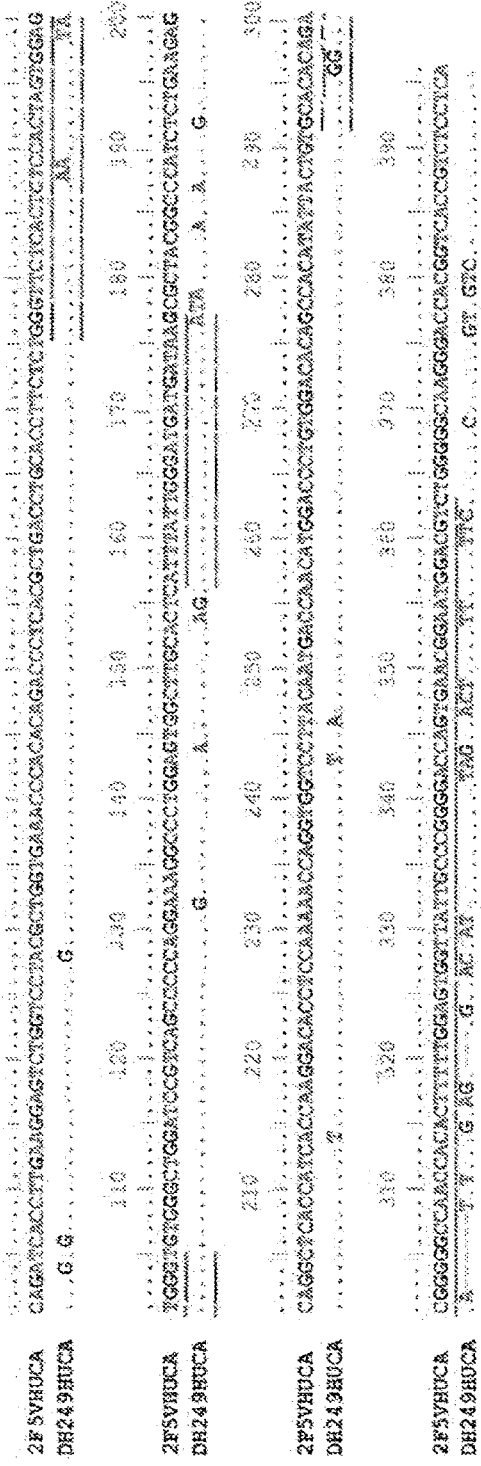

FIG. 38 shows Comparison of 2F5 BnAb VH2-5 UCA (SEQ ID NO: 76) with Rhesus DH249 Clonal Lineage VH2-55 UCA (SEQ ID NO: 68). 85% identity of between 2F5 BnAb VH2-5 UCA and rhesus; DH249 VH2-55 UCA; Rhesus VH2-55 is the orthologue of human VH2-5.

Figure 39:
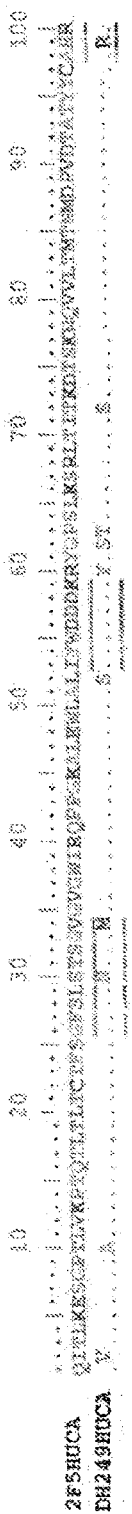

FIG. 39 shows Amino Acid Alignment of Human BnAb 2F5 VH2-5 UCA (SEQ ID NO: 77) with Rhesus DH249 VH2-55 UCA (SEQ ID NO: 72). UCA for 2F5 is 93% identical at the nucleotide level to the DH249 rhesus UCA through the VH region. In the HCDR3 and JH region, there is 70% identity between the two. For the entire VHDJH, there is 80% identity between the two.

Figure 40:
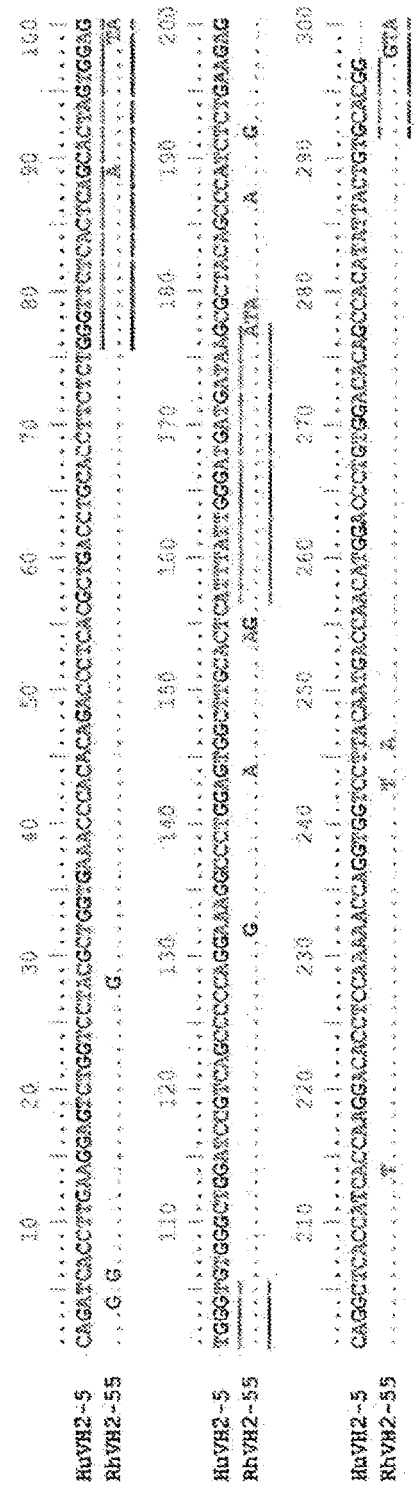

FIG. 40 shows Comparison of Germline V Region of Human VH2-5 (SEQ ID NO: 78) with Germline V Region of Rhesus VH2-55 of Rhesus DH249 (SEQ ID NO: 79) Clonal Lineage. 93% identity between human VH2-5 and rhesus VH2-55.

Figure 41:
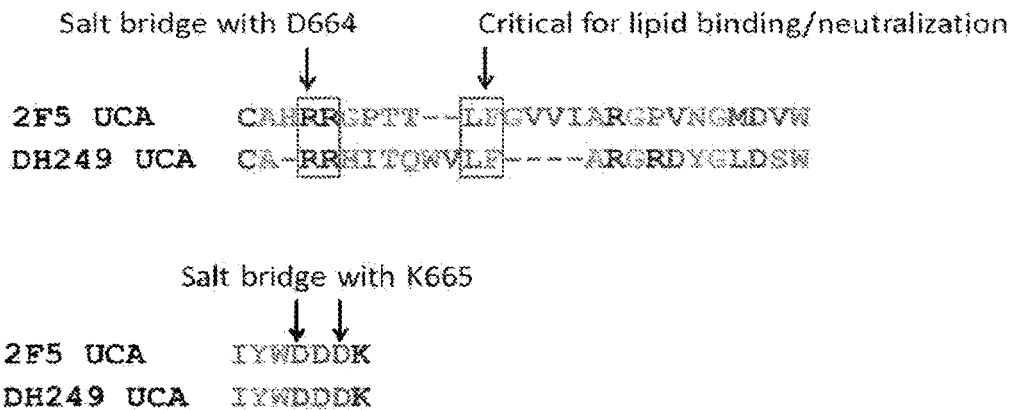

FIG. 41 shows Amino Acid Alignment of Human BnAb 2F5 UCA HCDR 3 (SEQ ID NO: 80) with Rhesus DH249 UCA HCDR 3 (SEQ ID NO: 81).

Figure 42:
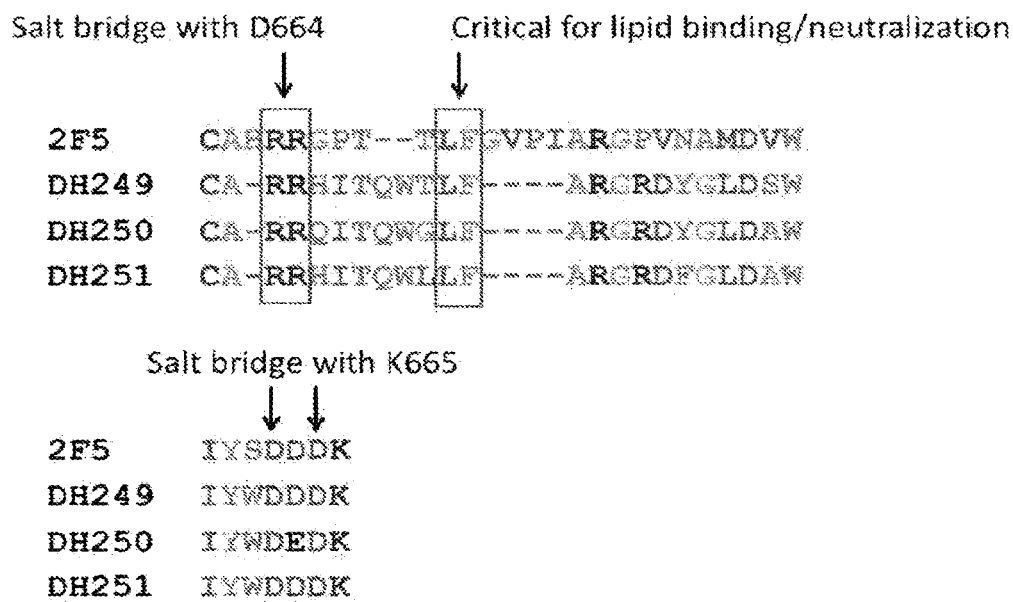

FIG. 42 shows Amino Acid Alignment of Human BnAb 2F5 HCDR3 with HCDR3 of Rhesus DH249 Clonal Lineage Antibodies (SEQ ID NOS 82-85, respectively, in order of appearance).

Figure 43:
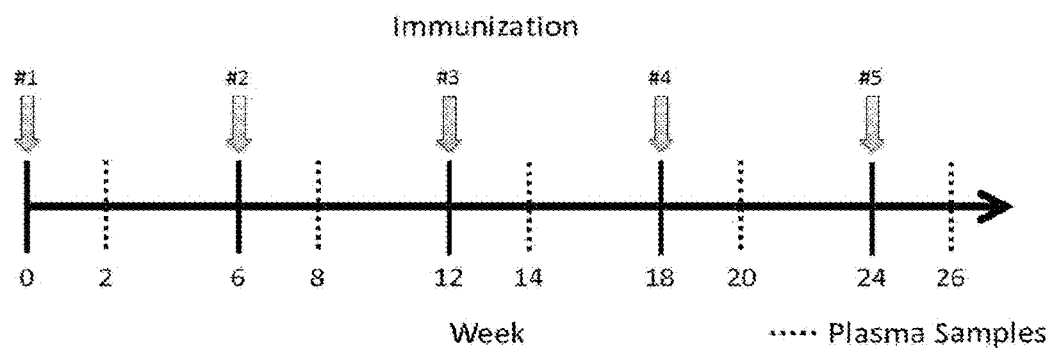
Figure 44A:
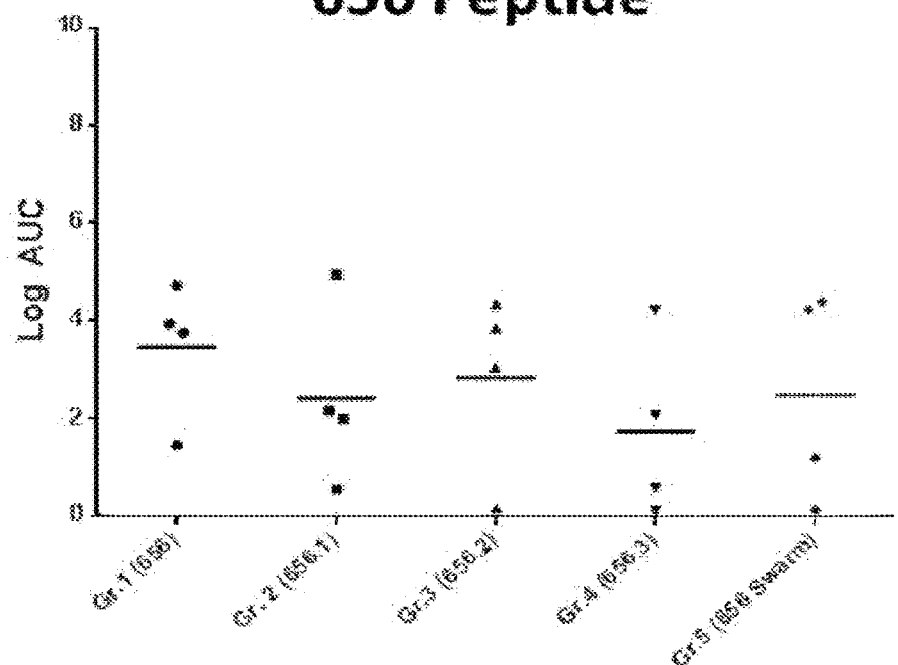
Figure 44B:
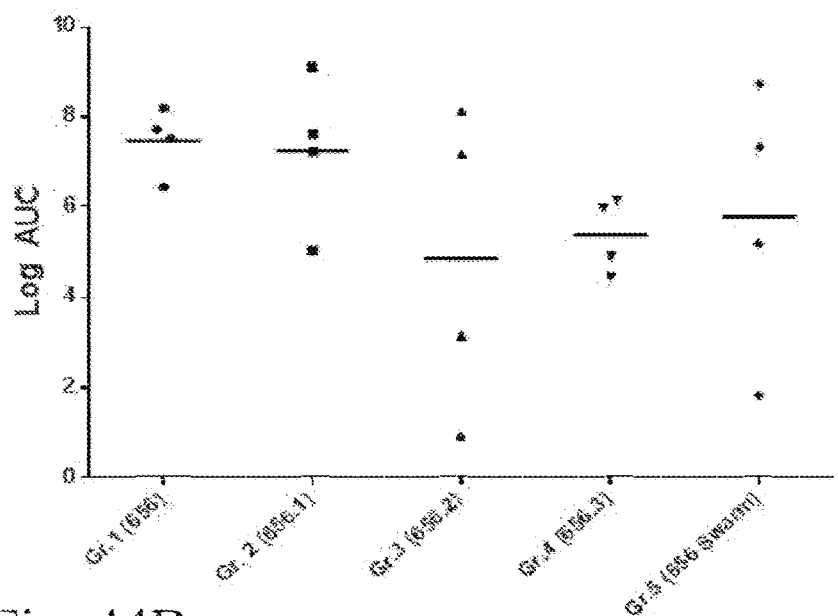
Figure 44C:
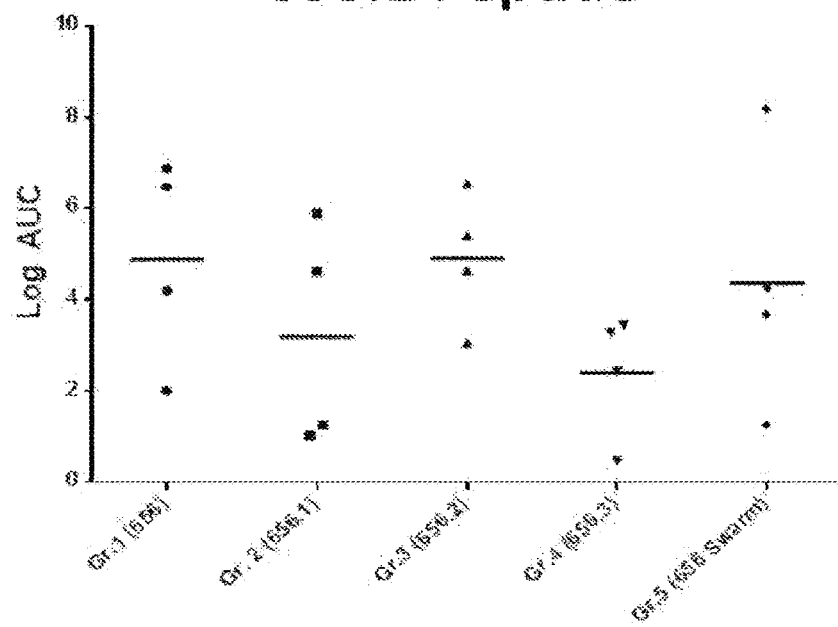
Figure 44D:
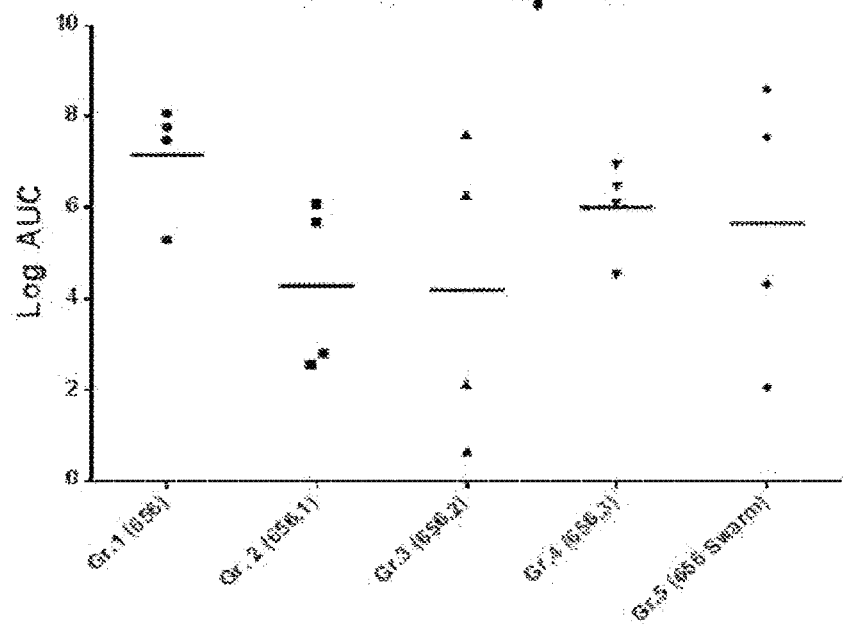
Figure 45A:
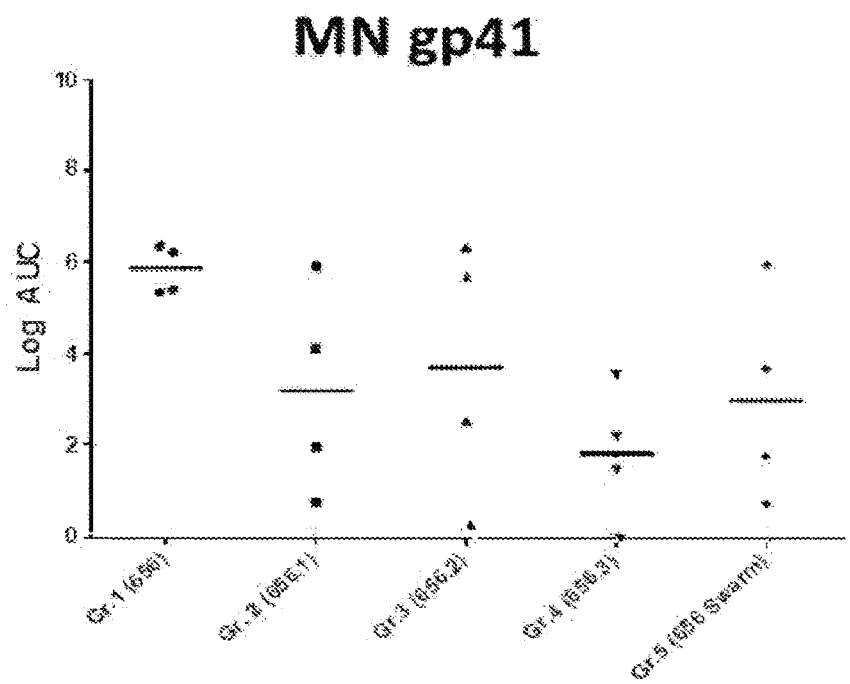
Figure 45B:
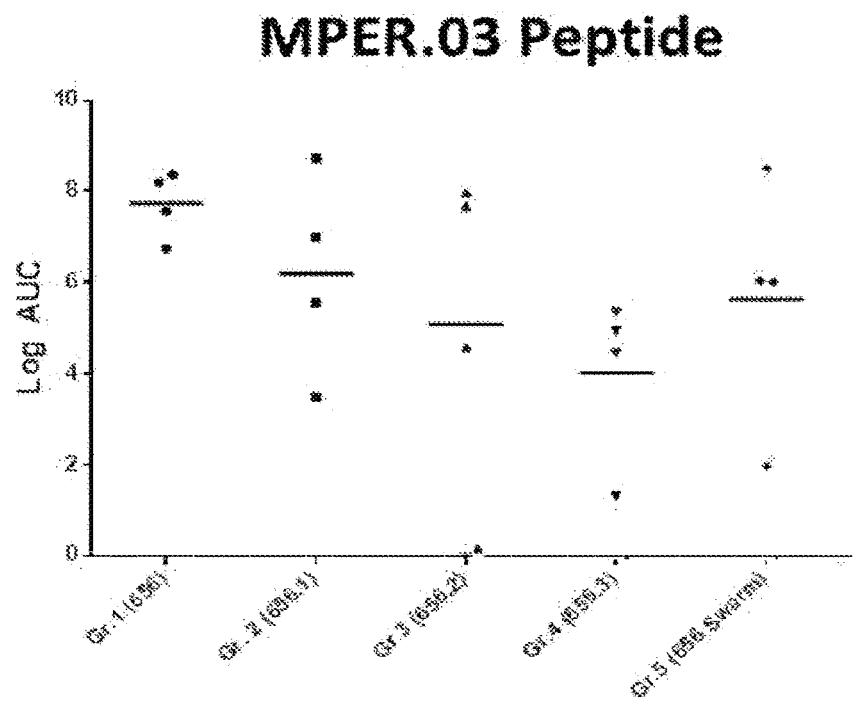
Figure 45C:
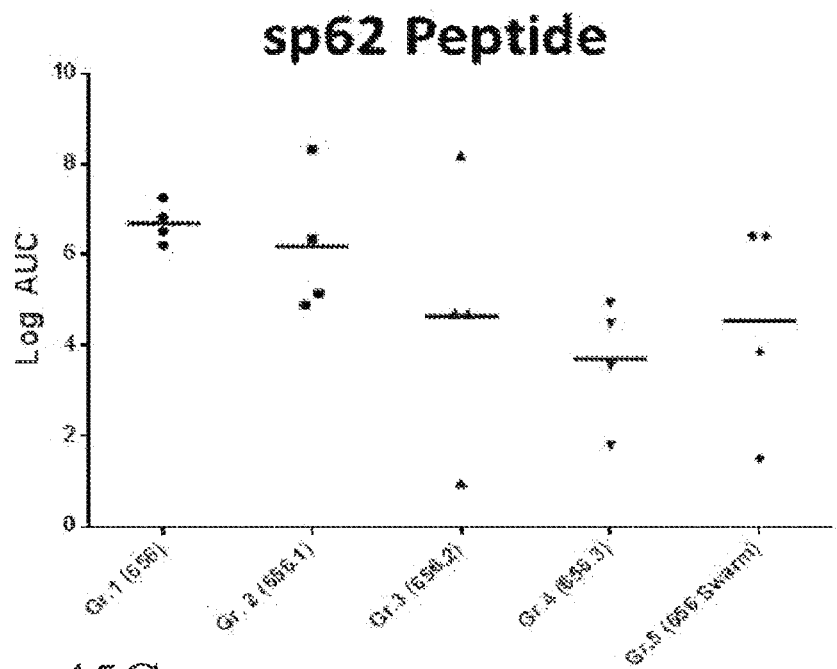
Figure 45D:
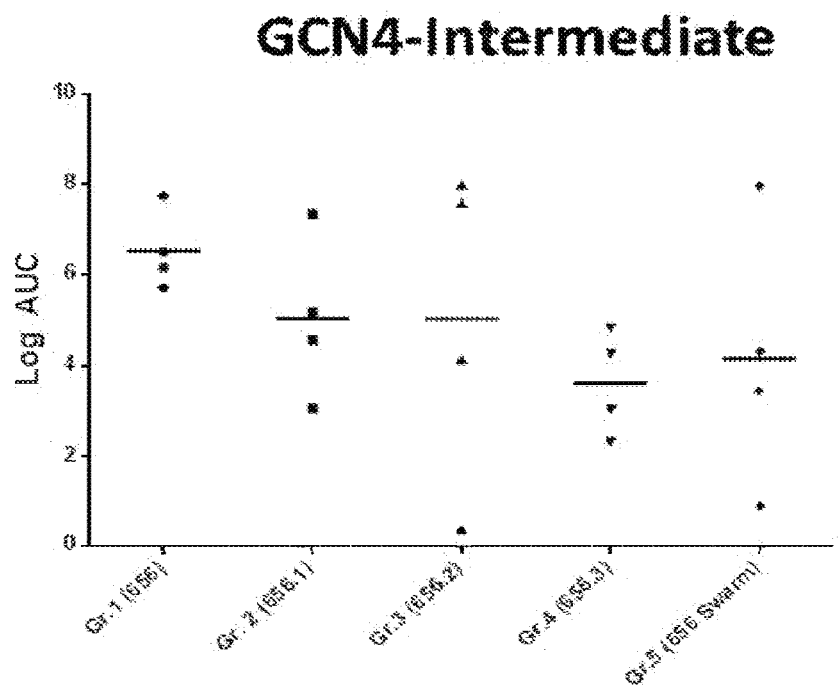

FIG. 43 shows MPER immunization strategy. Rhesus macaques were immunized in 5 groups for NHP#87 with the different MPER peptide liposomes. Group 5 animals were immunized with a swarm of all of the MPER peptide liposomes. 4 animals per group. NHP#91 was a study to compare two adjuvants. Group 1 had MPLA alone and Group2 had R848 alone. The immunogen for both groups was the original MPER656 peptide liposome. The idea was to compare group 1 and 2 from this study to group 4 from NHP#87 where the animals received both MPLA and R848.

FIGS. 44A-D show NHP#87 Week 20 plasma binding to immunogen peptide 656 (A), 656.1 (B), 656.2 (C), 656.3 (D) (for all panels pre-immune substracted). Isolated plasma at Week 20 was screened for binding to each immunogen by ELISA. Plotted is the log area under the curve for binding for each individual monkey separated by group. Solid line indicates the average log AUC for each group. Animals in the group immunized with the original MPER656 peptide liposome have the best response to all of the immunogens.

FIGS. 45A-D shows NHP#87 Week 20 plasma binding to MPER specific proteins MNgp41 (A), MPER.03 peptide (B), sp62 peptide (C), GCN4 intermediate (D) (for all panels pre-immune substracted). NHP#87 Isolated plasma at Week 20 was screened for binding to each MPER minimal epitopes by ELISA. Plotted is the log area under the curve for binding for each individual monkey separated by group. Solid line indicates the average log AUC for each group. MN gp41 is the whole gp41 from the clade B MN sequence, MPER.03 is a consensus MPER peptide, SP62 is a minimal MPER region that has only the 2F5 epitope, and the GCN4-intermediate is a protein that mimics the prefusion state of the env. Animals in the group immunized with the original MPER656 peptide liposome have the best response to all of the MPER regions.

Figure 46A:
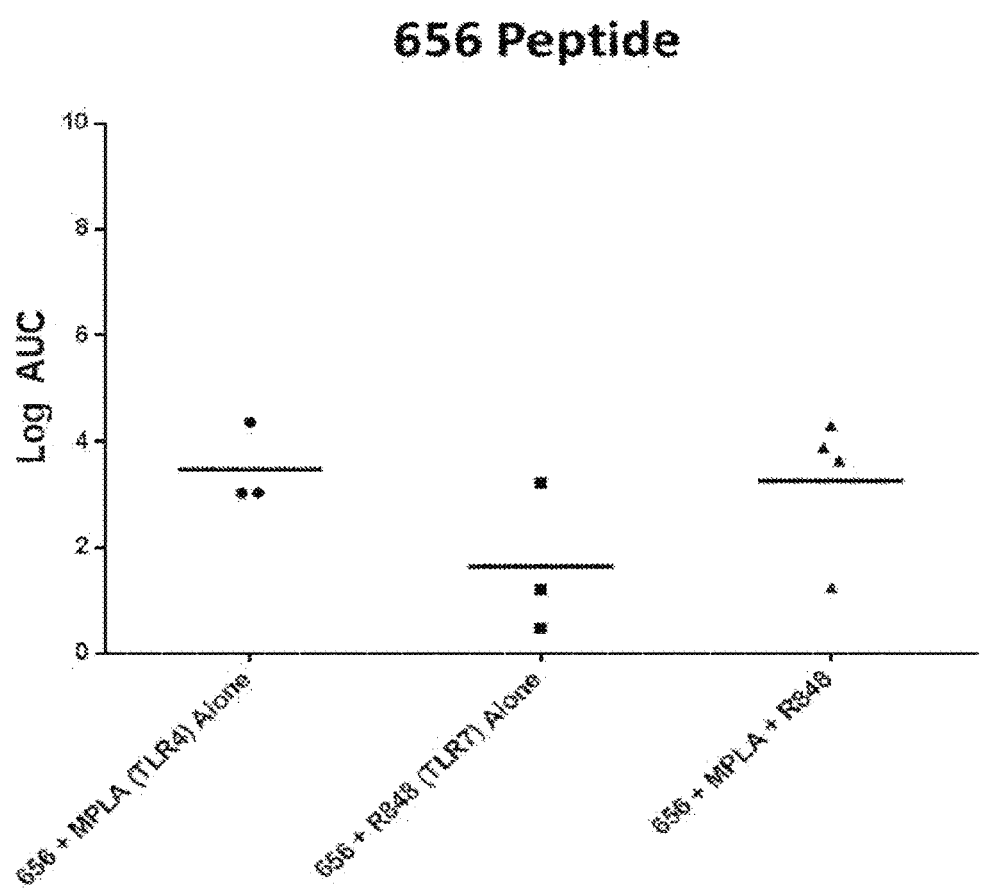
Figure 46B:
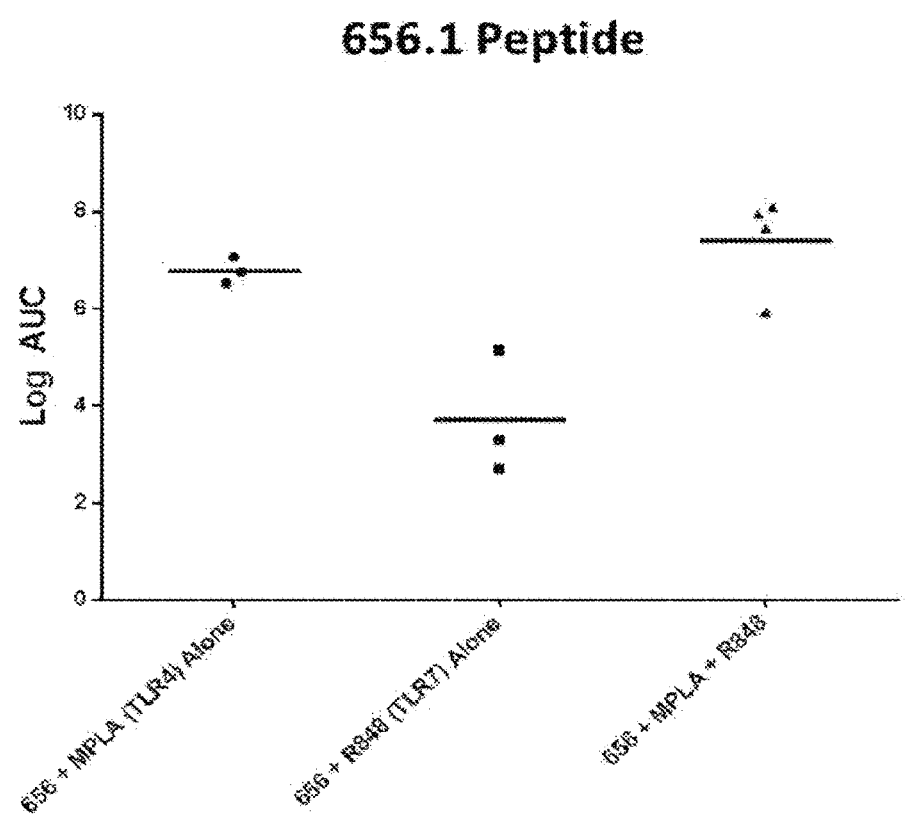
Figure 47A:
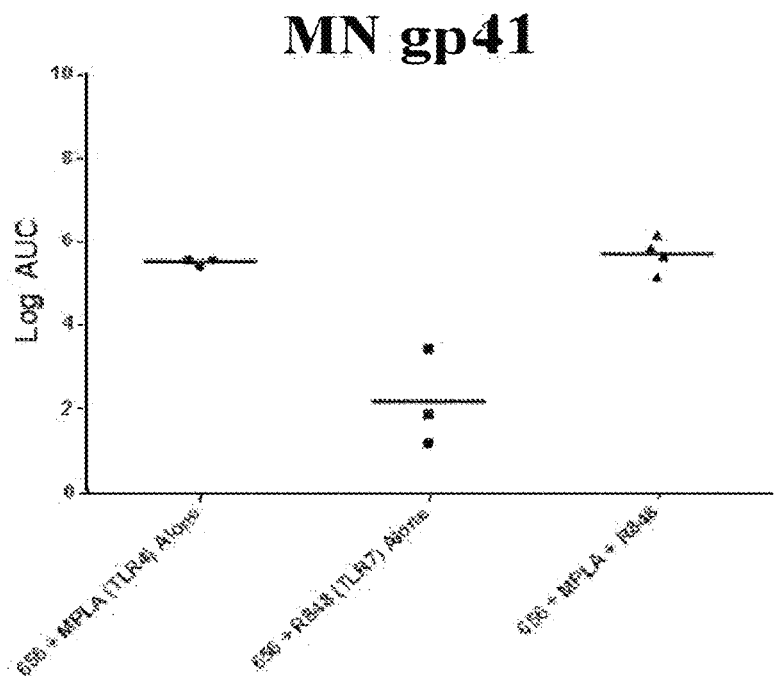
Figure 47B:
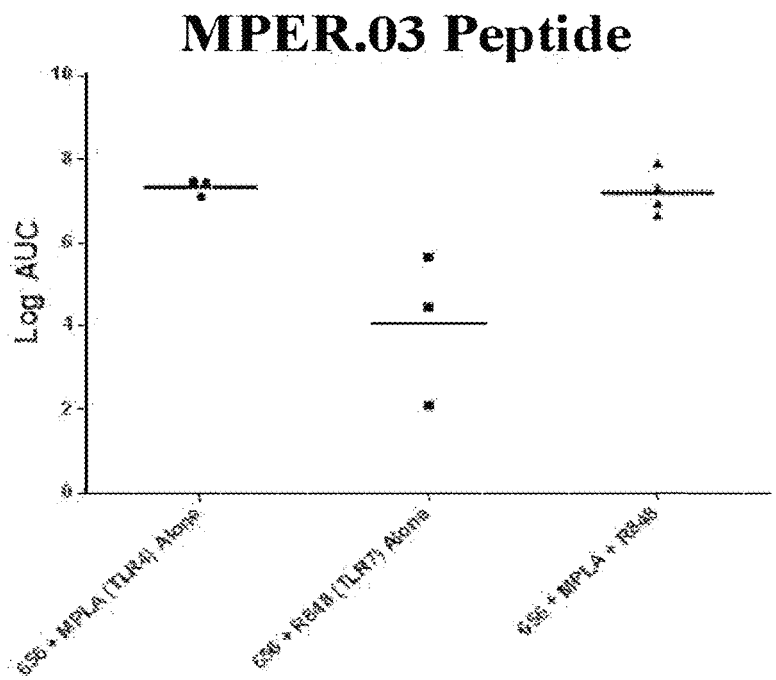
Figure 47C:
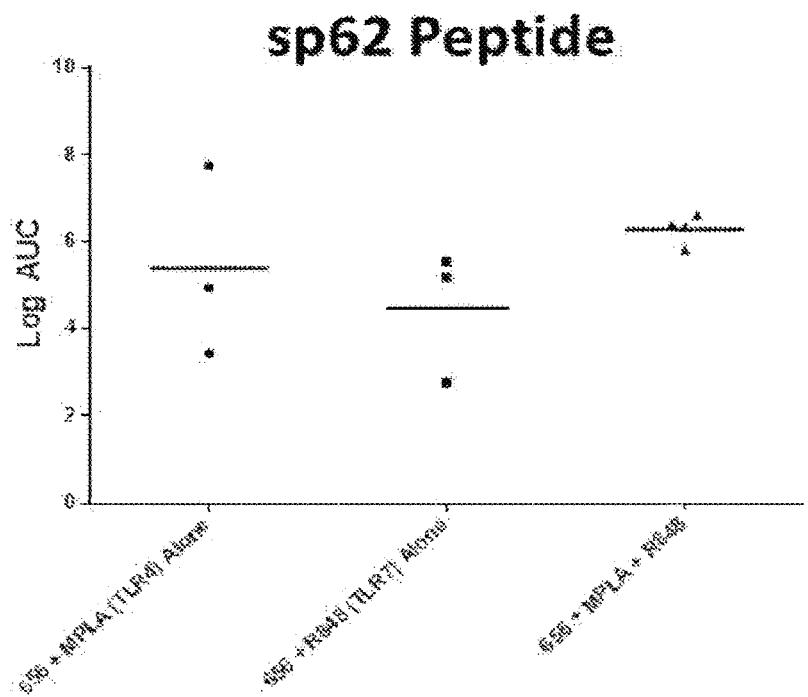
Figure 47D:
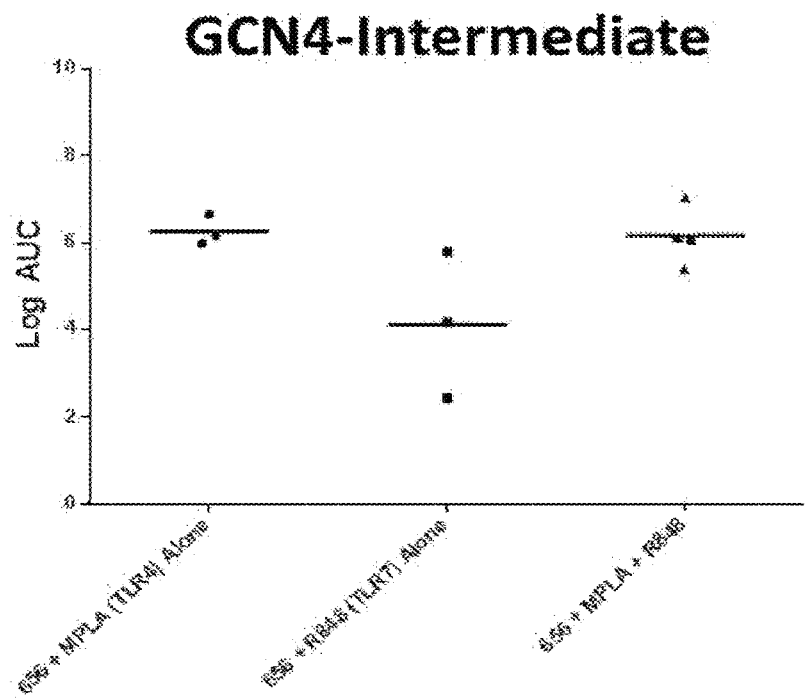

FIGS. 46A-B shows NHP #91 Week 14 Plasma Binding to Immunogen Peptides (for all panels pre-immune substracted). NHP#91 and last group (656+MPLA+R848) is group 4 of NHP#87; Isolated plasma at Week 14 was screened for binding to each immunogen by ELISA. Plotted is the log area under the curve for binding for each individual monkey separated by group. Solid line indicates the average log AUC for each group. Under these immunization conditions and amounts of adjuvants, MPLA seems to be better than R848 and both together give similar esults as MPLA alone.

FIGS. 47A-D shows NHP#91 Week 14 Plasma Binding to MPER-Specific Proteins. NHP#91 and last group (656+ MPLA+R848) is group 4 of NHP#87 (for all panels pre-immune substracted); Isolated plasma at Week 14 was screened for binding to each immunogen by ELISA. Plotted is the log area under the curve for binding for each individual monkey separated by group. Solid line indicates the average log AUC for each group. Under these immunization conditions and amounts of adjuvants, MPLA seems to be better than R848 and both together give similar results as MPLA alone.

FIG. 48 shows NHP #87 and NHP #91 Neutralization WK20. The results show that there is no neutralization of HXB2, MN.3, or W61 D.71 in either TZMb1 or FCRg cell lines.

DETAILED DESCRIPTION OF THE INVENTION

The present invention relates to a liposome-based adjuvant conjugate that presents TLR ligands and HIV-1 gp41 neutralizing antigens, and to a method of inducing neutralizing anti-HIV-1 antibodies in a subject (e.g., a human subject) using same. Suitable neutralizing antigens include gp41MPER epitope peptides (Armbruster et al, J. Antimicrob. Chemother. 54:915-920 (2004), Stiegler and Katinger, J. Antimicrob. Chemother. 512:757-759 (2003), Zwick et al, Journal of Virology 79:1252-1261 (2005), Purtscher et al, AIDS10:587 (1996)) and variants thereof, for example, variants that confer higher neutralization sensitivity to MPER Mabs 2F5 and 4E10. In certain embodiments, the variant is a MPER epitope peptide with an L669S mutation that confers higher neutralization sensitivity to MPER mAbs 2F5 and 4E10 (Shen et al, J. Virology 83: 3617-25 (2009)).

Liposomes suitable for use in the invention include, but are not limited to, those comprising POPC, POPE, DMPA (or sphingomyelin (SM)), DMPE, lysophosphorylcholine, phosphatidylserine, cholesterol (Ch), or any combination thereof. While optimum ratios can be determined by one skilled in the art, examples include POPC:POPE (or POPS):SM:Ch or POPC:POPE (or POPS):DMPA:Ch at ratios of 45:25:20:10. Alternative formulations of liposomes that can be used include DMPC (1,2-dimyristoyl-sn-glycero-3-phosphocholine) (or lysophosphorylcholine), cholesterol (Ch) and DMPG (1,2-dimyristoyl-sn-glycero-3-phoshpho-rac-(1-glycerol) formulated at a molar ratio of 9:7.5:1 (Wassef et al, ImmunoMethods 4:217-222 (1994); Alving et al, G. Gregoriadis (ed.), Liposome technology 2nd ed., vol. III CRC Press, Inc., Boca Raton, Fla. (1993); Richards et al, Infect. Immun. 66(6):285902865 (1998)). The above-described lipid compositions can be complexed with lipid A and used as an immunogen to induce antibody responses against phospholipids (Schuster et al, J. Immunol. 122:900-905 (1979)). In certain embodiments, a formulation comprises POPC:POPS:Ch at ratios of 60:30:10 complexed with lipid A according to Schuster et al, J. Immunol. 122:900-905 (1979). In certain embodiments, the liposomes can be pegylated. In these embodiments the liposomes comprise DMPE.

The liposomes can comprise the following phospholipids, POPC (1-Palmitoyl-2-Oleoyl-sn-Glycero-3-Phosphocholine), POPE (1-Palmitoyl-2-Oleoyl-sn-Glycero-3-Phosphoethanolamine), DMPA (1,2-Dimyristoyl-sn-Glycero-3-Phosphate), DOPE (1,2-Dioleoyl-sn-Glycero-3-Phosphatidylethanolamine) Cholesterol, or any combination thereof. For liposome preparation these lipids can be dissolved in chloroform (purchased from Avanti Polar Lipids (Alabaster, Ala.).).

Synthetic liposomes can be prepared by dispensing appropriate molar amounts of phospholipids in one embodiment the ratio is (POPC:POPE:DMPA:Ch=45:25:20:10)

Peptide-lipid conjugates. Each of these peptides can be incorporated into synthetic liposomes of varying composition which include:

i) POPC:POPE:DMPA:Cholesterol
ii) POPC:POPS
iii) POPC:POPS:lysoPC
iv) POPC:POPE:Sphingomyelin:Cholesterol
v) POPC:Cholesterol:POPE:DMPA
vi) POPC:Cholesterol:POPE:DMPE The liposome composition could comprise an adjuvant. In non-limiting embodiments the adjuvant is alum or monophosphoryl Lipid A (Avanti Polar Lipids).

The peptide-liposome immunogens of the invention can be formulated with, and/or administered with, adjuvants such as lipid A, oCpGs, TLR4 agonists or TLR 7 agonists that facilitate robust antibody responses (Rao et al, Immunobiol. Cell Biol. 82(5):523 (2004)). Non-limiting examples of other adjuvants that can be used include alum and Q521 (which do not break existing B cell tolerance). In certain embodiments, formulations comprise an adjuvant that is designed to break forms of B cell tolerance, such as oCpGs in an oil emulsion such as Emulsigen (an oil in water emulsion) (Tran et al, Clin. Immunol. 109(3):278-287 (2003)).

In accordance with the invention, immune response enhancing TLR ligands, for example, monophosphorylipid A (MPL-A, TLR4 ligand), oligo CpG (TLR 9 ligand) and R-848 (TLR 7/8 ligand), are formulated either individually or in combination into liposomes conjugated with an HIV-1 gp41MPER peptide immunogen. In certain embodiments, the combination of TLR agonists comprises oCpG (TLR9) (Hemni et al, Nature 408:740-745 (2004)) and R848 (TLR7/8) (Hemni et al, Nat. Immunol. 3:196-200 (2002)).

Additional designs of constructs of the invention include MPER peptide-liposome encapsulated with the cytokine interferon (IFN)-$\alpha$ and either encapsulated or membrane bound CD40 ligand. Two broadly neutralizing gp41 MPER antibodies (2F5, 4E10) bind with high affinity to such TLR ligand adjuvant-associated liposome constructs. These constructs can be used to modulate B cell tolerance, direct liposomes to certain B cell populations capable of making broadly reactive neutralizing antibodies, and in enhance antibody responses against poorly immunogenic HIV-1 gp41MPER epitopes.

The peptide-liposome immunogens can be administered, for example, IV, intranasally, subcutaneously, intraperitoneally, intravaginally, or intrarectally. The route of administration can vary, for example, with the patient, the conjugate and/or the effect sought, likewise the dosing regimen.

Autoreactive B cells can be activated by TLR ligands through a mechanism dependent on dual engagement of the B cell receptor (BCR) and TLR (Leadbetter et al, Nature 416:603 (2002); Marshak-Rothstein et al, Annu. Rev. Immunol. 25: 419-41 (2007), Herlands et al, Immunity 29:249-260 (2008), Schlomchik, Immunity 28:18-28 (2008)). In certain embodiments ofimmunogen design of the instant invention, soluble IFN-$\alpha$ is encapsulated into liposomes conjugated to MPER peptides such as MPER656 or MPER656-L669S peptides. IFN-$\alpha$ has been reported to modulate and relax the selectivity for autoreactive B cells by lowering the BCR activation threshold (Uccellini et al, J. Immunol. 181:5875-5884 (2008)). The design of the immunogens results from the observation that lipid reactivity of gp41MPER antibodies is required for both binding to membrane bound MPER epitopes and in the neutralization of HIV-1.

The B cell subsets that the liposomes can target include any B cell subset capable of making polyreactive antibodies that react with both lipids and the gp41 epitopes of the MPER. These B cell subsets include, but are not limited to, the marginal zone IgM+ CD27+ B cell subset (Weill et al, Annu. Rev. Immunol. 27:267-85 (2009), Li et al, J. Exp. Med 195: 181-188 (2002)), the transitional populations of human B cells (Sims et al, Blood 105:4390-4398 (2005)), and the human equivalent of the B cells that express the human equivalent of the mouse Immunoglobulin (Ig) light chain lambda X (Li et al, Proc. Natl. Acad. Sci. 103:11264-11269 (2006), Witsch et al, J. Exp. Med. 203:1761-1772 (2006)). All of these B cell subsets have the capacity to make multireactive antibodies and, therefore, to make antibodies that have the characteristic of reacting with both lipids and HIV-1 gp41. That the liposomes have the characteristic of having both lipids and gp41 in them, should result in the selective targeting of these immunogens to the B cells of interest. Because these liposomes can be used to transiently break tolerance of B cells or to target rare B cell subsets, it can be seen that other HIV-1 envelope immunogens, such as deglycosylated envelope preparations, such as described below, can be formulated in the liposomes containing TLR 4 agonists, TLR 7/8 agonists and IFN$\alpha$.

The deglycosylated JRFL gp 140 Env protein and the CD4-binding site mutant gp140 (JRFL APA) have been described in a previous application (see, for example, WO 2008/033500). Deglycosylated env and Env mutated to not bind CD4 so as not to be immunosuppressive can be anchored in the liposomes by incorporating a transmembrane domain and, after solubilizing in detergent, can be reconstituted into synthetic liposomes. Alternatively, His-tagged (c-terminus end) versions of the Env gp140 can be anchored into liposomes as described for an intermediate form of HIV-1 gp41 (gp41-inter).

Given that many B cell subsets capable of making polyreactive antibodies also bind mammalian DNA, addition of DNA to liposomes can be used to target the immunogens to the responsive B cells.

The liposome-containing formulations of the invention can be administered, for example, by intramuscular, intravenous, intraperitoneal or subcutaneous injection. Additionally, the formulations can be administered via the intranasal route, or intrarectally or vaginally as a suppository-like vehicle. Generally, the liposomes are suspended in an aqueous liquid such as normal saline or phosphate buffered saline pH 7.0. Optimum dosing regimens can be readily determined by one skilled in the art.

Certain aspects of the invention can be described in greater detail in the non-limiting Examples that follows. See also Published PCT Application Nos. WO 2006/110831 and WO 2008/127651, U.S. Published Application Nos. 2008/0031890 and 2008/0057075, U.S. Provisional Application No. 60/960,413 and U.S. application Ser. No. 11/918,219.).

Example 1

Experimental Details

Subjects

Trinidad Seroconverter Cohort was described preciously (Blattner et al, J. Infect. Dis. 189:1793-1801 (2004)).

Briefly, patients from a sexually transmitted disease (STD) clinic were monitored for HIV infection and enrolled upon seroconvertion. Infections occurred through heterosexual contact and subtype B viruses accounted for all the infections. The patient of interest in this study, SC42, was naïve for antiviral therapy until 5 yr into infection.

Molecular Cloning of Full-Length Envelopes

Cloning strategy of full-length gp160 has been described previously (Wei et al, Nature 422:307-312 (2003), Li et al, J. Virol. 79:10108-10125 (2005)). Briefly, viral RNA was extracted from patient plasma samples using QIAmp Viral RNA Mini Kit (Qiagen, Valencia, Calif.) and subsequently reverse-transcribed into cDNA using SuperScript II ((Invitrogen Corp., Carlsbad, Calif.) and random hexamer primers. Full length envelope sequences were generated by nested PCR with the following primers: 1st round primers 5'OUT 5'-TAGAGCCCTGGAAGCATCCAGGAAG-3' (SEQ ID NO: 33), nt 5852-5876 and 3' OUT 5'-TTGCTACTTGT-GATTGCTCCATG T-3' (SEQ ID NO: 34), nt 8912-8935); and 2nd round primers 5'Intopo 5'-CACCTAGGCATCTC-CTATGGCAGGAAGAAG-3' (SEQ ID NO: 35), nt 5957-5982 and 3'IN 5'-GTCTCGAGATACTGCTCCCACCC-3' (SEQ ID NO: 36), nt 8881-8903). The PCR products were purified and then directly ligated into the directional cloning vector pcDNA 3.1DN5-His-TOPO (Invitrogen) following the manufacturer's directions. This pcDNA 3.1DN5-His-TOPO vector contains a cytomegalovirus promoter that allows the expression of envelope proteins for subsequent pseudovirus production.

Mutagenesis for Introduction of Single Mutation

A QuikChange XL Site-directed Mutagenesis Kit (Invitrogen Corp) was used to introduce S669L mutation into HS-MPER to generate HS-MPER/S669L, and K665N mutation into HS-MPER to generate HS-MPER/K665N following the manufactures instructions. The primers for introducing S669L mutation into HS-MPER were: fN-MPER_S669L (5'-GGATAAGTGGGCAAGTTTGTG-GAATTGGTTTGAC-3' (SEQ ID NO: 37)) and r7534.5_S669L (5'-GTCAAACCAATTCCACAAACTT-GCCCACTTATCC-3' (SEQ ID NO: 38)); the primers for introducing K665N into HS-MPER were: fHS-MPER_K665N (5'-gaattattagaattggataaCtgggcaagttcgtgg-3' (SEQ ID NO: 39)) and r7534.5_K665N (5'-CCACGAACT-TGCCCAGTTATCCAATTCTAATAATTC-3' (SEQ ID NO: 40)).

Production and Titration of Env-Pseudoviruses

Production and titration of the env-pseudoviruses was conducted following procedures modified from methods previously described (Li et al, J. Virol. 79:10108-10125 (2005)) with minor modifications. Full-length env clones in pcDNA3.1DN5-His-TOPO vector were co-transfected into 293T cells with an env-deficient HIV-1 backbone (pSG3Aenv) using FuGENE® HD transfection reagent (Roche Applied Science, Basel, Switzerland). Tissue culture fluid was harvested after 24-36 h of incubation and fresh fetal bovine serum was added to the virus stock to make a final concentration of 20%.

The 50% tissue culture infectious dose (TCID50) of each virus preparation was determined on JC53-BL cells as previously described (Li et al, J. Virol. 79:10108-10125 (2005)). Briefly, serial diluted virus stocks were used to infect JC53-BL cells on 96-well-flat-bottom-plates for 48 h. The cells were then lysed with and the relative luminescence units (RLU) determined by BriteLite™ assay system (PerkinElmer, Inc., Waltham, Mass.). Wells with luciferase luminescence 2.5-fold over that of the cells only control were considered positive for virus infection. TCID50 was calculated using the Reed-Muench formula.

Neutralization Assay

Neutralization assays for the pseudoviruses were performed on JC53-BL cells on 96-well-flat-bottom-plates as previously described (Li et al, J. Virol. 79:10108-10125 (2005)). Briefly, serially diluted serum samples or purified Abs were incubated with testing viruses, followed by addition of JC53-BL cells. The relative luminescence unit (RLU) of each well was measured with BriteLite™ assay system and the IC50 was determined as the highest dilution of serum (in cases of serum samples) or the lowest concentration of Ab (in cases of purified Abs) that was able to inhibit virus infection by 50% compared to the virus control.

Peptide Absorption Neutralization Assay

Peptide absorption neutralization assay was modified from neutralization assay. Serially diluted serum samples or purified Abs were pre-incubated with properly diluted peptide for 1 h before addition of virus, followed by regular neutralization assays.

Surface Plasmon Resonance (SPR) Assays

SPR binding assays were performed on a BIAcore 3000 (BIAcore Inc, Piscattaway, N.J.) maintained at 20° C. as previously described (Alam et al, J. Immunol. 178:4424-4435 (2007)). Biotinylated versions of SP62 peptides-gp4 652-671 (QQEKNEQELLELDKWASLWN (SEQ ID NO: 41)) and SP62-L669S (gp41 652-671) (QQEKNEQEL-LELDKWASSWN (SEQ ID NO: 55)), and control peptides with scrambled sequences (2F5656-670 Scrambled and 2F5656-670/L669S Scrambled), were individually anchored on a BIAcore SA sensor chip as described (Alam et al, J. Immunol. 178:4424-4435 (2007), Alam et al, AIDS Res. Hum. Retroviruses 20:836-845 (2004)). Each peptide was injected until 100 to 150 response unit (RU) of binding to streptavidin was observed. Specific binding responses of mAb binding were obtained following subtraction of non-specific binding on the scrambled 2F5 peptide surface. Rate constants were measured using the bivalent analyte model (to account for the avidity of bivalent Ig molecules) and global curve fitting to binding curves obtained from 2F5 titrations, which ranged from 0.01 to 119 nM for mAb 2F5. mAb 2F5 were injected at 30 uL/min for 2-6 min and Glycine-HCl pH 2.0 and surfactant P20 (0.01%) were used as the regeneration buffer.

SPR assay with liposome-anchored peptides were done in a similar fashion as described above. The peptides used are SP62 (gp41 652-671)-GTH1 (QQEKNEQELLELDK-WASLWNYKRWIILGLNKIVRMYS-biotin (SEQ ID NO: 42), containing the consensus 2F5 epitope) and SP62-L669S (gp41 652-671)-GTH1 (QQEKNEQELLELDKWASS-WNYKRWIILGLNKIVRMYS-biotin (SEQ ID NO: 43), containing the 2F5 epitope with the L669S substitution).

Fitness Assay

The dual infection fitness assay was performed as previously described (Lu et al, J. Virol. 78:4628-4637 (2004)) with minor modifications. HIV-1 infectious chimeric viruses containing TND-669S or TND-669L env and a marker sequence (either Salmonella enterica serovar Typhimurium histidinol dehydrogenase [hisD] gene or the human placental heat-stable alkaline phosphatase [PLAP] gene) were generated by cotranfecting env PCR product and NL4-3 background vector with a reporter gene. In a dual infection fitness assay, two chimeric viruses with specific input ratio (as determined by real-time PCR of the reporter genes) were used to co-infect PBMC (MOI=0.001). Relative production of the viruses with the two Env species in the culture were measured by the corresponding marker (hisD or PLAP) using real-time RT-PCR. Production of an individual virus in a dual infection was determined by calculating the percentage of the individual virus in the total virus population at specific time points (Day 4, 7, and 10). The relative fitness value (1+S) of the individual virus was determined by following equation as previously described (Wu et al, J. Virol. 80:2380-2389 (2006)):

$$(1+S=\exp(d)=\exp\{\ln[(TM(t2)\times TL(t1))/(TL(t2)\times TM(t1))]/\Delta t\}$$

1+S=exp, where S is the selection coefficient; Mt, M0, Lt, and L0 are the proportion of more fit variant or less fit variant at time point t and the initial proportion (0) in the inoculum respectively.

Results

Identification of TND-669S Envelope

Figure 1:
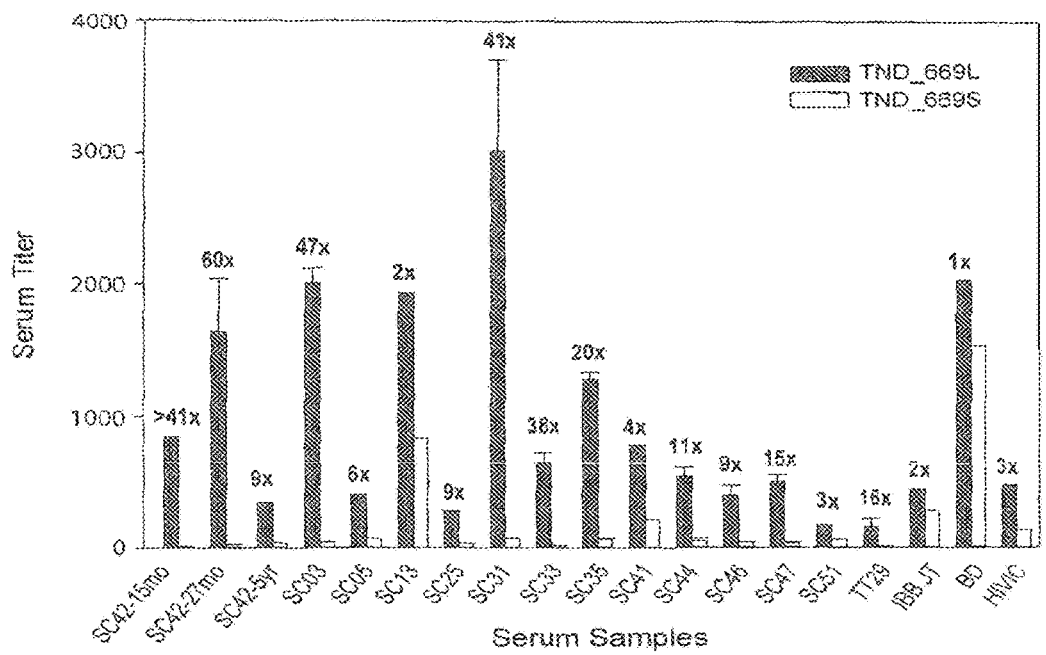
FIG. 1. Neutralizing sensitivity of TND-669S and TND-669L Env-pseudoviruses by autologous and heterologous sera/Ab. SC42-15 mo, SC42-27 mo, and SC42-5 yr are autologous sera from 15 mo, 27 mo, and 65 mo p.i.; SCO3-TT29 are heterologous sera from Trinidad cohort; IBBJT, BD are HIV+ patient sera used as positive controls; HIVIG is purified pooled IgG from HIV+ patient sera. Due to sample availability limitation, not all samples were tested more than once. For those samples that were tested more than once, the bars represents the average titer, and the error bars represent standard errors.

Multiple longitudinal Env clones were obtained from plasma samples of SC42, NL4-3 Env-pseudotyped viruses were made from the Env clones, and neutralizing sensitivity of selected Env clones against autologous as well as heterologous sera was tested. An envelope strain that was highly sensitive to neutralization by autologous sera was identified. TND-669S, an envelope clone obtained from a chronically infected HIV+ subject showed unexpectedly high sensitivity to neutralization by both autologous and heterologous sera. TND-669S was neutralized by contemporaneous and 27 month (post enrollment) autologous sera with titers of 845 and 1,353 respectively, while TND-669L, another isolate the neutralization sensitivity of which was typical of envelope clones obtained from the same time point (15 month post enrollment) and was retrospectively selected for comparison based on its envelope sequence, was not sensitive to contemporaneous autologous serum neutralization and was neutralized by 27 months post enrollment autologous serum with a titer of only 26 (FIG. 1). TND-669S and TND-669L Env-pseudoviruses were then tested against a panel heterologous patient sera as well as several HIV+ sera/Ab used as positive controls. TND-669S Env-pseudovirus was shown to be up to 47-fold more sensitive to neutralization by heterologous sera within Trinidad cohort. Among the 14 patient sera tested, 7 neutralized the TND-669S pseudovirus more than 10-fold more efficiently than the TND-669L pseudovirus (FIG. 1).

Identification of the L669S Mutation

Figure 2:
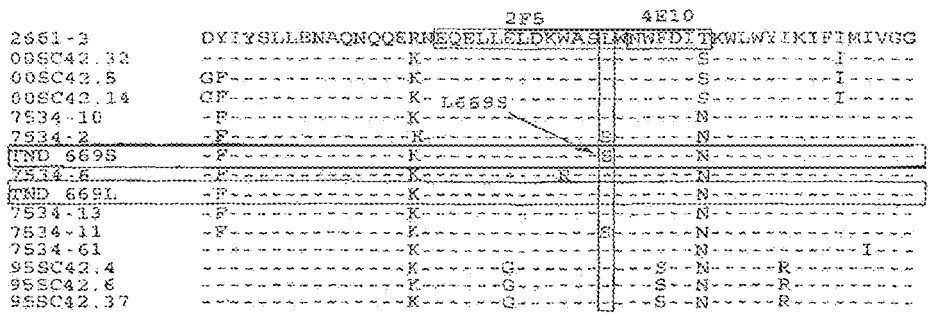
FIG. 2. Partial alignment of selected SC42 Env sequences (SEQ ID NOS 46-48, 48-50, 50-51, 49, 49-50, 52-53, 53 and 53, respectively, in order of appearance). TND-669S, TND-669L and 7534-xx (wherein "xx" is as shown in FIG. 2) are sequences from 15 mo p.i. plasma; Other sequence shown are selected sequences from week 0 (2661-x), week 1 (00SC42-xx) and from 60 mo (95SC42-xx) (wherein "x" and "xx" are as shown in FIG. 2) p.i. plasma. Consensus epitope sequences for 2F5 and 4E10 are highlighted in blue and green boxes, respectively.

The protein and DNA sequences for TND-669S and TND 669L gp160 were examined for genetic variations responsible for the increased neutralizing sensitivity of TND-669S envelope. There are 6 nucleotide differences between the two env DNA sequences. However, 5 of those are synonymous mutations, resulting in a single amino acid difference between TND-669S and TND-669L Env. The single amino acid difference is located at position 669, near the C-terminus of the 2F5 epitope and 2 aa upstream of the 4E10 epitope in the MPER (FIG. 2). TND-669L contains the 2F5 consensus sequence while TND-669S contains a L669S mutation. 3 out of 10 clones obtained from the 15 month post enrollment plasma of patient SC42 contain this mutation, while this mutation was not found in either 1 wk post enrollment plasma or 5 yr post enrollment plasma. Interestingly, only 1 out of around 1000 full-length Env sequences in LANL database contains this L669S mutation.

Sensitivity of the L669s Mutant to Monoclonal Antibodies

Figures 3A, 3B:
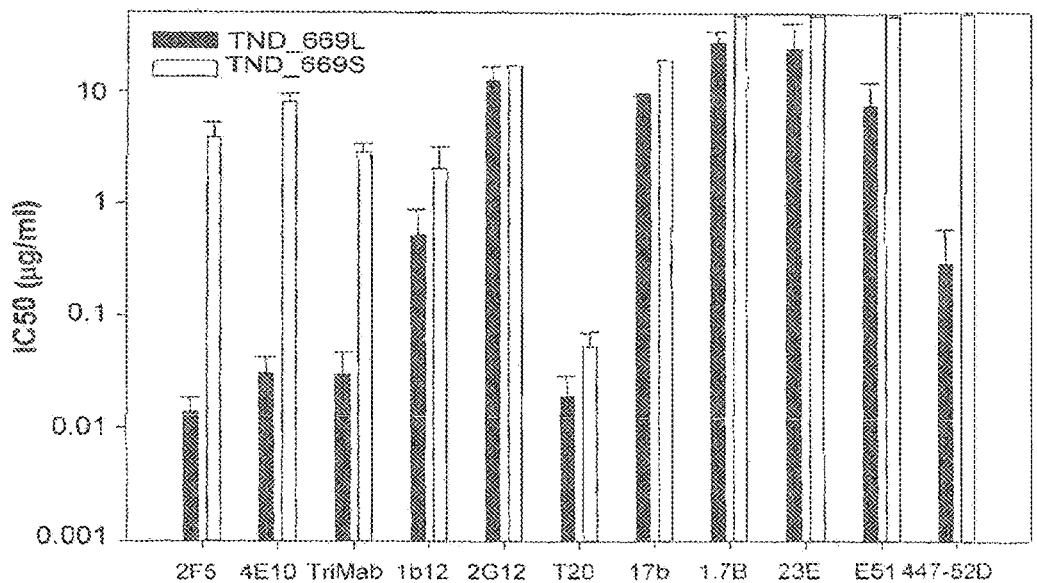
FIGS. 3A and 3B. Neutralization of TND-669S and TND-669L Env-pseudoviruses by various monoclonal antibodies and the entry inhibitor T20. The mean IC50 of each reagent against the two strains are shown in FIG. 3A, with error bars showing the standard errors. The IC50 values and the fold differences of each neutralizing antibodies in its potency against TND-669S and TND-669L are shown in FIG. 3B. Each IC50 was obtained from at least two independent tests. Data for 2F5, 4E10, TriMab, 1b12, and 2G12 also include one set of data from a test performed by Dr. Montefiori's laboratory (Duke University). The fold difference between the IC50 of each mAb against TND-669S and TND-669L (TND-669:tND-669L) are listed in the last column of the table, and the ones with significant increase in sensitivity of TND-669S are highlighted in yellow (and marked with a "√").

Based on the location of the L669S mutation, sensitivity of the TND-669S and TND-669L to 2F5 and 4E10 mAbs was tested. Not surprisingly, TND-669S was highly sensitive to 2F5 mAb while TND-669L was only moderately sensitive (FIG. 3). Interestingly, TND-669S is also highly sensitive to neutralization by 4E10 mAb compared to TND-669L. As shown in FIG. 3, the IC50 of 2F5 and 4E10 mAbs against TND-669S Env-pseudovirus were 279- and 275-fold lower than that against TND-669L Env-pseudovirus, respectively. The mean IC50 of TND-669S and TND-669L were 0.014 (±0.0056) and 3.92 (±~1.52) respectively for 2F5, and 0.031 (±0.012) and 8.49 (±1.29) µg/ml, respectively, for 4E10.

Sensitivity of TND-669S and TND-669L pseudoviruses to several other neutralizing agents, including the glycan dependent mAb 52D and the entry inhibitor T20 was also tested (FIG. 3). No significant difference in sensitivity to 2G12 and T20 and only a slight increase in sensitivity to 17b and 1b12 (~2 and 4-fold, respectively) was observed for the TND-669S pseudovirus, indicating that global changes in envelope, if any, cannot account for the dramatically enhanced neutralizing sensitivity observed for the TND-669S envelope. Differences in sensitivity of the two strains against 1.7B, 23E, and E51 could not be quantified because the TND-669L is not sensitive enough to neutralization by these antibodies. Interestingly, the TND-669L envelope was also not sensitive to 447-52D neutralization while the TND-669L envelope was neutralized with an 1050 of 0.31 µg/ml, indicating an enhancement of >161-fold in 447-52D sensitivity associated with the L669S mutation.

Single L669S Mutation Accounts for the Phenotypic Change

To confirm that the L669S mutation alone is responsible for the phenotypic change, a S669L mutation was introduced into the TND-669S envelope by site-directed mutagenesis. The resulting TND-669S/S669L showed only moderate sensitivity to 2F5 comparable to that of TND-669L, confirming the sole contribution of the L669S mutation in the TND 669S to the increased sensitivity to neutralization. Next, the role of the virus backbone in the phenotypic change associated with the L669S mutation was investigated. A L669S mutation was introduced into the envelope of another primary isolate, QZ4734. The L669S mutation rendered the QZ4734 Env-pseudovirus more than two logarithmic magnitudes more sensitive to neutralization by the 2F5 mAb (FIG. 15). Furthermore, the other two clones that share the L669S mutation showed similar magnitude of increase in sensitivity against 2F5 (FIG. 16). These findings suggest that the L669S can increase the sensitivity of HIV-1 envelope to neutralization by MPER antibodies regardless of the virus background.

Neutralizing of TND-669S Envelope is Mediated by 2F5 Binding to its Conventional Epitope Characterization of a 2F5-resistant Env variant has shown that a K665N mutation in the DKW core region abrogates 2F5 binding and results in 2F5 resistance (Purtscher et al, Aids 10:587-593 (1996)). This suggests that the DKW in the core region of the 2F5 epitope EQELLELDKWASLWN (SEQ ID NO: 44) is essential for 2F5 binding. To test whether the potent neutralization of the TND-669S envelope by 2F5 is also mediated though binding of the 2F5 mAb to the core amino acids of the conventional 2F5 epitope, a TND-669S/K665N mutant was made and its sensitivity to 2F5 and 4E10 mAbs was tested. Introduction of the K665N mutation into the TND 669S envelope resulted in a fully 2F5-resistant phenotype while the sensitivity of the envelope against 4E10 was not affected.

Ability of the 2F5 Peptides to Absorb the Neutralizing Activity of the 2F5 mAb

Figures 4A, 4B:
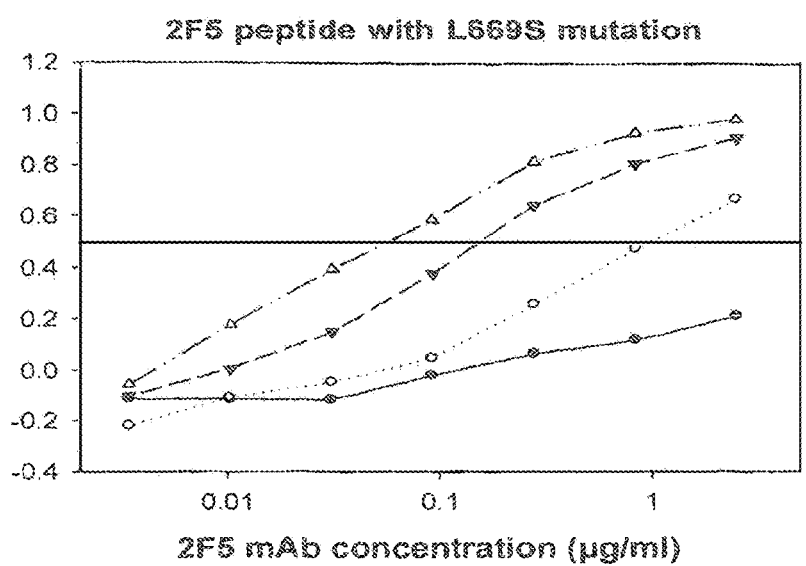
FIGS. 4A and 4B. Peptide absorption neutralization assays. Neutralization of the TND-669S Env-pseudovirus by mAb 2F5 was tested with different doses of 2F5 peptides. Inhibition of 2F5 mAb neutralization by the mutant peptide (containing 2F5 epitope with the L669S mutation, 2F5656-670/L669S) is shown FIG. 4A. The inhibition curves generated by the peptide containing the consensus peptide (consensus peptide) are similar. The IC50 data are summarized in the table in FIG. 4 B. Similar tests were also performed on the TND-669L viruses. A similar trend was observed, however, due to the low sensitivity of TND-669L to 2F5 mAb, data generated using the TND-669L pseudovirus were not quantitative.
Figure 6A:
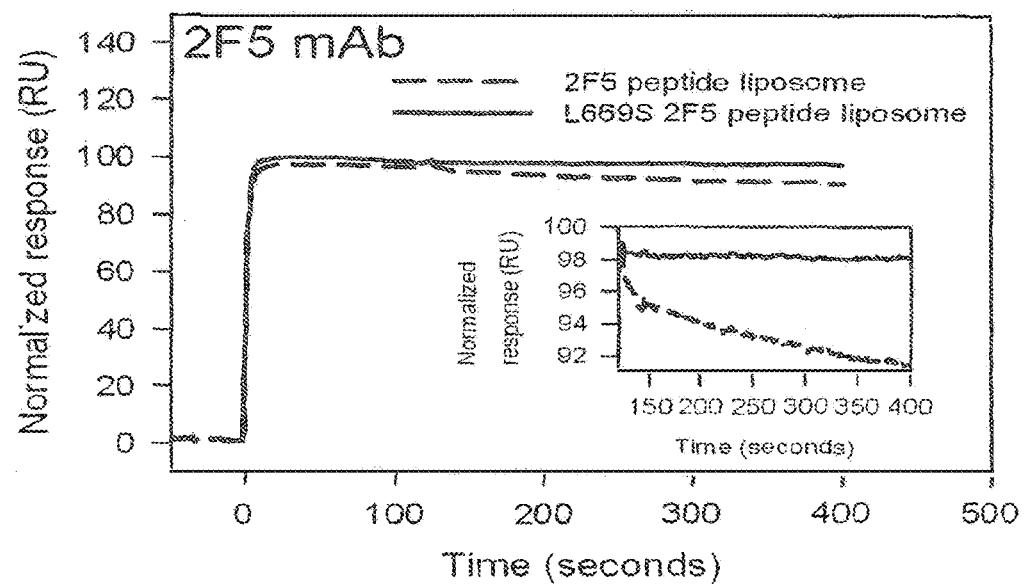
FIGS. 6A and 6B. Binding of 2F5 mAb to peptide-liposome conjugates.
Figure 6B:

To investigate the possible mechanisms involved in the ability of the L669S substitution to increase the MPER neutralizing sensitivity, peptides containing either the consensus 2F5 epitope (2F5656-670) or the 2F5 epitope with the L669S substitution (2F5656-670/L669S) were synthesized and subsequently tested for their ability to absorb 2F5 mAb neutralizing activity. The 2F5 mAb was pre-absorbed with either the F5con or the F5mut peptide prior to the neutralization assay. Surprisingly, F5mut did not inhibit 2F5 mAb neutralization more potently than F5con. As show in FIGS. 6A and 6B, both peptides inhibited 2F5 neutralization of the TND-669S Env pseudovirus in a dose-dependent manner. However, F5con is more efficient at inhibiting 2F5 neutralization, manifested by comparable levels of inhibition achieved by 3 µM of F5mut (reduced the IC50 of the 2F5 mAb to 0.951 µg/ml) and 0.3 µM of F5con (reduced the IC50 of the 2F5 mAb to 0.911 µg/1) (FIG. 4B).

Figure 5A:
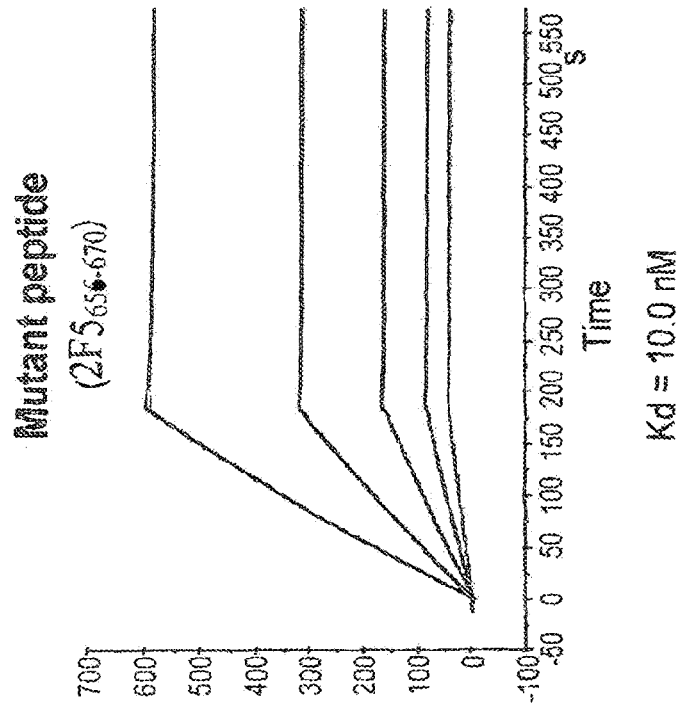
FIGS. 5A and 5B. BIAcore SPR assay for binding avidity of F5mut (FIG. 5A) and F5con (FIG. 5B) peptides to mAb 2F5.
Figure 5B:
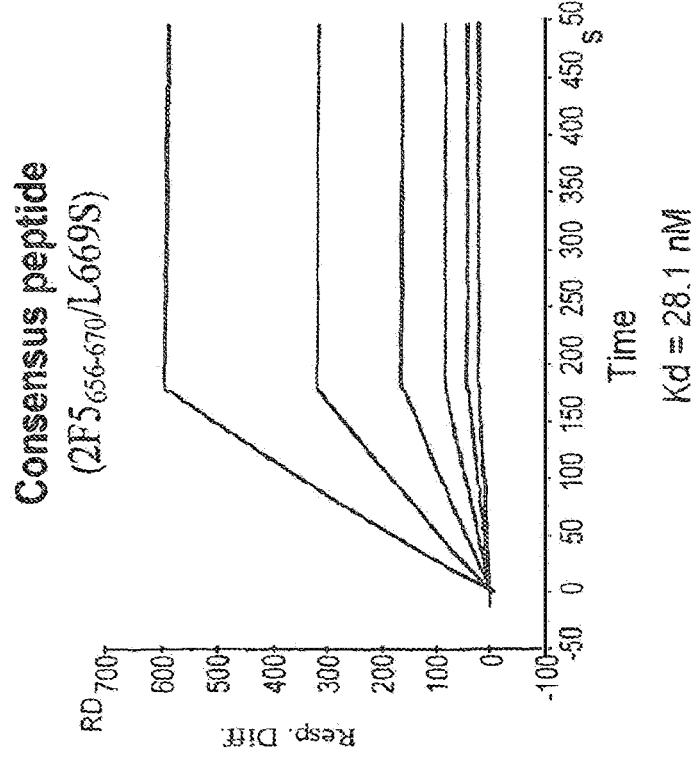

L669S Mutation Did not Increase the Binding Avidity of the 2F5 mAb for its Epitope To investigate the possibility that the L669S mutation enhances the avidity of the 2F5 epitope to the 2F5 mAb, peptides containing either the consensus 2F5 epitope (2F5656-670) or the 2F5 epitope with the L669S mutation (2F5656-6701L669S), along with the scrambled version for each peptide, were tested in a BIAcore SPR (surface plasmon resonance) assay for 2F5-binding thermodynamics. The equilibrium dissociation constants (KD) for the F5con and F5mut peptides were 11.0 and 28.1 nM, respectively (FIG. 5), indicating that F5con binds to 2F5 with a slightly higher avidity than that of F5mut, although this 2.7-fold difference is not significantly different. Binding ELISA data also confirmed that there was no significant difference between the binding of the two peptides by 2F5 mAb (FIG. 5). This suggests that other factors may be involved in the differential sensitivity of the MPER sequences such as a conformational change in the MPER that alters the exposure of this region to neutralizing antibodies.

Binding of the Peptides to 2F5 mAb in Lipid Environment

In HIV-1 virus, MPER is in close proximity to the envelope lipid bilayer. Direct binding SPR assay has shown that 2F5 mAb binds to F5con and F5con peptides with comparable avidity. To further examine the possible influence of the L669S substitution on binding of the 2F5 mAb to its epitope in a lipid environment, a SPR binding assay was performed using peptides anchored to phospholipid-containing liposomes. As shown in FIG. 6, the peptide containing the L669S substitution bound 2F5 mAb with a response unit of 616.7 (background subtracted) at 10 seconds after the injection was stopped, while the consensus 2F5 epitope bound 2F5 with a response unit of 494.6, indicating that in a lipid environment, a 2F5 peptide with the L669S substitution does bind stronger to 2F5 mAb than the consensus 2F5 mAb.

Fitness of TND-669S Virus is Greatly Impaired

Figure 7:
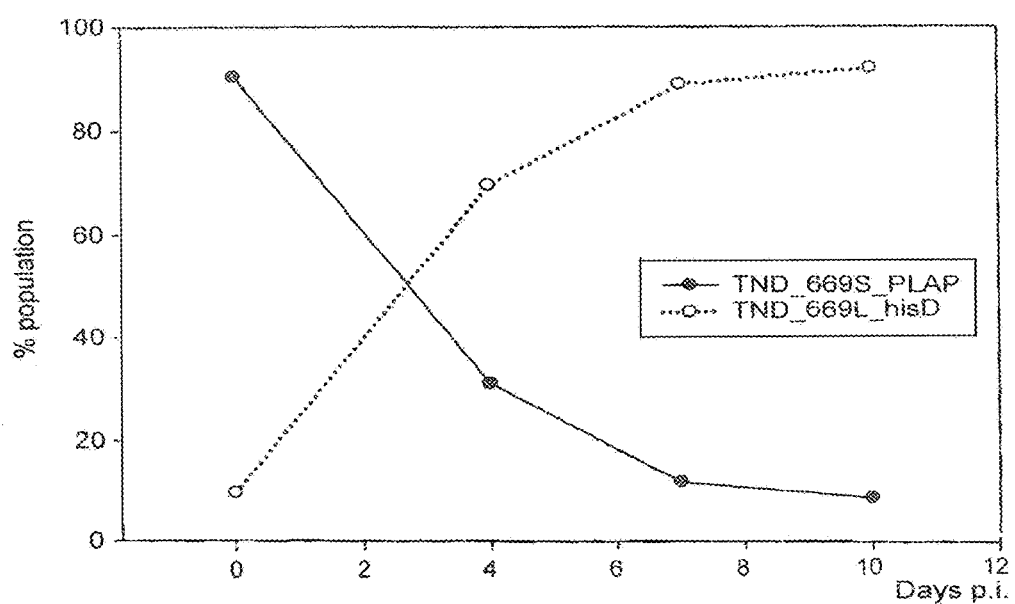
FIG. 7. Dual infection fitness assay in PBMC. Shown is a test with input ratio of 9:1 (TND-669S:TND-669L). The relative fitness value 1+S=1.86. (1+S=exp(d)=exp{ ln [(TM(t2)×TL(t1))/(TL(t2)×TM(t1))]/Δt}. Tests of 3 individual tests with different virus input ratios all conferred a 1+S value of 1.80~1.90.

To determine if the alteration in MPER structure resulted in a fitness defect, the relative fitness of TND 669S and TND-669L viruses was examined by a dual infection competition assay in peripheral blood lymphocytes, using replication competent recombinant viruses containing the NL4-3 backbone and the TND-669S and TND-669L envelope sequences, respectively. With an input ratio of 9:1 (TND-669S:TND-669L), the TND-669S virus was outgrown by the TND-669L virus at 4 days post infection (FIG. 7), suggesting a significant loss of fitness associated with the L669S mutation in the TND 669S virus. The calculated relative fitness (1+S) is 1.86. To further quantify the fitness differences, a ratio of 1:4 (TND-669S:TND-669L) was also examined and confirmed the lowered fitness of the TND 669S virus.

In summary, a mutation in the HIV-1 envelope, L669S, has been identified that significantly increases the neutralization sensitivity of the envelope to both 2F5 and 4E10 mAb neutralization. The mean IC50 of the TND-669S and TND-669L Env-pseudoviruses against mAbs 2F5 and 4E10 are 0.014 and 0.031 µg/ml, respectively. In a study by Binley et al (J. Virol. 78:13232-13252 (2004)), where a panel of 93 HIV-1 strains were examined for neutralizing sensitivity to various mAbs, most isolates were neutralized by 2F5 and 4E10 with IC50 of 1-10 µg/ml, while only 9 strains were neutralized at IC50<1 µg/ml by 2F5 mAb, and 9 neutralized by 4E10 mAb at IC50 of <1.0 µg/ml. The IC50 of TND-669S against 2F5 and 4E10 mAbs was even lower than the most 2F5/4E10 mAb sensitive strain (BUSxxxMNc), which was neutralized by 2F5 and 4E10 mAb with IC50 values of 0.05 and 0.17 µg/ml, respectively. In comparison, the L669S mutation renders the envelope 4- and 5-fold more sensitive to 2F5 and 4E10 mAb neutralization, respectively, than the most sensitive virus previously reported.

A single amino acid mutation L669S is responsible for this specific phenotype, as supported by site directed mutagenesis of the L669S mutation into another primary isolate, QZ4734, which rendered the QZ4734/L669S Env-pseudovirus more than 2 logs more sensitive to 2F5 mAb neutralization. To further confirm this, the serine at position 669 of the TND-669S was also mutated back to leucine resulting in the loss of the ultra sensitivity observed in TND-669S envelope.

Both TND-669S and TND 669L envelopes were obtained through bulk PCR. Single genome amplification (SGA) was performed later but the envelope sequences were not identified indicating that the L669S mutation was not circulating in vivo. Additionally, the L669S mutation results in a significant loss of fitness indicating that even if present in natural infection, it would not have circulated long because of its poor fitness level.

In an elegant alkaline-scanning mutagenesis study by Zwick et al, J. Virol. 79:1252-1261 (2005), 13 out of 21 MPER Ala mutants were more sensitive to 2F5 or 4E10 mAb, or both, than the parental MPER. An L669A mutation in HIV-1 JR2 was 50- and 45-fold more sensitive to neutralization by 2F5 and 4E10 mAbs, respectively, and was among the most sensitivity-enhancing mutations. These findings, together with present data, suggest that there may be some common mechanisms shared by the 2F5 and 4E10 epitopes, such as the structure or the accessibility of the MPER, that greatly affects Env sensitivity to MPER neutralizing antibodies.

The mechanisms of the L669S substitution-associated increase in HIV-1 envelope sensitivity to MPER neutralization warrants in depth study because it sheds light on the neutralizing mechanisms of 2F5 and 4E10, and provides important information regarding immunogen design to elicit these types of antibodies.

There are multiple ways through which this mutation may increase neutralizing sensitivity. First, the mutation could have caused dramatic changes in Env and affected the expression level of functional Env spikes on viral particles. Neutralizing assays with multiple other neutralizing agents showed that the increase in neutralizing sensitivity of the TND-669S envelope is not a global effect, making it unlikely that L669S mutation enhances neutralizing sensitivity through changes in Env expression levels. Secondly, this mutation could have changed the fusion kinetics of gp41, resulting in a slower fusion process. Env with reduced fusion kinetics have been shown to be more sensitive to 2F5 and 4E10 neutralization (Reeves et al, J. Virol. 79:4991-4999 (2005)). This is unlikely since the sensitivity of the TND-669S envelope to T20 was only 3-fold that of the TND-669L envelope, suggesting the fusion kinetics is not changed considerably by L669S mutation. Thirdly, it is possible that the L669S mutation itself renders higher avidity binding of the 2F5 mAb to the 2F5 epitope. This hypothesis, however, is not supported by the surface plasmon resonance (SPR) assay results for peptide binding to 2F5, where the 2F5 consensus peptide (containing the consensus 2F5 epitope sequence) bound with slightly higher avidity than did the 2F5 mutant peptide (containing the L669S mutation). Moreover, this hypothesis cannot explain the similar fold of increase in the sensitivity of the TND-669S envelope to both 2F5 and 4E10 mAbs. Fourthly, the L669S mutation could have caused dramatic conformational change of Env, resulting in a more "open" MPER structure, and thus allowing for easier access of antibodies targeting 2F5 and 4E10. This hypothesis can very well explain the similar magnitude of increase in sensitivity of the TND-669S envelope to both 2F5 and 4E10 mAbs. The 447-52D sensitivity changes associated with the L669S mutation (>161x) suggests that the conformational change may have caused changes in the V3 loop as well. Steric constraints for neutralizing antibodies targeting MPER have been suspected by many groups. Several studies have observed possible antagonism between 2F5 and 4E10 (Zwick et al, J. Virol. 79:1252-1261 (2005), Nelson et al, J. Virol. 81:4033-4043 (2007)), suggesting that space limitation may be a factor affecting 2F5 and 4E10 neutralization of HIV virus. Interestingly, when 2F5 epitope was inserted to MLV Env (Ou et al, J. Virol. 80:2539-2547 (2006)), the Env with 2F5 epitope in surface unit is more than 10 times more sensitive to 2F5 neutralization than the Env with 2F5 epitope in the transmembrane unit. In addition, grafting 2F5 epitope into V1, V2, V4 regions of HIV Env also was shown to increase the binding of gp140 to 2F5 (Joyce et al, J. Biol. Chem. 277:45811-45820 (2002), and grafting 2F5 and 4E10 epitopes to the MPER of HIV-2 has been shown to be associated with substantial increase in 2F5-/4E10-neutralization sensitivity (Decker et al., presented at the Keystone Symposium on HIV Vaccines, Keystone Resort, Keystone, Colo., 2006), presumably through improved epitope accessibility. These data reflected the influence of epitope accessibility on 2F5 sensitivity. The characteristic of TND-669S is in concordance with a likely more "open" MPER structure. The TND-669S isolate can be used to detect the presence of 2F5 and 4E10-like antibodies elicited by vaccination or natural infection (studies to date have failed to detect 2F5 or 4E10 in HIV-1 infected patients and vaccines). An ultra-sensitive isolate can provide crucial information as to whether or not 2F5/4E10 is generated at extremely low levels during natural infection or vaccination. Furthermore, the demonstration that a more exposed MPER, as TND-669S envelope appears to have, has significant applications for vaccine immunogen design.

Example 2

Description of some embodiments of gp41MPER Peptide-Liposome Conjugates

Figure 8:
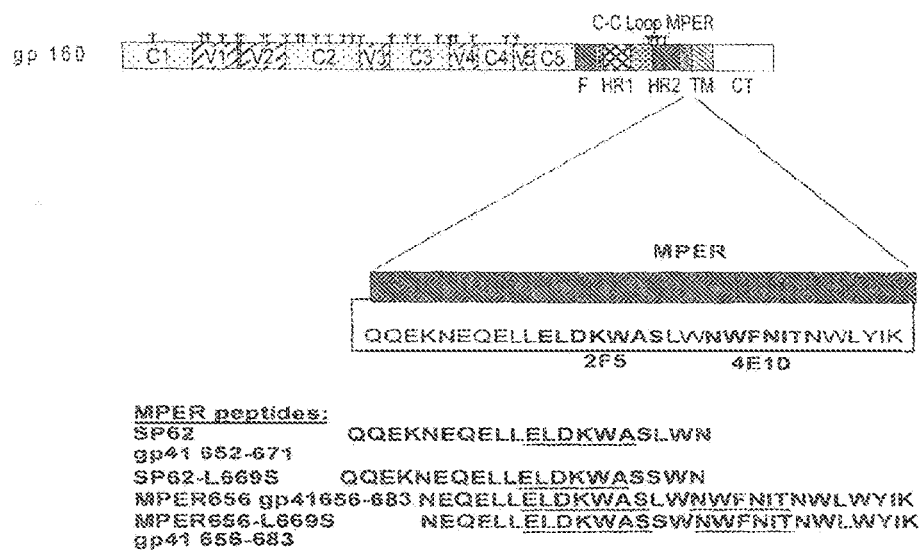
FIG. 8. HIV-1 gp41MPER peptides that include the epitopes of the two broadly neutralizing antibodies 2F5 and 4E10. Amino acid sequences of the gp41 MPER peptides that can be conjugated to synthetic liposomes are shown (SEQ ID NOS 54, 41, 55, 9 and 56, respectively, in order of appearance).

FIG. 8 shows the amino acid sequences of each of the HIV-1 gp41MPER peptides that can be conjugated to synthetic liposomes. While these sequences have been used, longer gp41 sequences encompassing the entirety of the Heptad Repeat 2 (HR2) region (aa 637-683), as well as longer sequences involving the HR2 region as well as the HR1 region could be used (aa 549-602). The SP62 peptide presents the 2F5 mAb epitope while the MPER656 peptide includes both 2F5 and 4E10 mAb gp41 epitopes. (See WO 2008/127651.) Two variants of the MPER peptide sequences include the SP62-L669S and the MPER656-L669S. The L669S mutation was identified in an HIV-1 Envelope clone (TND-669S), obtained from a chronically infected HIV-1+ subject, that was highly sensitive to neutralization by both autologous and heterologous sera (see Example 1). TND-669S is highly sensitive (with IC50 about 300-fold lower when compared to TND-669L) to neutralization by both 2F5 and 4E10 mAbs (Shen J. Virology 83: 3617-25 (2009)). The mutation resulted in more favorable mAb binding kinetics with significantly slower off-rates of the mAb 2F5-peptide liposome complex (SP62-L669S peptide-liposomes). Tryptophan (W) immersion depth analysis of SP62-liposomes suggested that the L669S substitution could alter the orientation of the core 2F5 and 4E10 epitopes and make them more accessible for B cell recognition. Thus, the use of L669S substitution in both forms of liposomes with SP62-L669S and MPER656-L669S peptides afford novel immunogens with favorably exposed core MPER neutralizing epitopes and the potential for the induction of neutralizing antibodies following immunization.

Description of gp41 MPER Peptide-Adjuvant Conjugates

Toll-like receptor ligands, shown in FIG. 9, were formulated in liposomal forms with gp41MPER peptide immunogens. The ligands referenced in FIG. 9 are examples only and other forms of TLR agonists (Takeda et al, Annu. Rev. Immunol., 21:335-376 (2003)) can be incorporated into similar liposomes as well.

The construction of Lipid A and R-848 containing MPER peptide liposomes utilized the method of co-solubilization of MPER peptide having a membrane anchoring amino acid sequence and synthetic lipids 1-Palmitoyl-2-Oleoyl-sn-Glycero-3-Phosphocholine (POPC), 1-Palmitoyl-2-Oleoyl-sn-Glycero-3-Phosphoethanolamine (POPE), 1,2-Dimyristoyl-sn-Glycero-3-Phosphate (DMPA) and Cholesterol at mole fractions 0.216, 45.00, 25.00, 20.00 and 1.33 respectively (Alam et al, J. Immunol. 178:4424-4435 (2007)). Appropriate amount of MPER peptide dissolved in chloroform-methanol mixture (7:3 v/v), Lipid A dissolved in Chloroform or R-848 dissolved in methanol, appropriate amounts of chloroform stocks of phospholipids were dried in a stream of nitrogen followed by overnight vacuum drying. Liposomes were made from the dried peptide-lipid film in phosphate buffered saline (pH 7.4) using extrusion technology.

Construction of oligo-CpG complexed MPER peptide liposomes used the cationic lipid 1-Palmitoyl-2-Oleoyl-sn-Glycero-3-ethylphospho choline (POEPC) instead of POPC. Conjugation of oCpG was done by mixing of cationic liposomes containing the peptide immunogen with appropriate amounts of oCpG stock solution (1 mg/ml) for the desired dose.

Surface Plasmon Resonance (SPR) assay for the binding of 2F5 mAb to its epitope in the peptide-liposome constructs revealed that incorporation or conjugation of TLR adjuvants does not affect binding of HIV neutralizing antibody 2F5. Strong binding of both mAbs 2F5 and 4E10 were observed.

Example 3

Figure 14A:
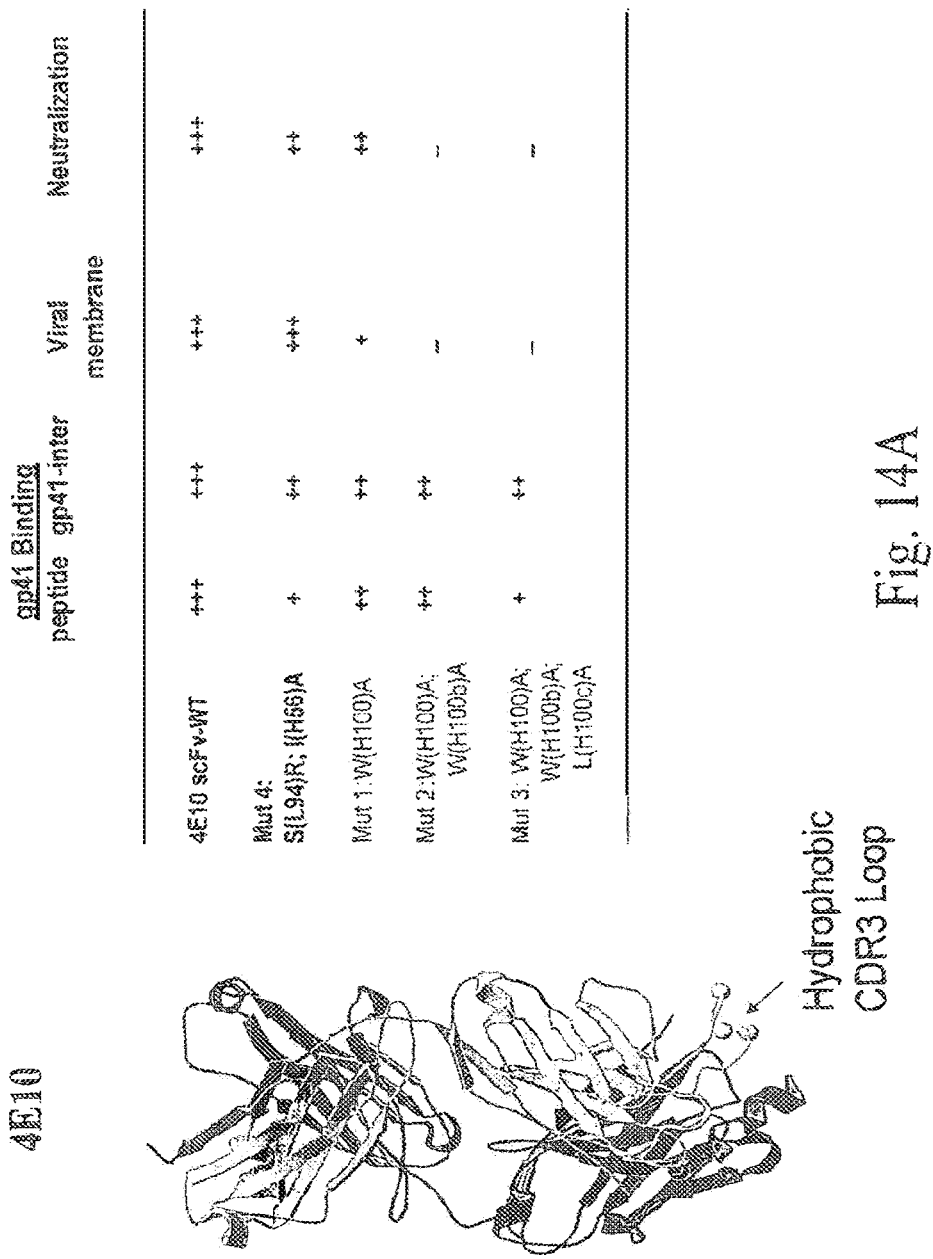
FIGS. 14A and 14B. Substitution of hydrophobic residues of 4E10 (FIG. 14A) and 2F5 (FIG. 14B) CDR H3 disrupt lipid binding and abrogate ability of both mAbs to neutralize HIV-1.
Figure 14B:
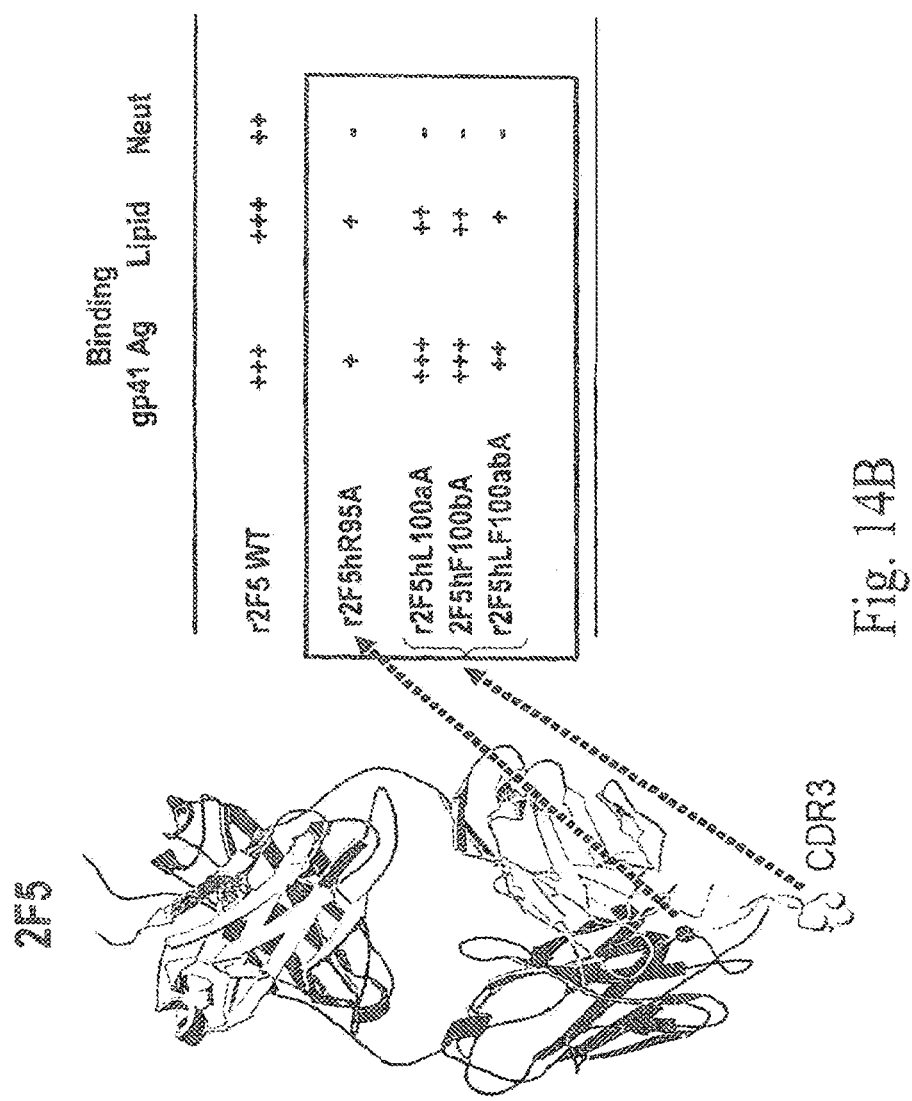

The long CDR H3 loops of MPER neutralizing mAbs 4E10 and 2F5 have a hydrophobic face, postulated to interact with virion membrane lipids (Ofek et al, J. Virol. 78:10724 (2004); Cardoso et al, Immunity 22:163-173 (2005)). CDRH3 mutants of 4E10 (scFv) and 2F5 (IgG) have been constructed (see FIG. 13) and it has been found that binding of neutralizing MPER mAbs occur sequentially and is initiated by binding of mAbs to viral membrane lipids prior to binding to prefusion intermediate state of gp41. 4E10 scFv bound strongly to both nominal epitope peptide and a trimeric gp41 fusion intermediate protein, but bound weakly to both HIV-1 and SIV virions and thus indicating that 4E10 bound to viral membrane lipids and not to the prefusion state of gp41. While alanine substitutions at positions on the hydrophobic face of the CDR H3 loops of 4E10 (W100a/W100b/L100cA) showed similar binding to gp41 epitopes, the same substitutions disrupted the ability of 4E10 to bind to HIV-1 viral membrane (FIG. 14). 4E10 CDR H3 mutants that bound to gp41 intermediate protein but did not bind to HIV-1 viral membrane failed to neutralize HIV-1. Similarly, 2F5 CDR H3 mutants with disruptions in binding to HIV-1 virions but not to gp41 epitope peptide, failed to neutralize HIV-1 (FIG. 14). Blocking of HIV-1 neutralization activity of 4E10 by gp41 fusion intermediate protein further suggested that 4E10 did not bind to viral prefusion gp41. These results support the model that binding of neutralizing MPER mAbs occurs sequentially and is initiated by binding of mAbs to viral membrane lipids prior to binding to prefusion intermediate state of gp41. An important implication of this result is that the HIV-1 membrane constitutes an additional structural component for binding and neutralization by 4E10 and 2F5. Thus, a lipid component may be required for an immunogen to induce 4E10 and 2F5-like antibody responses.

Thus, this strategy has the potential to modulate B cell tolerance, target immunogens to responsive B cell subsets, and allow the induction of polyreactive B cells that bind to phospholipids and gp41MPER epitopes. When used in combination with TLR ligands, the delivery of IFN-α in liposomes has the potential to allow TLR-dependent activation of B cells from the autoreactive pool and with the desired specificity for gp41MPER epitopes.

Description of Constructs

Figure 11:
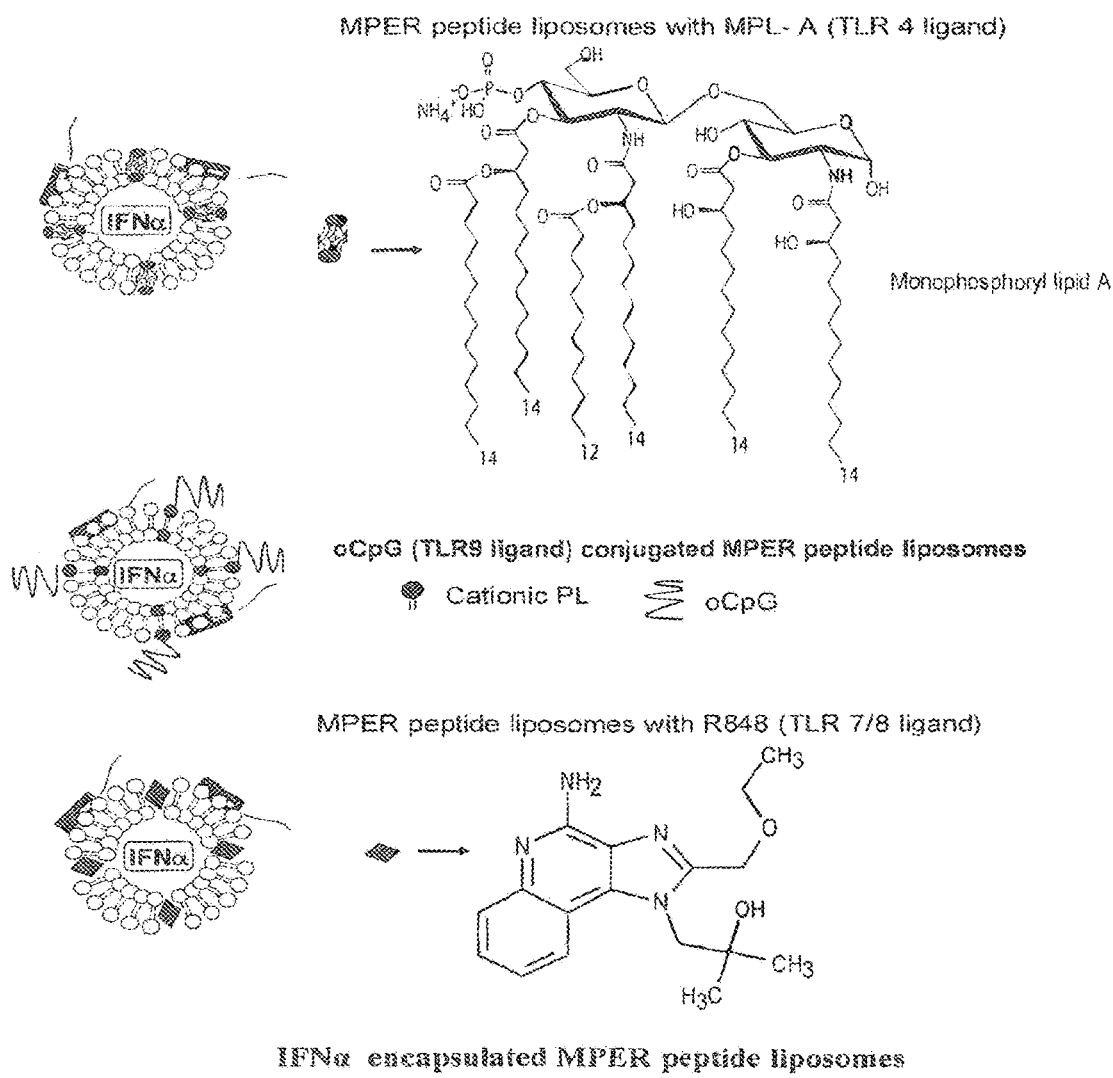
FIG. 11 IFNα encapsulated MPER peptide liposomes

The HIV-1 gp41MPER peptides (FIG. 8) can be conjugated to synthetic liposomes as outlined above and described previously (Alam et al, J. Immunol. 178:4424-4435 (2007)). Each of the sonicated MPER peptide-liposomes can be prepared and then mixed with soluble IFNα protein and then dried and rehydrated to encapsulate the cytokine. After brief vortexing, the rehydrated liposomes with encapsulated IFNα can be collected by ultracentrifugation for 30 min. In a first design, liposome is conjugated to either oCpG (TLR 9), MPL-A (TLR4) or R848 (TLR7/9) (FIG. 11). Each of these adjuvanted liposome constructs can be prepared with each of the listed MPER peptides shown in FIG. 8. A second design is shown in FIG. 12 and includes multiple TLR ligands, TLR 9+TLR 4 and TLR9+TLR 7/8 incorporated into the same liposomes. The design of these constructs can provide synergy in TLR triggering and potentially enhance the potency of the TLR ligands in activating polyreactive B cells.

Figure 10A:
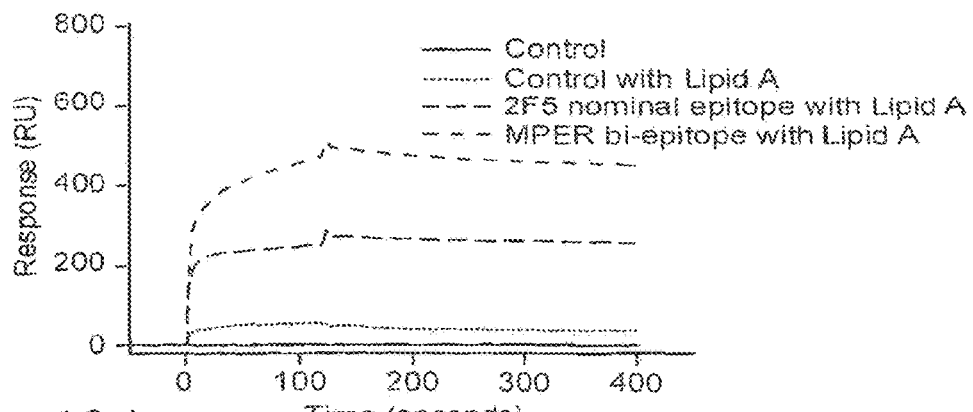
FIGS. 10A-10C. Interaction of 2F5 mAb with MPER peptide-liposomes conjugated to TLR adjuvants.
Figure 10B:
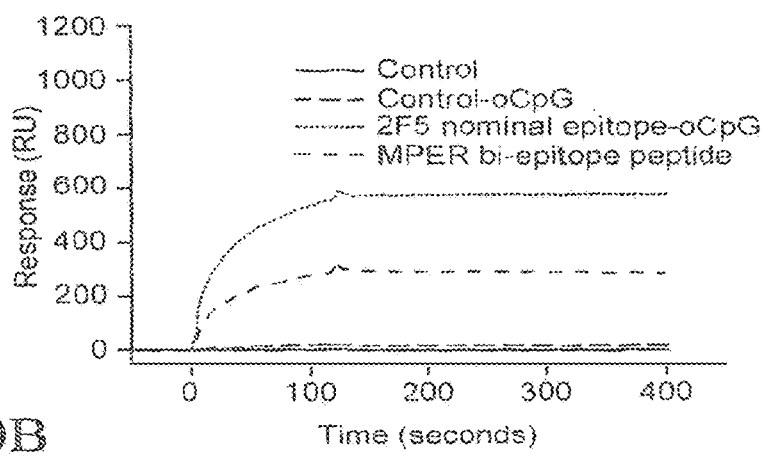
Figure 10C:
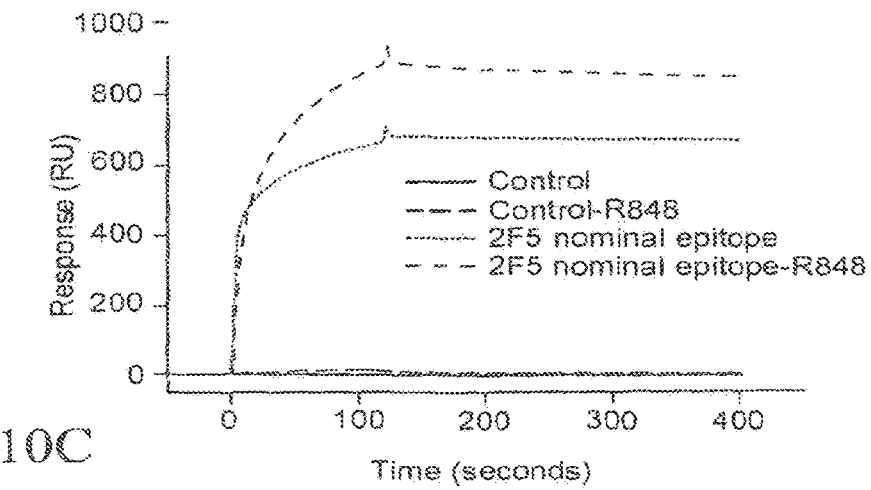

The assessment of the presentation of MPER epitopes on the adjuvanted liposome constructs can be done by SPR analysis of 2F5 and 4E10 mAb binding as described in FIG. 10.

Example 4

Experimental Details

Representative data from two immunized animals show the application of a prime/boost strategy for the induction of MPER specific antibody responses following repeated immunizations with MPER peptide liposomes (see FIG. 17). The animals were immunized at alternating and at regular interval first with SP62 liposomes (4×), and then with Env gp140 (2×) protein. The final two immunizations include the full length MPER-656 liposomes (see description of immunogens above). Binding responses in immunized sera were measured by SPR analyses of binding to MPER peptide with the shown sequence. Bleed samples from each immunized animals were collected at the indicated post-bleed time points. Epitope mapping of the immunized sera was done on the BIAcore A100 using biotinylated alanine substituted MPER peptides with single amino acid substitution of each MPER residue. Residues circled on top indicate the critical residues (in red (underlined) with >50% reduction in binding to alanine substituted peptide) required for binding to the MPER peptide. Residues in blue (not underlined) indicate residues with lower degree of involvement (<20-50% reduction in binding).

Results

The presented experimental data shows the application of the designed MPER liposomal immunogens in the induction of antibodies that are targeted to the neutralizing epitopes on gp41 of HIV-1 Envelope protein. The data shows that the constructed MPER peptide liposomes are immunogenic in small animals like guinea pigs and non-human primates (NHP) and that the induced antibody responses are specific for the core neutralizing epitope on gp41MPER. These studies also demonstrate the application of prime-boost strategy in enhancement of the MPER specific responses and in focusing of the antibody responses to the core neutralizing epitopes that include the 2F5 core residues DKW. In the presented immunization scheme, the data shows a shift in the binding epitope in initial responses from residues that are N-terminus to the core DKW to responses that include all three residues of the core neutralizing epitope (DKW) that are induced in later time points. Final immunizations with the MPER liposomes resulted in focusing of the antibody responses to the core DKW residues of the broad neutralizing mAb 2F5. These data represents application of the design of MPER immunogens in liposomal form for the induction of MPER specific antibodies in experimental animals like guinea pigs (FIG. 17) and NHP (FIG. 18). Such MPER immunogen designs can be candidates for human trials.

Example 5

Figure 18A:
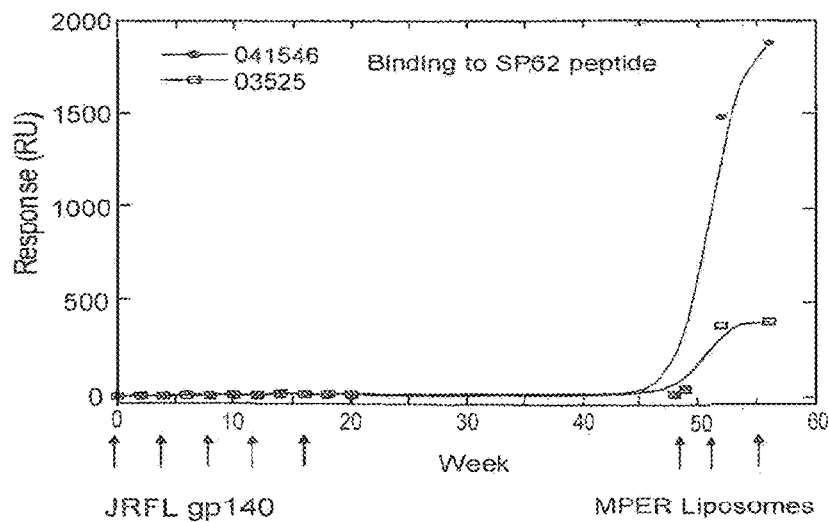

As shown in FIG. 18A, MPER specific binding responses were not induced following priming with gp140 Env protein but were induced following boosting with MPER liposomes. No binding responses to MPER peptides were detected following multiple immunizations with gp140 protein. Boosting of the same animals with MPER-656 liposomes resulted in MPER specific responses that were specific for the 2F5 nominal epitope peptide.

Figure 18B:
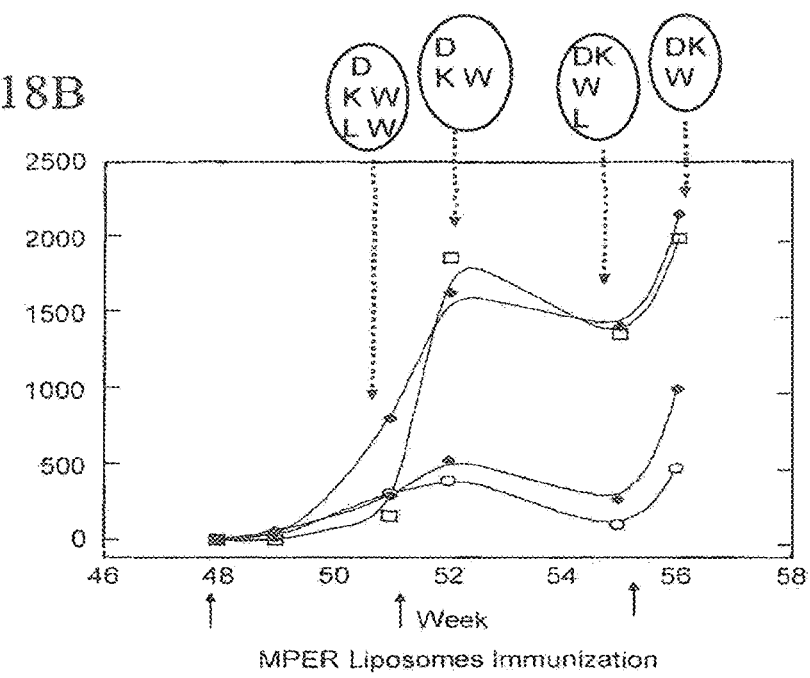
Figure 19:
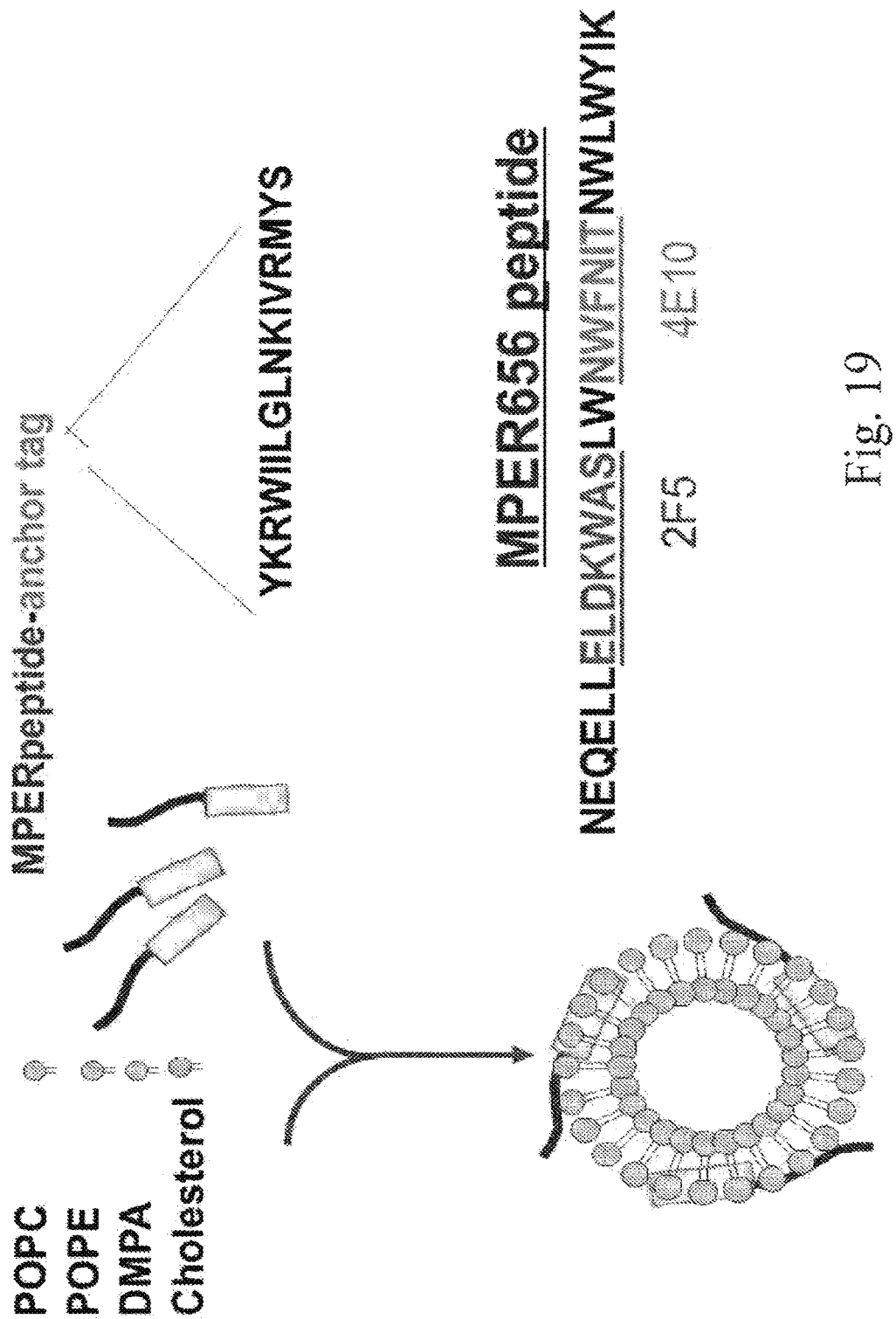

As shown in FIG. 18B, epitope mapping of the antibody responses show focusing of the response to the neutralizing 2F5 core residues DKW. An initial broader specificity was focused to the DKW core residues after the third immunization.

Binding data from four NHP immunized sera are shown. Binding response measurements and epitope mapping experiments were done as described in FIG. 17.

Example 6: Design of MPER Peptide for a Polyvalent MPER-Liposome Conjugate Vaccine (FIGS. 19-24)

The original MPER vaccine sequence matches HXB2—it has a single rare amino acid in it, otherwise it resembles the B clade consensus. That substitution doesn't impact 4E10 or 10E8 but it is in the contact region, other antibodies against this epitope might be weakened. There is extensive variation in the epitope, but it doesn't affect 4E10 or 10E8. To extend coverage of multiple clades, the invention provides three additional MPER peptides (MPER656.1-3). In certain aspects the invention provides that much of that extensive epitope variation can be covered with a four-valent vaccine, for example but not-limited to the peptide design described in FIGS. 19-24, to try to mimic that antibody behavior.

mAb 2F5 does have a lot of sequence and clade specificity. The original MPER peptide matches the B clade in that epitope. A polyvalent vaccine, for example but not limited to a four-valent vaccine, provides a candidate for a global vaccine, as it is believed that adding the variants could impact breadth. There are 368 variants of the 2F5 epitope "ELDKWA" (SEQ ID NO: 45) found in 4036 sequences from different individuals in the database, and there were 104 different forms found in just the 1010 B clade sequences. Non-limiting example are provided herein which are "central"—they each are common regionally, and the more diverged forms of the epitope tend to build off of these basic forms.

```
MPER656.ori
                                       (SEQ ID NO. 9)
NEQELLELDKWASLWNWFNITNWLWYIK original MPER656.1
                                       (SEQ ID NO. 10)
NEQDLLALDKWASLWNWFDISNWLWYIK MPER656.2
                                       (SEQ ID NO. 11)
NEKDLLALDSWKNLWNWFSITKWLWYIK MPER656.3
                                       (SEQ ID NO. 12)
NEQELLALDKWNNLWSWFDITNWLWYIR MPER656.ori-anchor
                                       (SEQ ID NO. 13)
NEQELLELDKWASLWNWFNITNWLWYIK-GTH1 original MPER656.1-anchor
                                       (SEQ ID NO. 14)
NEQDLLALDKWASLWNWFDISNWLWYIK-GTH1

MPER656.2-anchor
                                       (SEQ ID NO. 15)
NEKDLLALDSWKNLWNWFSITKWLWYIK-GTH1

MPER656.3-anchor
                                       (SEQ ID NO. 16)
NEQELLALDKWNNLWSWFDITNWLWYIR-GTH1

(SEQ ID NO: 17)
GTH1 sequence is YKRWIILGLNKIVRMYS.
```

In certain embodiments the anchor is TMD peptide (US Pub. 20100047331 A1).

```
2F5 epitope:
                                       (SEQ ID NO: 1)
ELDKWAS;

(SEQ ID NO: 3)
ALDKWAS;

(SEQ ID NO: 5)
ALDSWKN;

(SEQ ID NO: 7)
ALDKWNN;

(SEQ ID NO: 18)
NEQELLELDKWAS;

(SEQ ID NO: 19)
NEQDLLALDKWAS;

9SEQ ID NO: 20)
NEKDLLALDSWKN;

(SEQ ID NO: 21)
NEQELLALDKWNN.

4E10/10E8 contacts:
                                       (SEQ ID NO: 2)
NWFNIT;

(SEQ ID NO: 4)
NWFNIT;

(SEQ ID NO: 6)
NWFSIT;

(SEQ ID NO: 8)
SWFDIT;

(SEQ ID NO: 22)
NWFNITNWLWYIK;

(SEQ ID NO: 23)
NWFDISNWLWYIK;

(SEQ ID NO: 24)
NWFSITKWLWYIK;

(SEQ ID NO: 25)
SWFDITNWLWYIR.

CAP206_0moB5_MPER656
                                       (SEQ ID NO: 26)
NEKDLLALDSWKNLWNWFDITKWLWYIK

CAP206_0moB5_MPER656
                                       (SEQ ID NO: 27)
NEKDLLALDSWKNLWNWFDITKWLWYIK-GTH1

MPER656_biotin
                                       (SEQ ID NO: 28)
KKKNEQELLELDKWASLWNWFNITNWLWYIKKKK-biotin MPER656.1_biotin
                                       (SEQ ID NO: 29)
KKKNEQDLLALDKWASLWNWFDISNWLWYIKKKK-biotin MPER656.2_biotin
                                       (SEQ ID NO: 30)
KKKNEKDLLALDSWKNLWNWFSITKWLWYIKKKK-biotin MPER656.3_biotin
                                       (SEQ ID NO: 31)
KKKNEQELLALDKWNNLWSWFDITNWLWYIRKKK-biotin CAP206_0moB5_MPER656_biotin
                                       (SEQ ID NO: 32)
KKKNEKDLLALDSWKNLWNWFDITKWLWYIKKKK-biotin
```

Methods of Inducing Antibodies with the Composition of the Invention

Various immunization schedules are contemplated by the methods of the invention, either in a sequential prime and boost schedule using individual MPER-liposome conjugates, for example but not limited to the ones described in FIGS. 19-24, or in a swarm prime and boost schedule, using various combinations of the MPER-liposome conjugates, for example but not limited to the ones described in FIGS. 19-24.

Figure 20:
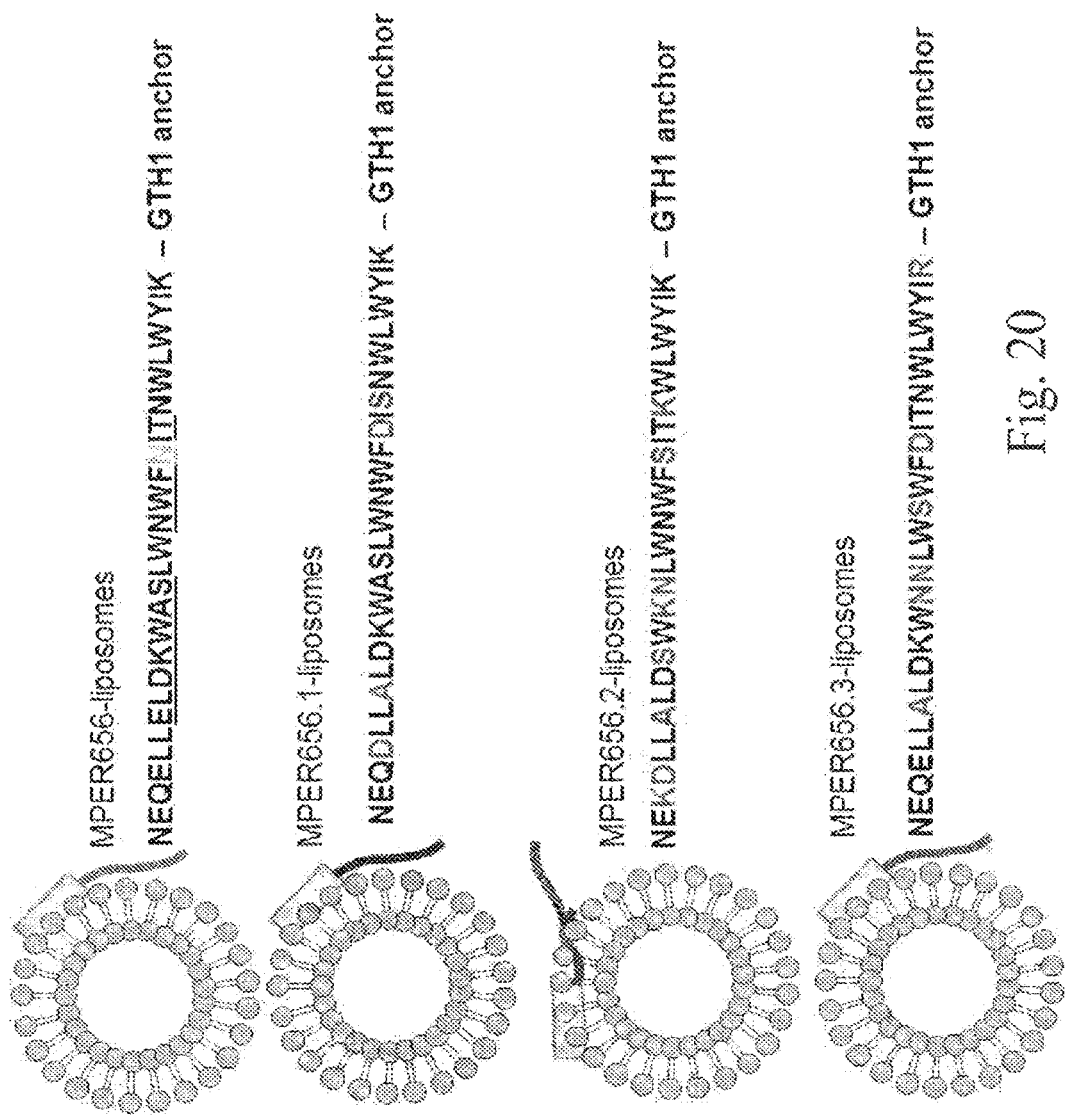
Figure 21A:
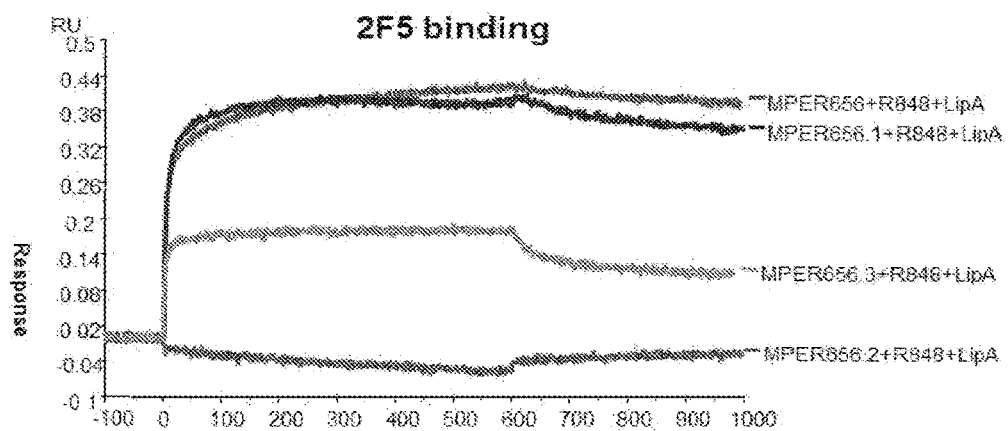
Figure 21B:
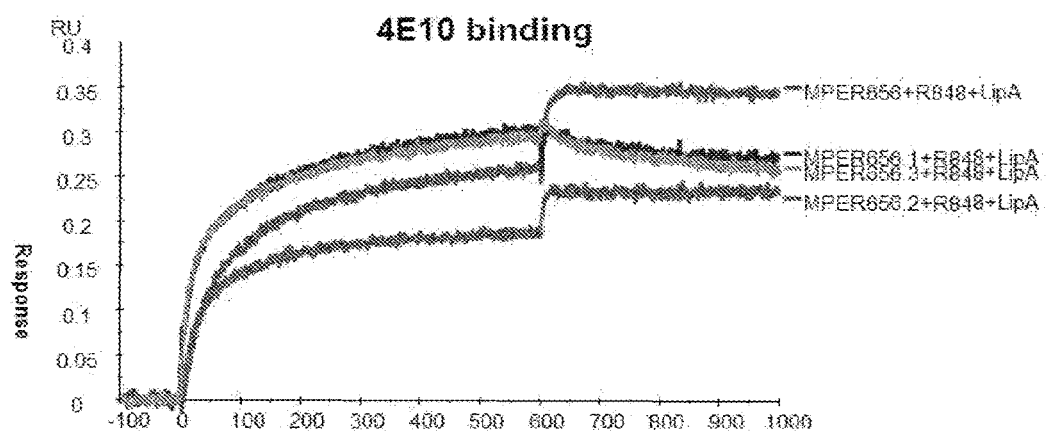
Figure 22B:
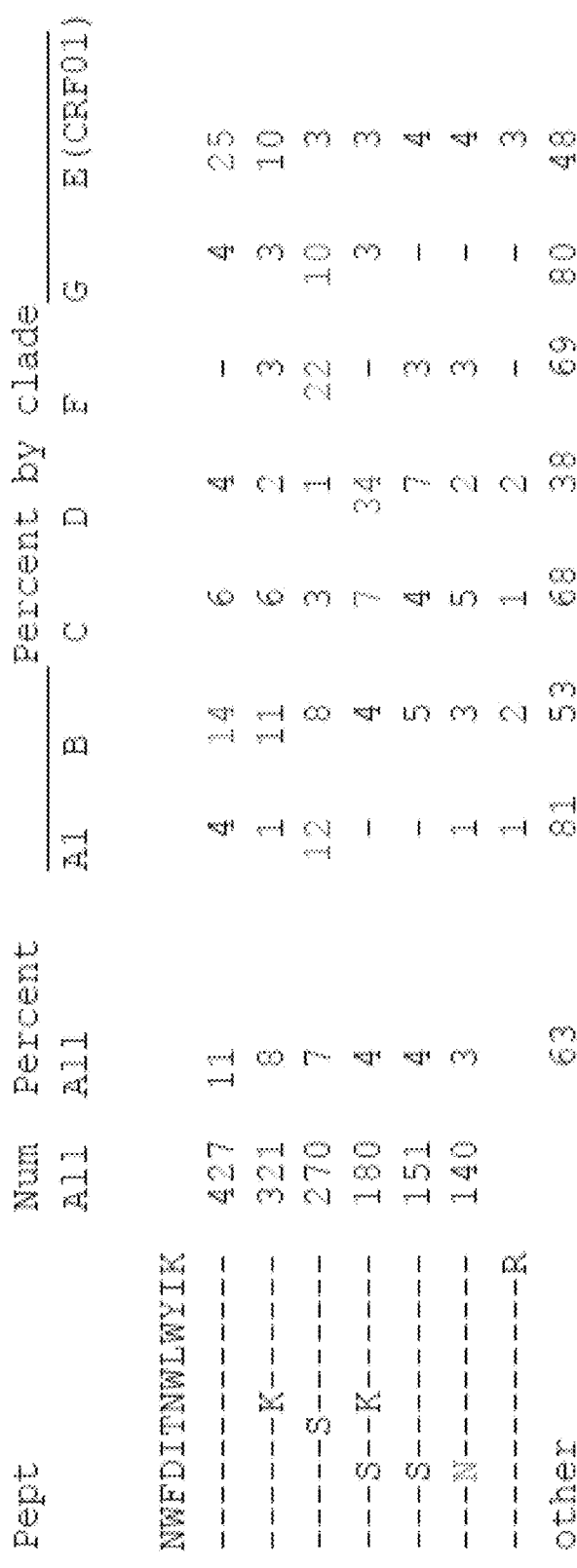
Figure 23:
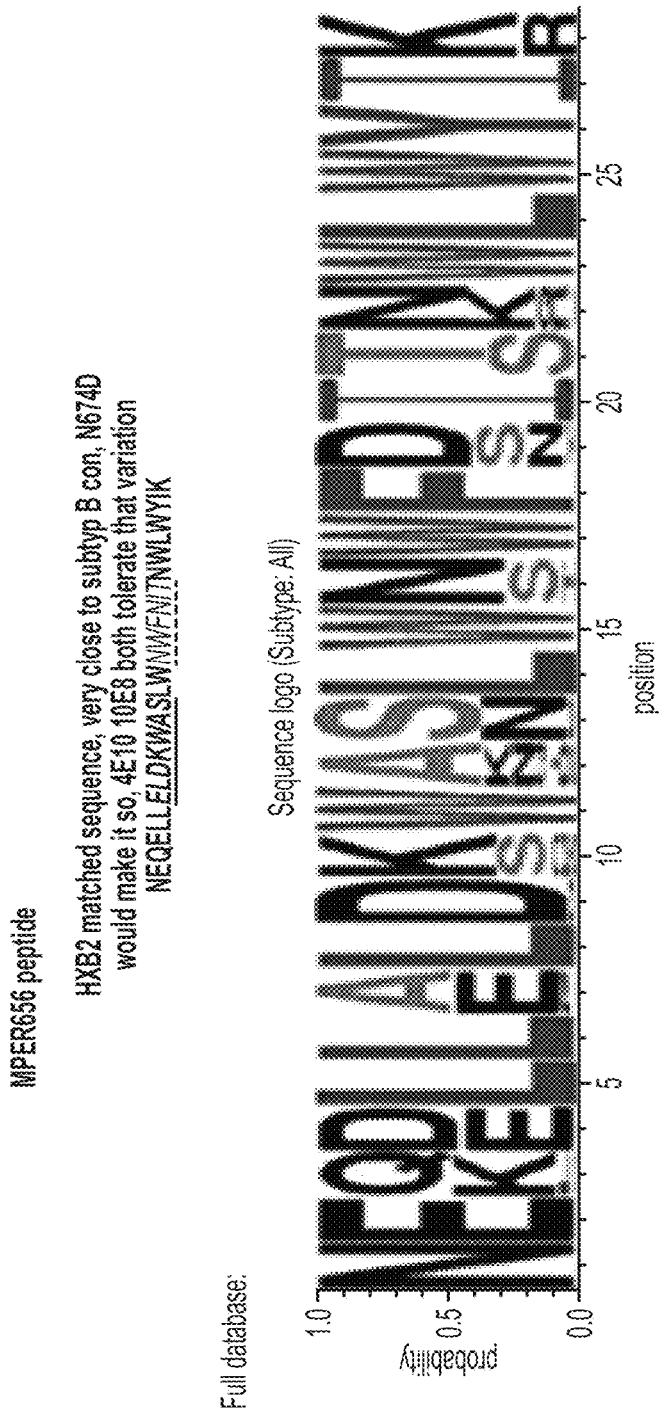
Figure 23:
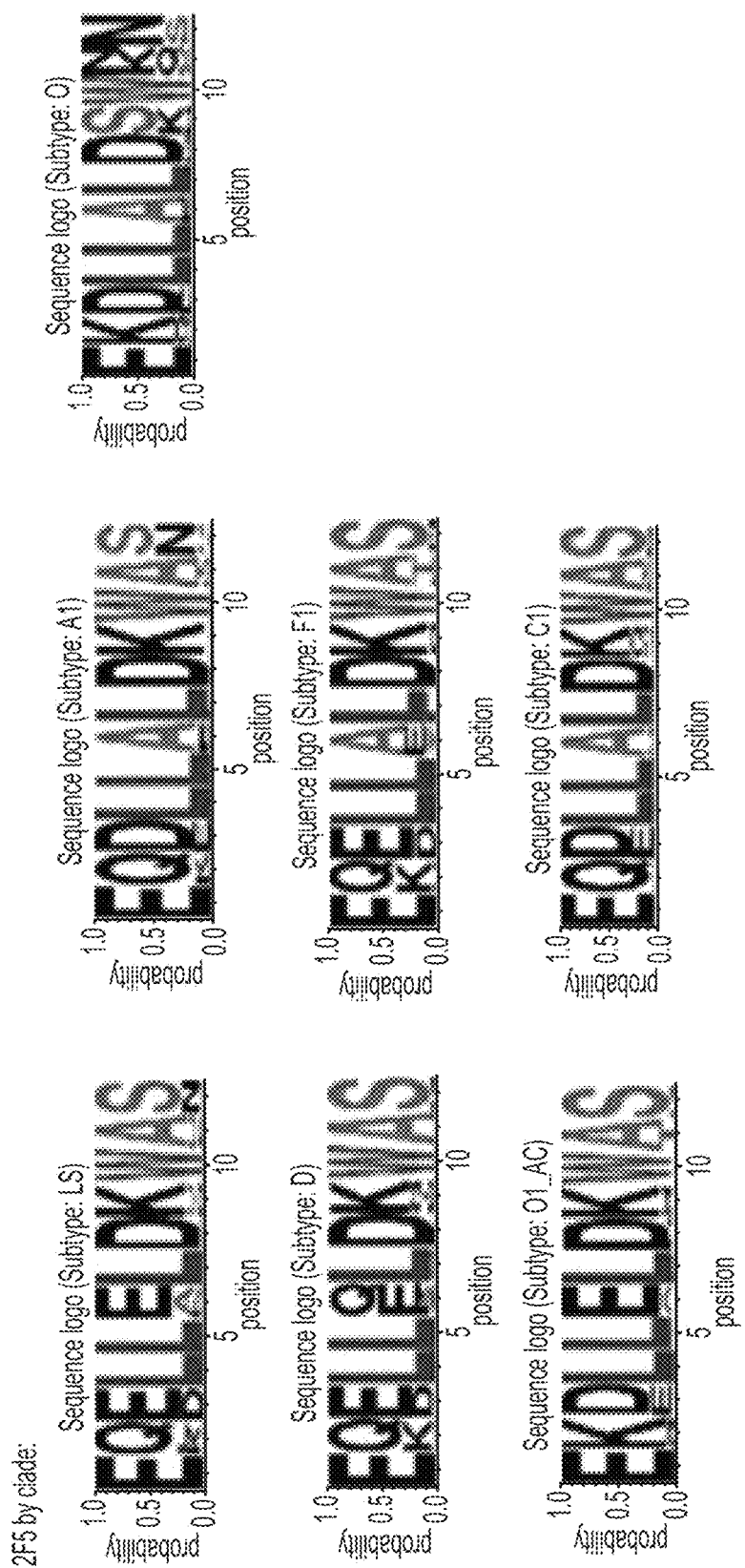
Figure 23:
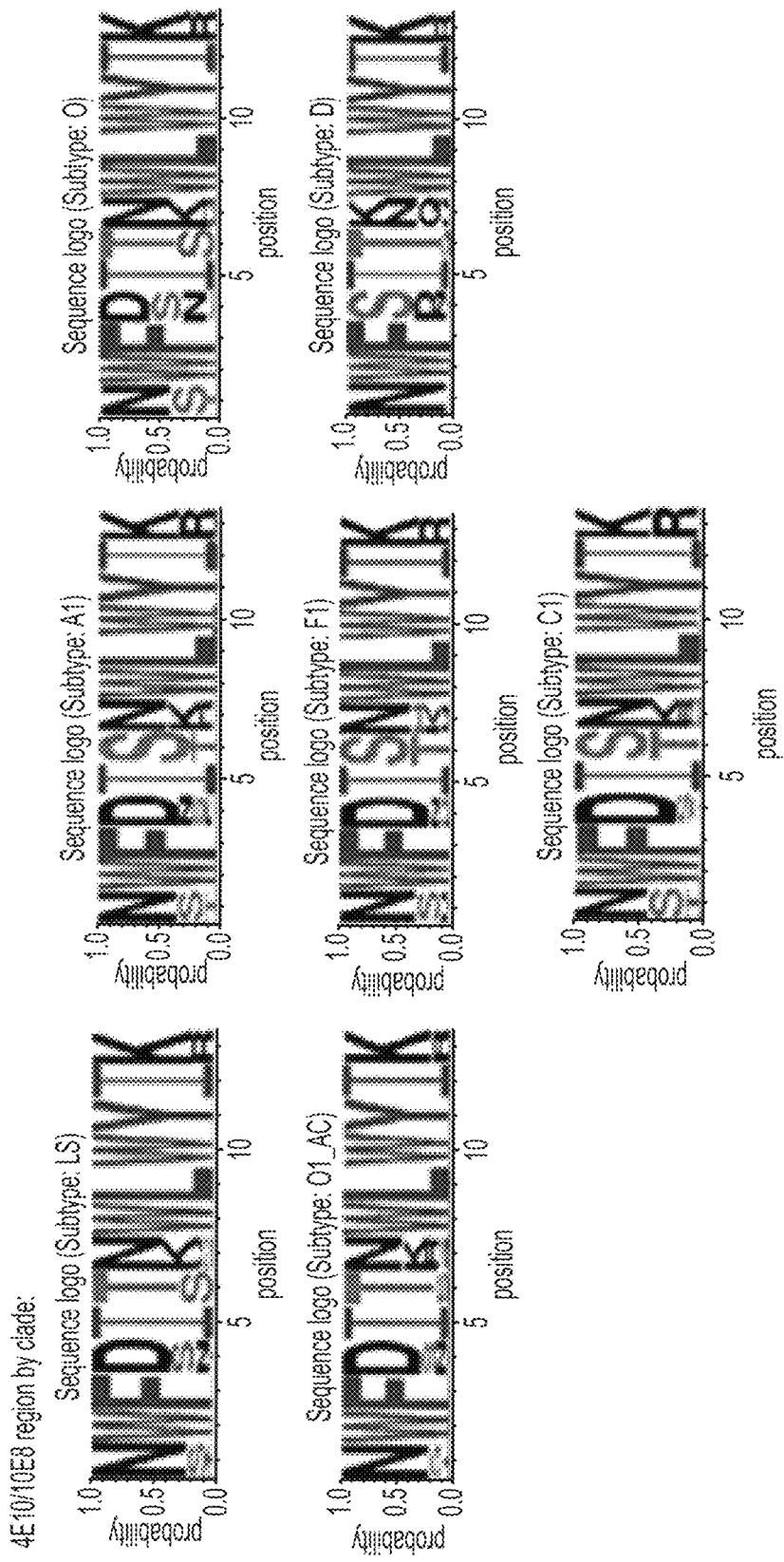
Figure 24:
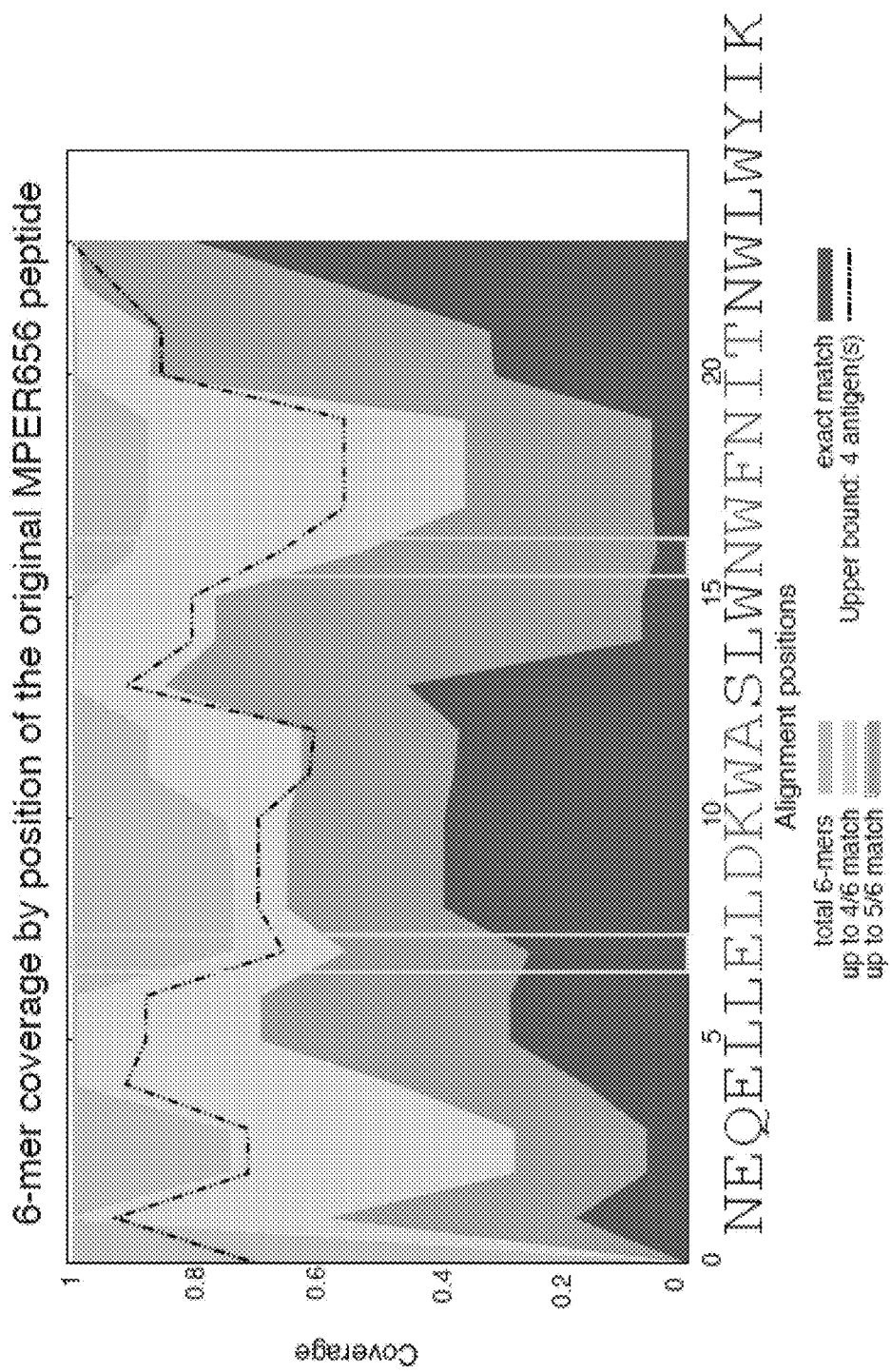
Figure 24:
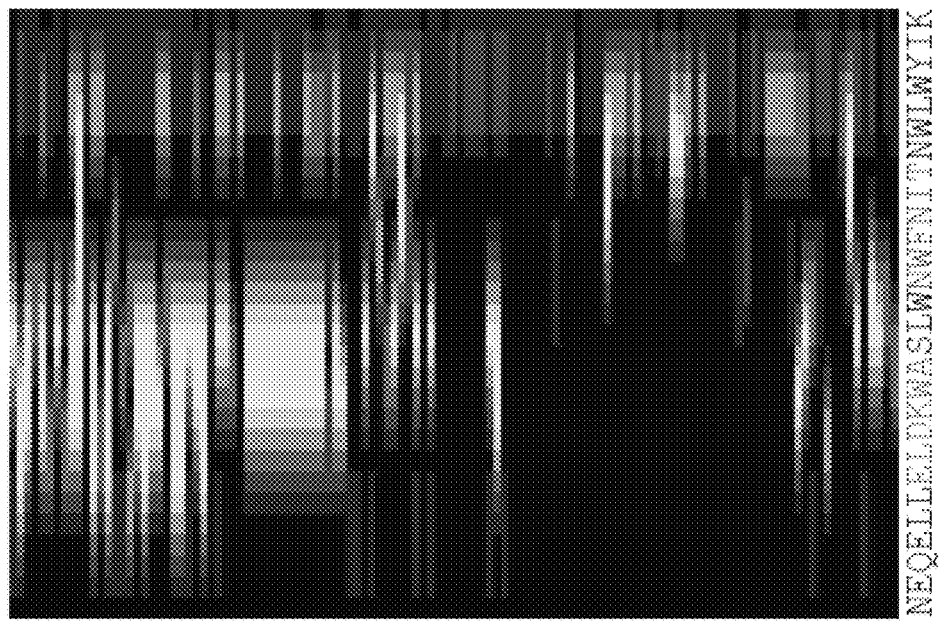
Figure 24:
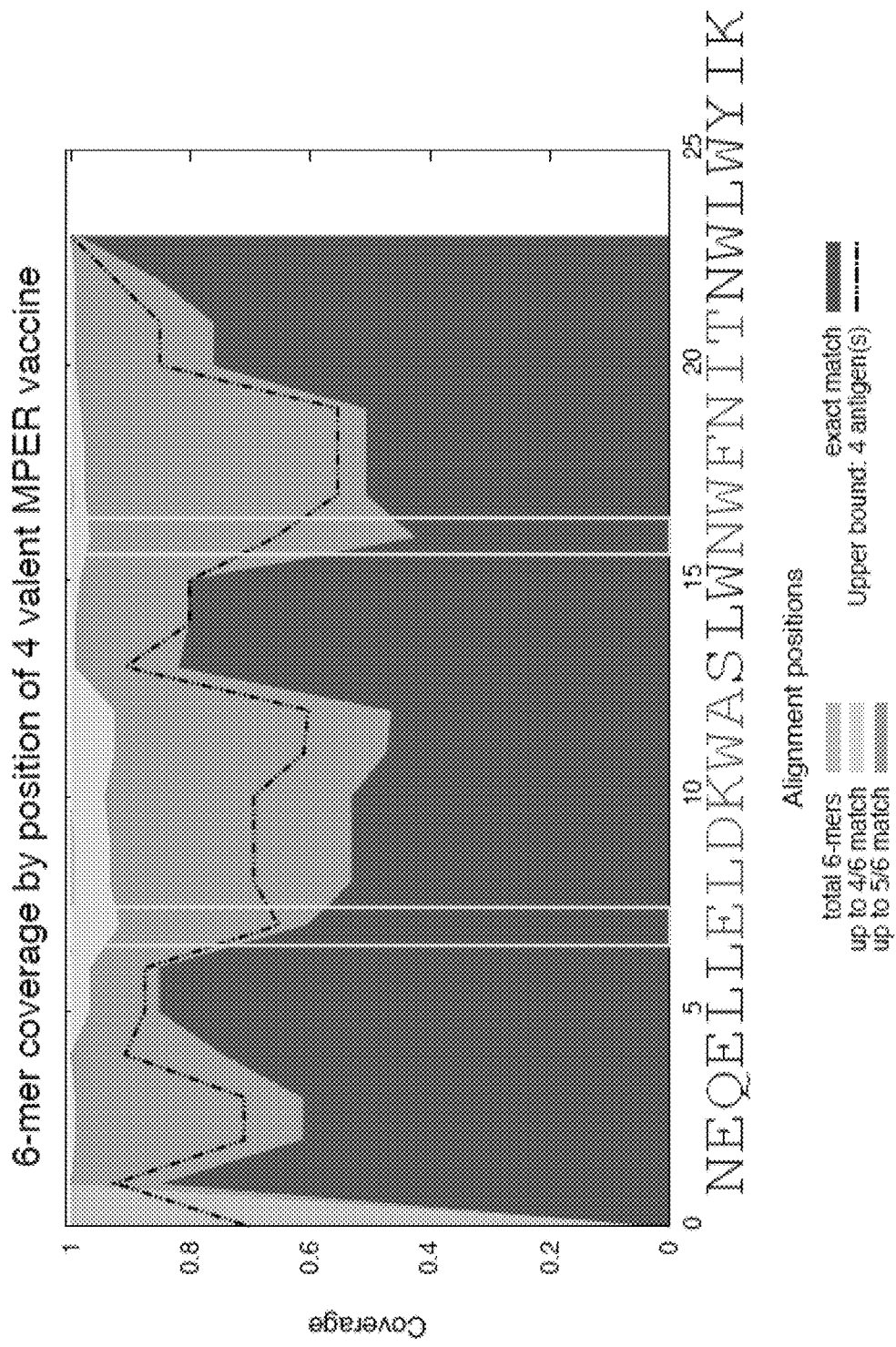
Figure 24:
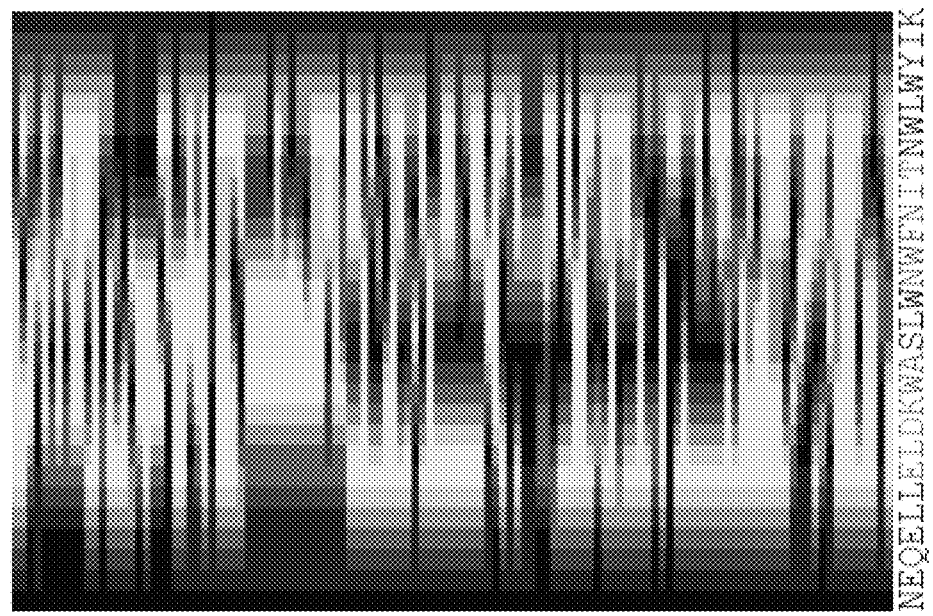
Figure 25:
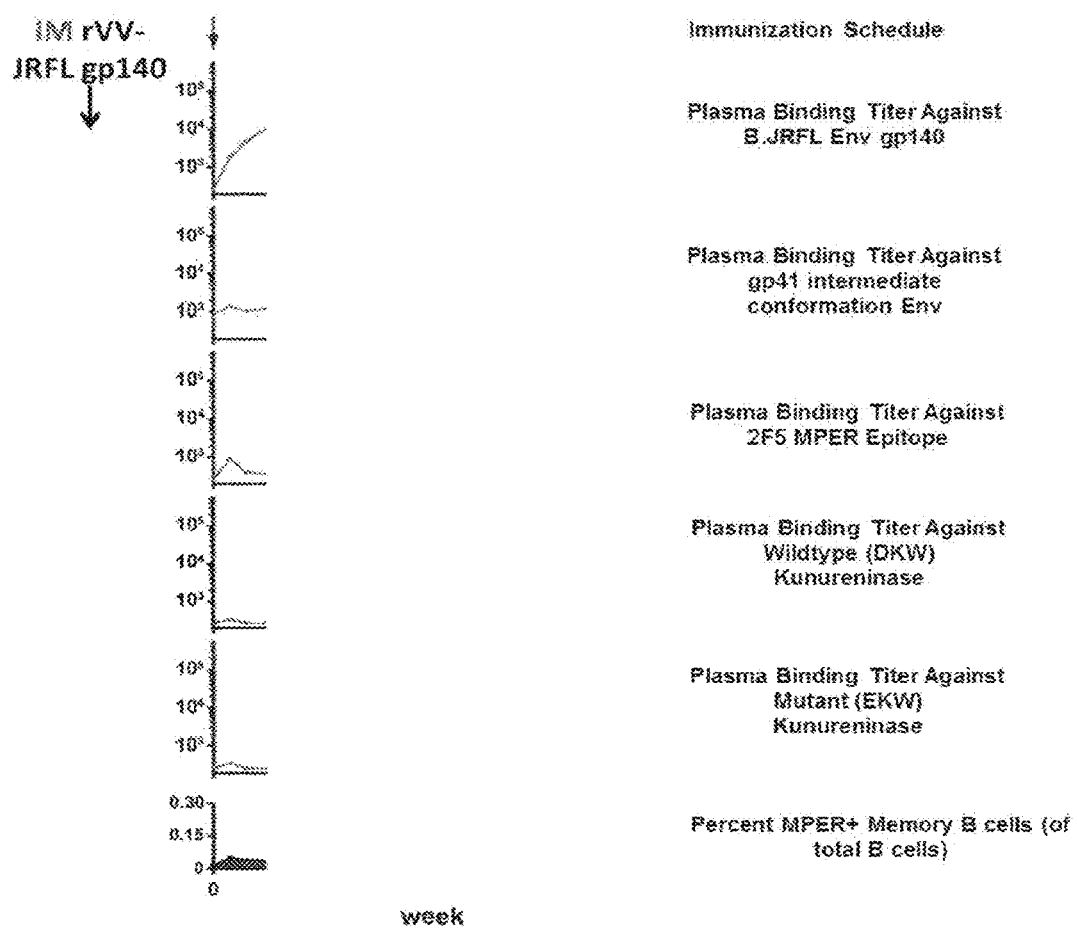
Figure 27:
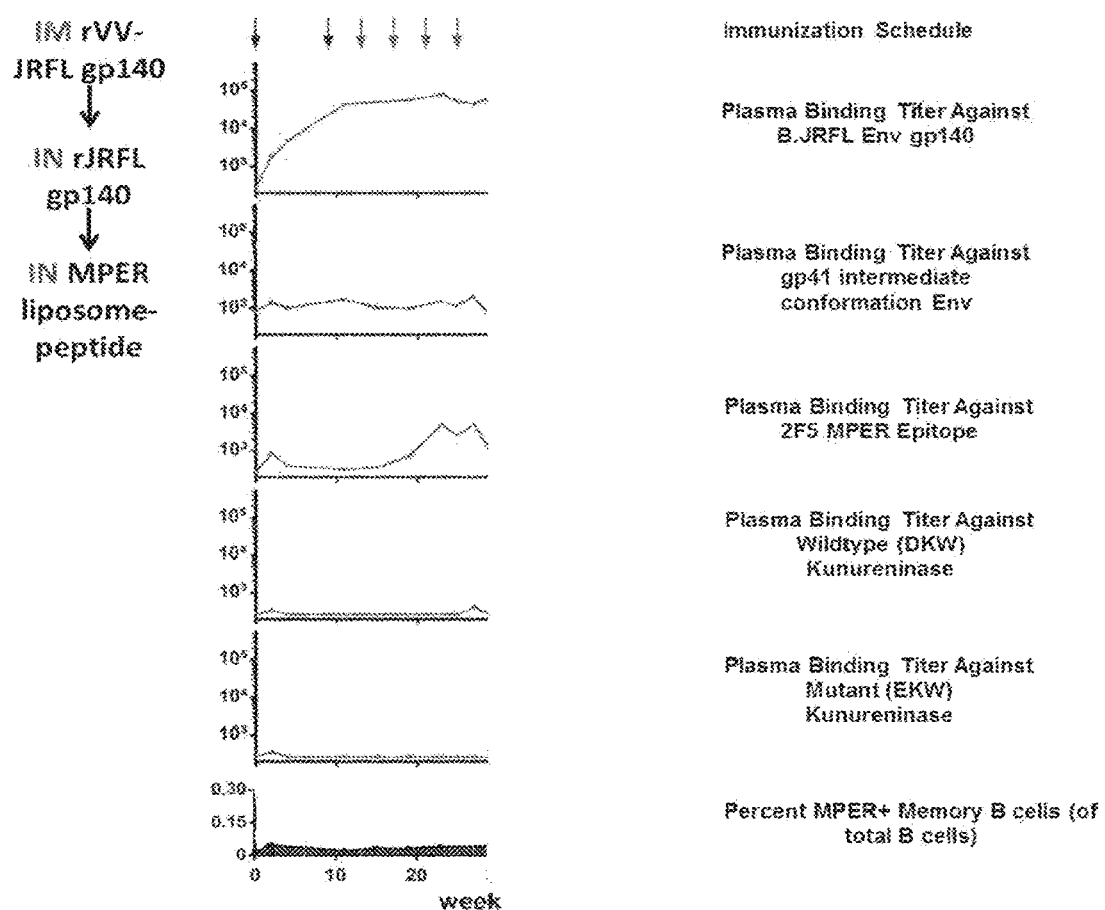
Figure 29:
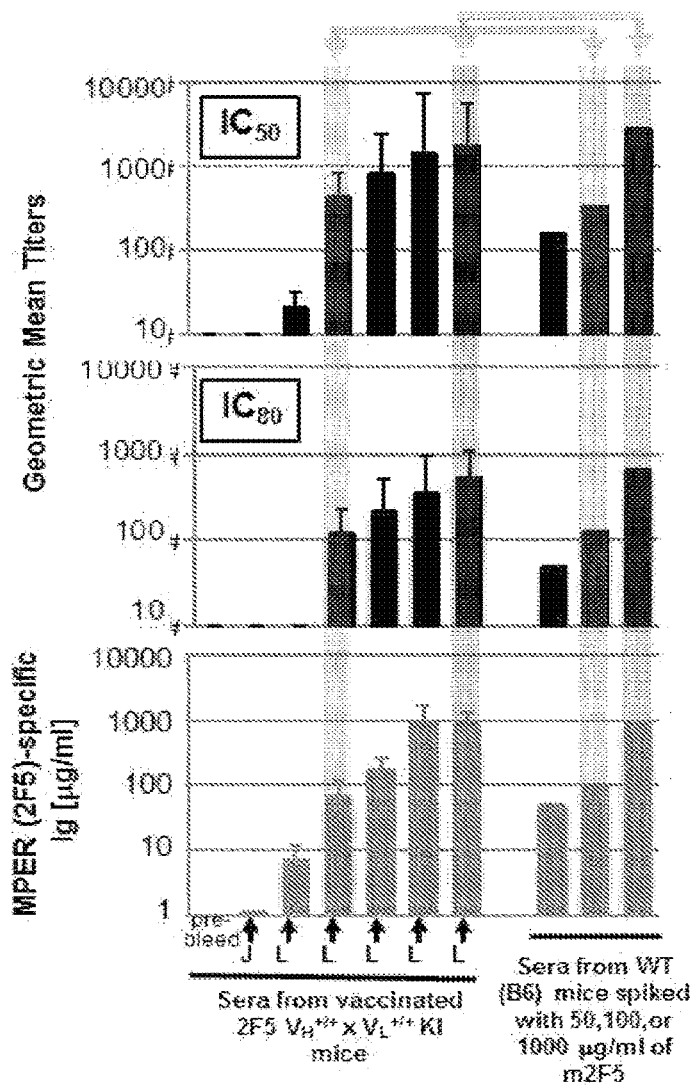
Figure 30:
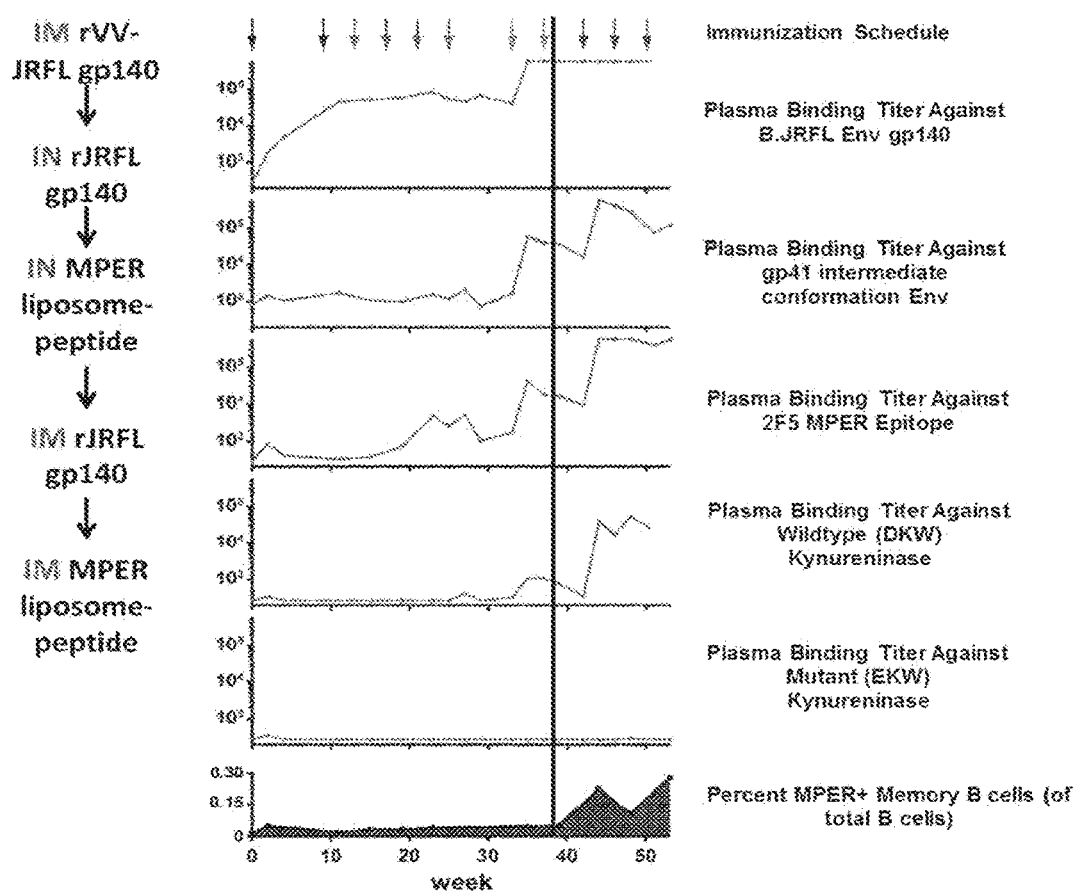
Figure 32:
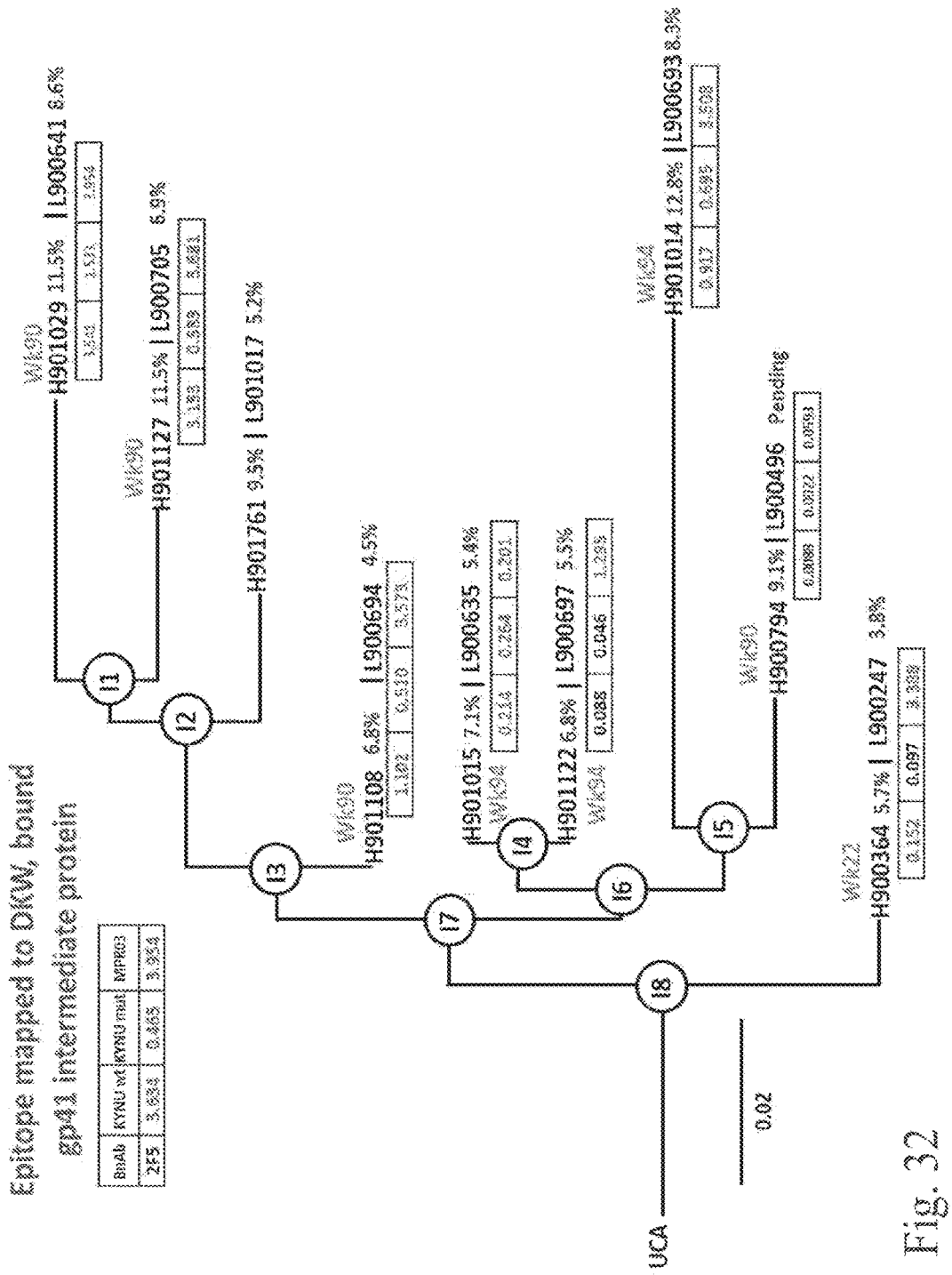
Figure 33:
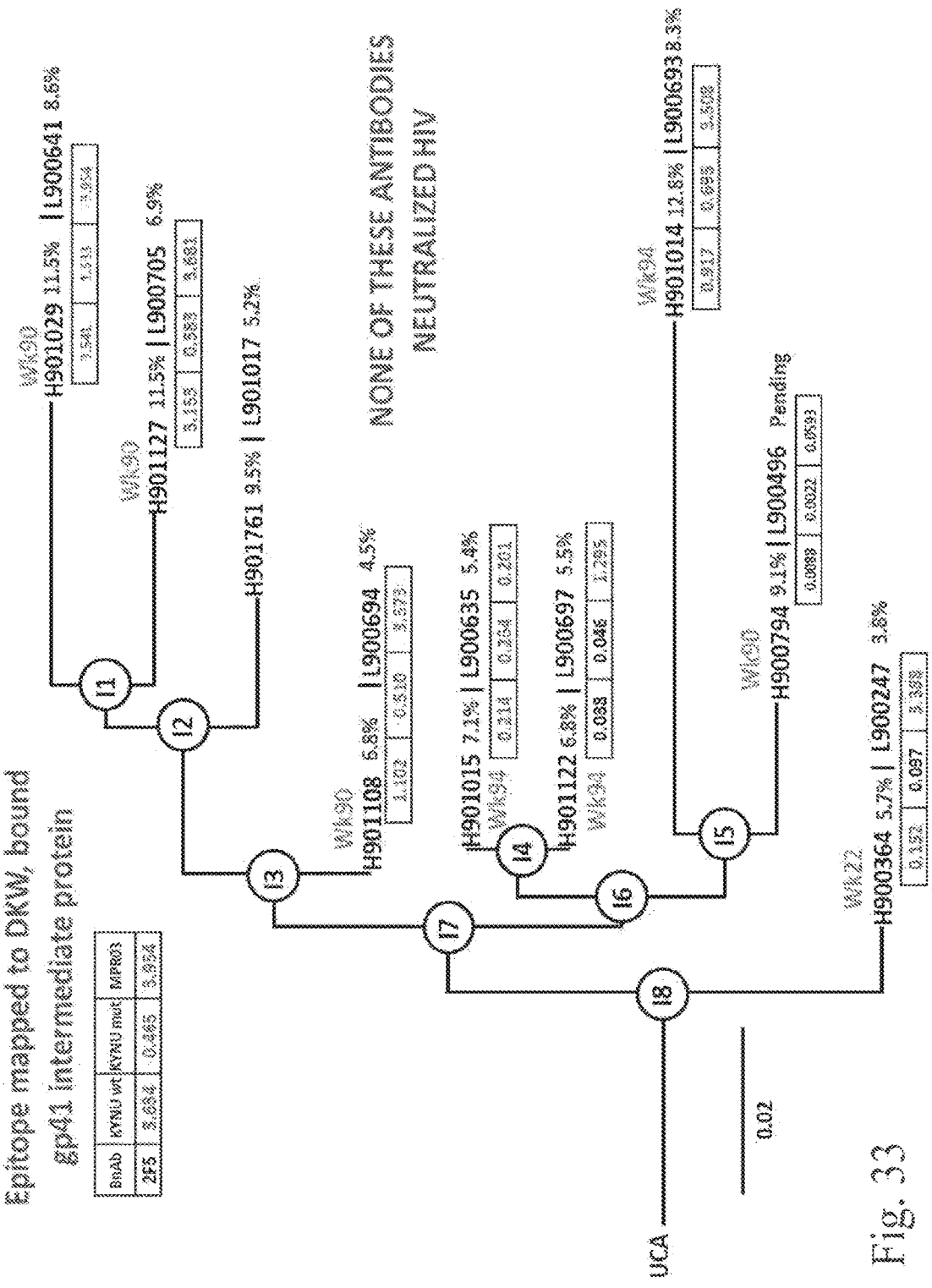
Figure 34:
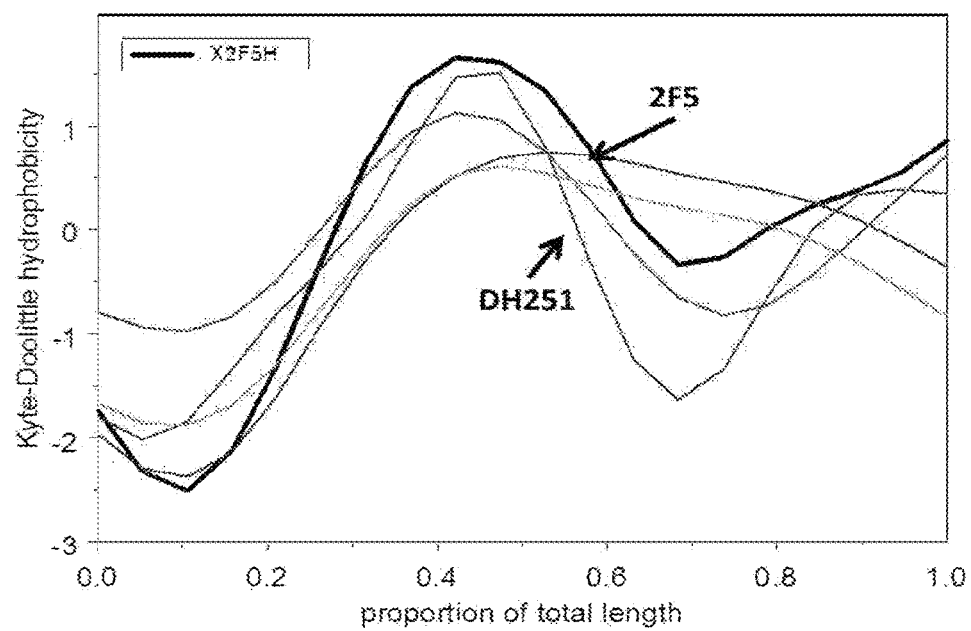
Figure 35:
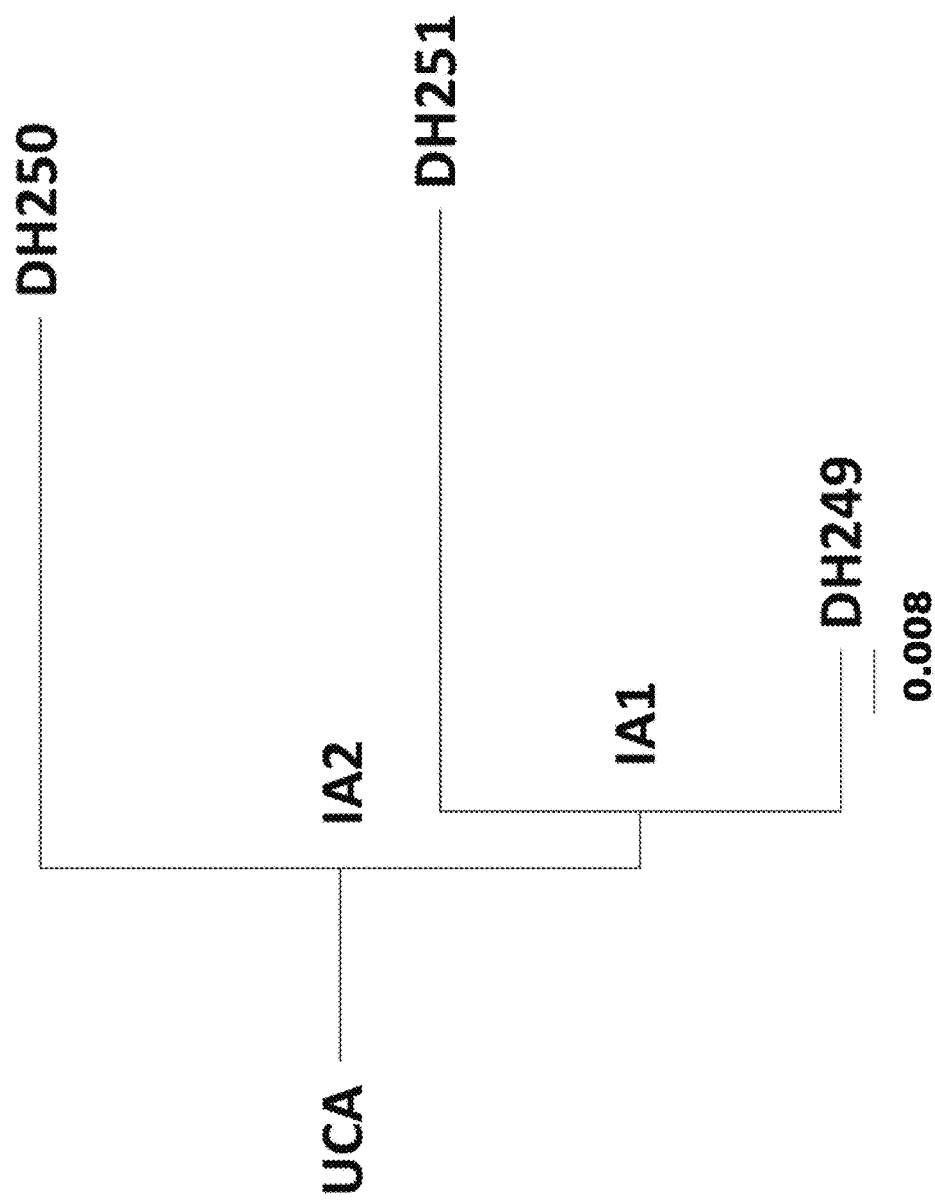
Figure 36:
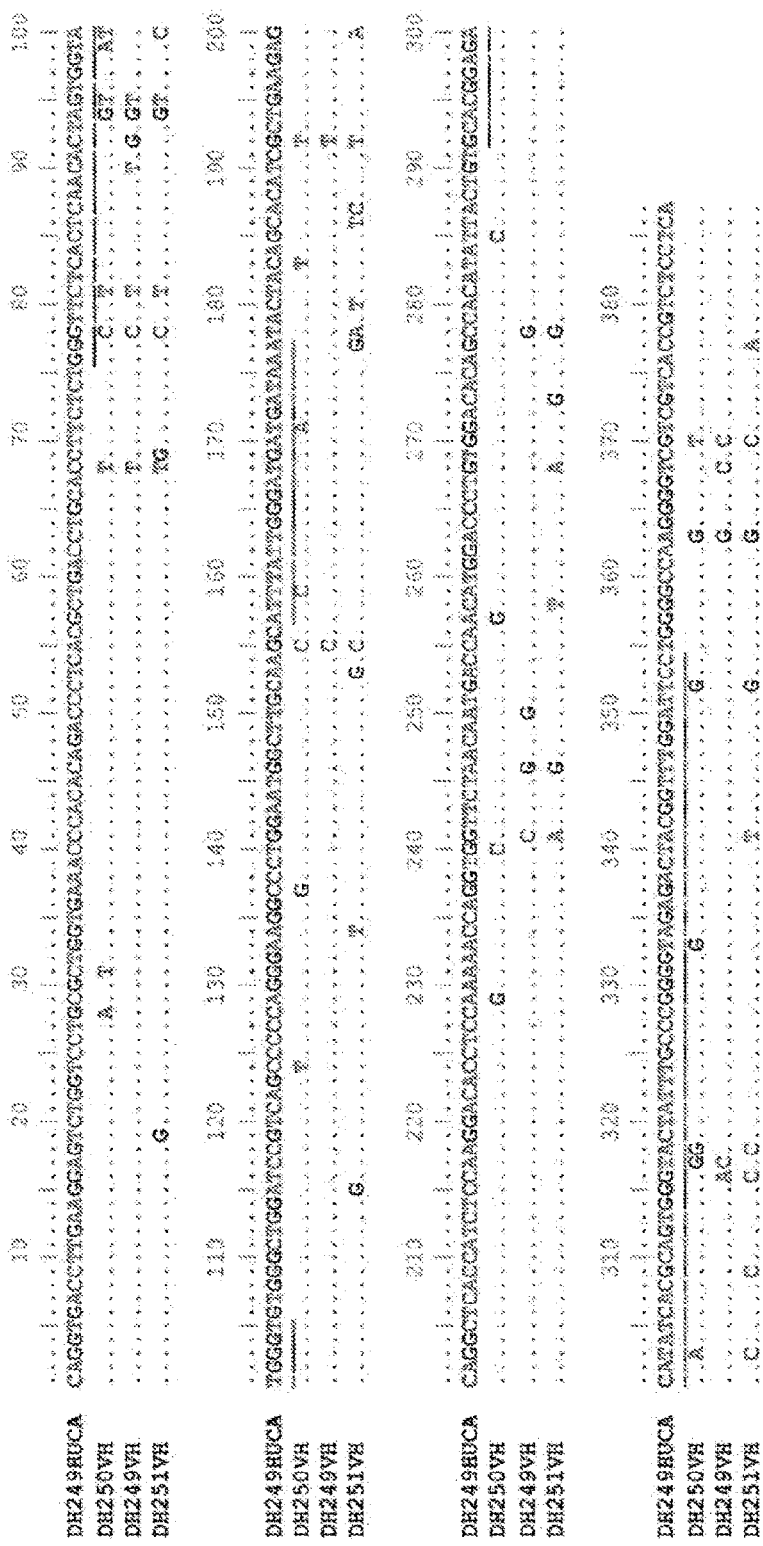

In a non-limiting embodiment, the vaccination schedule contemplates sequential vaccination using compositions comprising individual MPER-liposome conjugates, for example each one of the four MPER-liposome conjugates as described in FIG. 20. In a non-limiting embodiment, the vaccination schedule contemplates priming with the original MPER656-liposome conjugate, followed by immunization with the MPER656.1-liposome conjugate, followed by immunization with the MPER656.2-liposome conjugate, and followed by immunization with the MPER656.3-liposome conjugate.

In another non-limiting embodiment, the vaccination schedule contemplates swarm vaccination using compositions comprising various combinations of the MPER-liposome conjugates. In a non-limiting example a prime is given with all four MPER-liposome conjugates as described in FIG. 20, followed by a boost by all four MPER-liposome conjugates as described in FIG. 20, and followed by subsequent boost(s) with all four MPER-liposome conjugates as described in FIG. 20, on a schedule which is readily determined by a skilled artisan.

In another non-limiting embodiment, the vaccination schedule contemplates priming with the original MPER656-liposome conjugate, followed by immunization with combinations of other liposomes, for example a combination of the original MPER656-liposome conjugate and the MPER656.1-liposome conjugate, followed by a combination of the original MPER656-liposome conjugate, the MPER656.1-liposome conjugate and MPER656.2-liposome conjugate, followed by a combination of the original MPER656-liposome conjugate, the MPER656.1-liposome conjugate, MPER656.2-liposome conjugate and MPER656.3-liposome conjugate.

Immunogenicity of the inventive compositions and antibody induction in response to immunization by various schedules as contemplated by the methods of the invention can be measured by various methods known in the art.

Example 7: 2F5-Like Antibodies (DH249 Clonal Lineage) Induced in Rhesus Macaques Using HIV-1 Env MPER Peptide-Liposomes (Study NHP#22)

NHP #22-JRFL gp140 natively deglycosylated Env prime (that binds UCAs of 2F5) (Ma, B et al. PLoS Pathogens 9: e10022000, 2011), and MPER peptide-liposome boost (J. Virol. 85: 11725, 2011). Goal: induce MPER BnAb lineages such as 2F5 or 4E10. Criteria: induced antibodies bind gp41 inter, map to nAb epitope in MPER, bind by two step mechanism.

Analyses showed that of 2F5 BnAb have the following characteristics: Long hydrophobic loop with LF at loop tip—binds to viral membrane; RR at base of the HCDR3—binds to "D664" of DKW of gp41 MPER; Aspartic acid triplet (DDD) in HCDR2—binds to "K665" of DKW of gp41 MPER.

Data presented in example 7, FIGS. 25-42, show success in inducing the right type of broad neutralizing antibodies to membrane proximal external region (MPER) of gp41.

Additional MPER-liposomes combinations as contemplated herein can be analyzed by the methods and assays described in Example 7.

Example 8

This example provides results of non-human primate (NHP) immunization studies with peptide liposome immunogens formulated with different adjuvants. The immunization strategy is shown in FIG. 43. Plasma analyses as shown in FIGS. 44-48 demonstrate that all MPER-peptide liposomes are immunogenic and induce immune response in NHP.

Further studies will be carried to out to determine plasma neutralization properties. Samples from various time points post immunization could be analyzed by any suitable method to determine whether specific antibodies or antibody lineages are induced. Such methods include but are not limited to deep sequencing, single cell sorting of B-cells to isolate and characterize antibodies induced by the MPER peptide immunizations.

All documents and other information sources cited above are hereby incorporated in their entirety by reference.

What is claimed is:

1. A composition comprising an MPER656-GTH1 peptide-liposome conjugate, wherein the peptide comprises SEQ ID NO: 10 (NEQDLLALDKWASLWNWFDISNWLWYIK), or SEQ ID NO: 11 (NEKDLLALDSWKNLWNWFSITKWLWYIK) and is embedded in the liposome, and wherein the liposome comprises an anionic lipid.

2. The composition of claim 1, wherein the liposome comprises cholesterol.

3. The composition of claim 1, wherein the liposome comprises cholesterol, POPC (1-Pahnitoyl-2-Oleoyl-sn-Glycero-3-Phosphocholine), POPE (1-Palmitoyl-2-Oleoyl-sn-Glycero-3-Phosphoethanolamine), and DMPA (1,2-Dimyristoyl-sn-Glycero-3-Phosphate).

4. The composition of claim 1, wherein the peptide consists of SEQ ID NOs: 14, or 15, and the liposome comprises cholesterol.

5. The composition of claim 1, further comprising a second MPER656-GTH1 peptide-liposome conjugate, wherein the peptide is embedded in the liposome and comprises a peptide of SEQ ID NO: 13, and wherein the liposome comprises an anionic lipid.

6. The composition of claim 1, wherein the composition further comprises one or more additional MPER656-GTH1 peptide-liposome conjugates wherein the peptide comprises SEQ ID NO: 9, 10, 11, or 12 and is embedded in the liposome, and wherein the MPER656-GTH1 peptide-liposome conjugate of claim 1 and the one or more additional MPER656-GTH1 peptide-liposome conjugates comprise different peptides.

7. The composition of claim 1, wherein the composition further comprises a second MPER656-GTH1 peptide-liposome conjugate, wherein the peptide comprises SEQ ID NO: 9 and is embedded in the liposome.

8. The composition of claim 7, wherein the composition further comprises a third MPER656-GTH1 peptide-liposome conjugate, wherein the peptide comprises SEQ ID NO: 10 or 11 and is embedded in the liposome and wherein the MPER656-GTH1 peptide-liposome conjugate of claim 1 and the third MPER656-GTH1 peptide-liposome conjugates comprise different peptides.

9. The composition of claim 4, wherein the composition further comprises one or more additional MPER656-GTH1 peptide-liposome conjugates wherein the peptide comprises SEQ ID NO: 13, 14, 15, or 16 and is embedded in the liposome and wherein the MPER656-GTH1 peptide-liposome conjugate of claim 4 and the one or more additional MPER656-GTH1 peptide-liposome conjugates comprise different peptides.

10. The composition of claim 4, wherein the composition further comprises a second MPER656-GTH1 peptide-liposome conjugate wherein the peptide comprises SEQ ID NO: 13 and is embedded in the liposome.

11. The composition of claim 10, wherein the composition further comprises a third MPER656-GTH1 peptide-liposome conjugate wherein the peptide comprises SEQ ID NO: 14 or 15 and is embedded in the liposome and wherein the MPER656-GTH1 peptide-liposome conjugate of claim 4 and the third MPER656-GTH1 peptide-liposome conjugates comprise different peptides.

12. The composition of claim 1, 2, or 4, further comprising an adjuvant.

13. A method of inducing an anti-HIV-1 antibody in a subject, the method comprising administering to the subject the composition of any one of claim 1, 4, 9, 10, or 11 in an amount sufficient to induce the anti-HIV-1 antibody.

14. The method according to claim 13, wherein the composition is administered as a prime or a boost.

15. The method of claim 13, wherein the antibody binds an epitope in SEQ ID NOs: 9, 10, or 11.

16. A synthetic peptide comprising SEQ ID NO: 14, or 15.

17. The composition of claim 1, wherein the liposome comprises POPC.

18. The composition of claim 17, wherein the liposome further comprises POPS (1-palmitoyl-2-oleoyl-sn-glycero-3-[phospho-L-serine]).

19. The composition of claim 18, wherein the liposome further comprises lysoPC (lysophosphorylcholine).

20. The composition of claim 17, wherein the liposome further comprises POPE, Sphingomyelin and cholesterol.

21. The composition of claim 2, wherein the liposome further comprises DOPC.

22. The composition of claim 2, wherein the liposome further comprises DPPC and DPPG.

23. The composition of claim 1, wherein the liposome comprises Sphingolipid.

24. The composition of claim 1, wherein the anionic lipid is phosphatidylserine, phosphatidic acid, or cardiolipin.

25. The composition of claim 1, 2 or 4, wherein the composition further comprises alum.

26. The composition of claim 1, 2 or 4, wherein the composition further comprises lipid A, oCpG, or TLR agonist.

27. The composition of claim 1, wherein the peptide comprises SEQ ID NO: 10 and the liposome comprises cholesterol.

28. The composition of claim 1, wherein the peptide comprises SEQ ID NO: 11 and the liposome comprises cholesterol.

29. The method of claim 13, wherein the composition comprises the peptide of SEQ ID NO: 14 and the liposome comprises cholesterol, and wherein the composition is administered as a boost.

30. The composition of claim 8, wherein the composition further comprises a fourth MPER656-GTH1 peptide-liposome conjugate wherein the peptide comprises SEQ ID NO: 12 and is embedded in the liposome.

31. The composition of claim 11, wherein the composition further comprises a fourth MPER656-GTH1 peptide-liposome conjugate wherein the peptide comprises SEQ ID NO: 16 and is embedded in the liposome.

* * * * *

UNITED STATES PATENT AND TRADEMARK OFFICE
CERTIFICATE OF CORRECTION

PATENT NO. : 10,076,567 B2
APPLICATION NO. : 15/024600
DATED : September 18, 2018
INVENTOR(S) : Barton F. Haynes et al.

Page 1 of 1

It is certified that error appears in the above-identified patent and that said Letters Patent is hereby corrected as shown below:

In the Specification

At Column 1, Line numbers 10-12 should read:
"The United States government has rights in this invention pursuant to Contract No. DE-AC52-06NA25396 between the United States Department of Energy and Los Alamos National Security, LLC for the operation of Los Alamos National Laboratory."

Signed and Sealed this
Twenty-sixth Day of January, 2021

Drew Hirshfeld
*Performing the Functions and Duties of the
Under Secretary of Commerce for Intellectual Property and
Director of the United States Patent and Trademark Office*